(12) United States Patent  
Cassayre et al.

(10) Patent No.: US 9,545,106 B2  
(45) Date of Patent: Jan. 17, 2017

(54) INSECTICIDAL COMPOUNDS

(75) Inventors: Jerome Yves Cassayre, Stein (CH); Peter Renold, Stein (CH); Myriem El Qacemi, Stein (CH); Thomas Pitterna, Stein (CH); Julie Clementine Toueg, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/118,573

(22) PCT Filed: May 30, 2012

(86) PCT No.: PCT/EP2012/060125  
§ 371 (c)(1),  
(2), (4) Date: Nov. 19, 2013

(87) PCT Pub. No.: WO2012/163959  
PCT Pub. Date: Dec. 6, 2012

(65) Prior Publication Data  
US 2014/0107056 A1    Apr. 17, 2014

(30) Foreign Application Priority Data

May 31, 2011  (EP) ..................................... 11168217  
Jul. 8, 2011   (EP) ..................................... 11173293

(51) Int. Cl.  
*C07D 413/00* (2006.01)  
*A01N 43/80* (2006.01)  
(Continued)

(52) U.S. Cl.  
CPC ............. *A01N 43/80* (2013.01); *C07D 261/02* (2013.01); *C07D 327/02* (2013.01);  
(Continued)

(58) Field of Classification Search  
USPC ................................ 548/518, 244; 546/272.1  
See application file for complete search history.

(56) References Cited

U.S. PATENT DOCUMENTS 4,207,327 A      6/1980 Lunsford et al.  
2015/0073139 A1  3/2015 Gorgens et al.

FOREIGN PATENT DOCUMENTS

CN    102770419 A    11/2012  
EP      1932836 A1    3/2007  
(Continued)

OTHER PUBLICATIONS

International Search Report and Written Opinion for International Patent Application No. PCT/EP2012/060125 dated Jul. 9, 2012.  
JP Patent Application 2014-513172; JP agent letter/Office Action dated Dec. 28, 2015.  
Stringer et al., Insecticidal activity and chemical constitution: Analogues and Isosters of DDT.  
Silverman, R.B., The organic chemistry of drug design and drug action, 2nd Edition, Elsevier Academic Press, 2004.

*Primary Examiner* — Nizal Chandrakumar  
(74) *Attorney, Agent, or Firm* — R. Kody Jones

(57) ABSTRACT

The present invention provides compounds of formula (I): wherein $A^1$, $A^2$, $A^3$ and $A^4$ are independently of one another C—H, C—$R^5$, or nitrogen; $B^1$—$B^2$—$B^3$—$B^4$ is —$CH_2$—C=N—$CH_2$—, —$CH_2$—N—$CH_2$—$CH_2$—, —$CH_2$—C=CH-0- or —CH=C—$CH_2$-0-; $G^1$ is oxygen or sulfur; L is a single bond or $C_1$-$C_8$alkylene; $R^1$ is hydrogen, $C_1$-$C_8$alkyl, $C_1$-$C_8$alkylcarbonyl-, $C_1$-$C_8$alkoxy, $C_2$-$C_8$alkenyl, $C_2$-$C_8$alkynyl, $C_1$-$C_8$alkoxy-$C_1$-$C_8$alkyl, aryl or aryl substituted by one to three $R^6$, or $R^1$ is heterocyclyl or heterocyclyl substituted by one to three $R^6$ or $C_1$-$C_8$alkoxycarbonyl-; $R^2$ is hydrogen, $C_1$-$C_8$haloalkyl or $C_1$-$C_8$alkyl; $R^3$ is $C_1$-$C_8$haloalkyl; $R^4$ is aryl or aryl substituted by one to three $R^6$, or $R^4$ is heterocyclyl or heterocyclyl substituted by one to three $R^6$; $Y^1$ is $CR^7R^8$, C=O or C=S; $Y^2$, $Y^3$ and $Y^4$ are independently $CR^7R^8$, C=0, C=S, N—$R^9$, O, S, SO or $SO_2$; wherein at least two adjacent ring atoms in the ring formed by $Y^1$, $Y^2$, $Y^3$ and $Y^4$ are heteroatoms; each $R^7$ and $R^8$ is independently hydrogen, halogen, $C_1$-$C_8$alkyl, or $C_1$-$C_8$haloalkyl; and $R^5$, $R^6$, $R^7$, $R^8$ and $R^9$ are as defined in the claims. The invention also relates to processes and intermediates for preparing these compounds, to insecticidal, acaricidal, nematicidal and molluscicidal compositions comprising these compounds and to methods of using these compounds to control insect, acarine, nematode and mollusc pests.

(I)

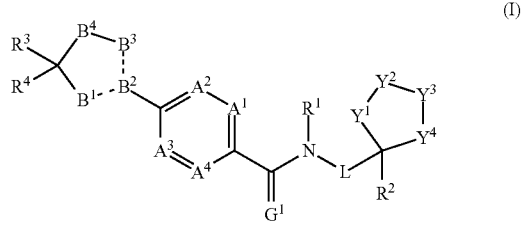

8 Claims, No Drawings

(51) Int. Cl.
*C07D 261/02* (2006.01)
*C07D 327/02* (2006.01)
*C07D 413/14* (2006.01)
*C07D 411/12* (2006.01)
*C07D 413/12* (2006.01)

(52) U.S. Cl.
CPC .......... *C07D 411/12* (2013.01); *C07D 413/12* (2013.01); *C07D 413/14* (2013.01)

(56) References Cited

FOREIGN PATENT DOCUMENTS

| | | |
|---|---|---|
| JP | S42-001284 B | 1/1967 |
| JP | 1979/041873 A | 10/1980 |
| JP | 2008/133273 A | 6/2008 |
| JP | WO 2010043315 * | 4/2010 |
| JP | 2010/116389 | 5/2010 |
| WO | 2010/020522 A1 | 2/2010 |
| WO | WO2010/043315 | 4/2010 |
| WO | 2011/067272 A1 | 6/2011 |
| WO | WO2011/101229 | 8/2011 |

* cited by examiner

INSECTICIDAL COMPOUNDS

RELATED APPLICATION INFORMATION

This application is a 371 of International Application No. PCT/EP2012/060125, filed 30 May 2012, which claims the benefit of European Patent Application No. 11168217.5, filed 31 May 2011 and European Patent Application No. 11173293.9, filed 8 Jul. 2011, the contents of which are incorporated herein by reference The present invention relates to certain heterocyclic benzamide derivatives, to processes and intermediates for preparing them, to insecticidal, acaricidal, nematicidal and molluscicidal compositions comprising them and to methods of using them to combat and control insect, acarine, nematode and mollusc pests.

Certain compounds with insecticidal properties are disclosed, for example, in EP 1,731,512.

It has now surprisingly been found that certain novel heterocyclic benzamide derivatives have insecticidal properties.

The present invention therefore provides a compound of formula (I):

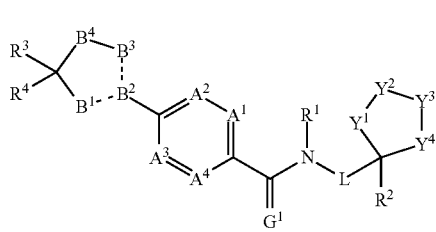

wherein
$A^1$, $A^2$, $A^3$ and $A^4$ are independently of one another C—H, C—$R^5$, or nitrogen;
$B^1$—$B^2$—$B^3$—$B^4$ is —$CH_2$—C=N—$CH_2$—, —$CH_2$—N—$CH_2$—$CH_2$—, —$CH_2$—C=CH—O— or —CH=C—$CH_2$—O—;
$G^1$ is oxygen or sulfur;
L is a single bond or $C_1$-$C_8$alkylene;
$R^1$ is hydrogen, $C_1$-$C_8$alkyl, $C_1$-$C_8$alkylcarbonyl-, $C_1$-$C_8$alkoxy, $C_2$-$C_8$alkenyl, $C_2$-$C_8$alkynyl, $C_1$-$C_8$alkoxy-$C_1$-$C_8$alkyl, aryl or aryl substituted by one to three $R^6$, or $R^1$ is heterocyclyl or heterocyclyl substituted by one to three $R^6$ or $C_1$-$C_8$alkoxycarbonyl-;
$R^2$ is hydrogen, $C_1$-$C_8$haloalkyl or $C_1$-$C_8$alkyl;
$R^3$ is $C_1$-$C_8$haloalkyl;
$R^4$ is aryl or aryl substituted by one to three $R^6$, or $R^4$ is heterocyclyl or heterocyclyl substituted by one to three $R^6$;
each $R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, or two $R^5$ on adjacent carbon atoms together form a —CH=CH—CH=CH— bridge or a —N=CH—CH=CH— bridge;
each $R^6$ is independently halogen, cyano, nitro, $C_1$-$C_8$alkyl, $C_1$-$C_8$haloalkyl, $C_1$-$C_8$alkoxy, or $C_1$-$C_8$haloalkoxy;
$Y^1$ is $CR^7R^8$, C=O or C=S;
$Y^2$, $Y^3$ and $Y^4$ are independently $CR^7R^8$, C=O, C=S, N—$R^9$, O, S, SO or $SO_2$;
wherein at least two adjacent ring atoms in the ring formed by $Y^1$, $Y^2$, $Y^3$ and $Y^4$ are heteroatoms;
each $R^7$ and $R^8$ is independently hydrogen, halogen, $C_1$-$C_8$alkyl, or $C_1$-$C_8$haloalkyl;
each $R^9$ is independently hydrogen, cyano, cyano-$C_1$-$C_8$alkyl, $C_1$-$C_8$alkyl, $C_1$-$C_8$haloalkyl, $C_3$-$C_8$cycloalkyl, $C_3$-$C_8$cycloalkyl where one carbon atom is replaced by O, S, S(O) or $SO_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or $SO_2$, or $C_3$-$C_8$cycloalkyl-$C_1$-$C_8$haloalkyl, $C_1$-$C_8$hydroxyalkyl, $C_1$-$C_8$alkoxy-$C_1$-$C_8$alkyl, $C_2$-$C_8$alkenyl, $C_2$-$C_8$haloalkenyl, $C_2$-$C_8$alkynyl, $C_2$-$C_8$haloalkynyl, phenyl, phenyl substituted by one to three $R^{10}$, heteroaryl, heteroaryl substituted by one to three $R^{10}$, phenyl-$C_1$-$C_4$alkyl, phenyl-$C_1$-$C_4$alkyl wherein the phenyl moiety is substituted by one to three $R^{10}$, heteroaryl-$C_1$-$C_4$alkyl or heteroaryl-$C_1$-$C_4$alkyl wherein the heteroaryl moiety is substituted by one to three $R^{10}$, or $C_1$-$C_4$alkyl-($C_1$-$C_4$alkyl-O—N=)C—$CH_2$—;
each $R^{10}$ is independently halogen, cyano, nitro, $C_1$-$C_8$alkyl, $C_1$-$C_8$haloalkyl, $C_1$-$C_8$alkoxy, or $C_1$-$C_8$haloalkoxy; or a salt or N-oxide thereof;

providing that when $B^1$—$B^2$—$B^3$—$B^4$ is —$CH_2$—C=CH—O— or —CH=C—$CH_2$—O—, $Y^1$—$Y^2$—$Y^3$—$Y^4$ is not —$CH_2$—O—N($R^a$)—C(=O)—, wherein $R^a$ is hydrogen, methyl, ethyl, propyl, isopropyl, butyl, cyclopropyl, cyclopropyl-methyl, cyclobutyl, cyclobutyl-methyl, oxetanyl, thietanyl, trifluoroethyl, difluoroethyl, allyl, propargyl, cyanomethyl, benzyl, benzyl substituted by one to three $R^b$, or $R^a$ is pyridyl-methyl- or pyridyl-methyl-substituted by one to three $R^b$; and each $R^b$ is independently fluoro, chloro, bromo, trifluoromethyl, trifluoromethoxy, cyano or methoxy.

Compounds wherein $B^1$—$B^2$—$B^3$—$B^4$ is —$CH_2$—C=CH—O— or —CH=C—$CH_2$—O— are disclosed in PCT/EP2011/051284.

The compounds of formula (I) may exist in different geometric or optical isomers or tautomeric forms. This invention covers all such isomers and tautomers and mixtures thereof in all proportions as well as isotopic forms such as deuterated compounds.

The compounds of the invention may contain one or more asymmetric carbon atoms, for example, in the —$CR^3R^4$— group or at the $LR^2Y^1Y^4$ carbon and may exist as enantiomers (or as pairs of diastereoisomers) or as mixtures of such. Further, where any Y group is SO, the compounds of the invention are sulfoxides, which can also exist in two enantiomeric forms.

Each alkyl moiety either alone or as part of a larger group (such as alkoxy, alkylcarbonyl, or alkoxycarbonyl) is a straight or branched chain and is, for example, methyl, ethyl, n-propyl, prop-2-yl, n-butyl, but-2-yl, 2-methyl-prop-1-yl or 2-methyl-prop-2-yl. The alkyl groups are preferably $C_1$-$C_6$ alkyl groups, more preferably $C_1$-$C_4$ and most preferably $C_1$-$C_3$ alkyl groups.

Alkenyl moieties can be in the form of straight or branched chains, and the alkenyl moieties, where appropriate, can be of either the (E)- or (Z)-configuration. Examples are vinyl and allyl. The alkenyl groups are preferably $C_2$-$C_6$, more preferably $C_2$-$C_4$ and most preferably $C_2$-$C_3$ alkenyl groups.

Alkynyl moieties can be in the form of straight or branched chains. Examples are ethynyl and propargyl. The alkynyl groups are preferably $C_2$-$C_6$, more preferably $C_2$-$C_4$ and most preferably $C_2$-$C_3$ alkynyl groups.

Halogen is fluorine, chlorine, bromine or iodine.

Haloalkyl groups (either alone or as part of a larger group, such as haloalkoxy) are alkyl groups which are substituted by one or more of the same or different halogen atoms and are, for example, trifluoromethyl, chlorodifluoromethyl, 2,2,2-trifluoro-ethyl or 2,2-difluoro-ethyl.

Haloalkenyl groups are alkenyl groups, respectively, which are substituted with one or more of the same or different halogen atoms and are, for example, 2,2-difluoro-vinyl or 1,2-dichloro-2-fluorovinyl.

Haloalkynyl groups are alkynyl groups, respectively, which are substituted with one or more of the same or different halogen atoms and are, for example, 1-chloro-prop-2-ynyl.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

The term "heteroaryl" refers to an aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of (5-6 membered) monocyclic groups include pyridyl, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, and thiadiazolyl. Examples of bicyclic groups include quinolinyl, cinnolinyl, quinoxalinyl, benzimidazolyl, benzothiophenyl, and benzothiadiazolyl. Monocyclic heteroaryl groups are preferred, preferably monocyclic rings containing 1 to 3 heterotoms selected from O, N or S, e.g. pyridyl, pyridazinyl, pyrimidinyl, pyrazinyl, pyrazolyl, furanyl, thiophenyl, oxazolyl, isoxazolyl, thiazolyl, preferably pyridyl, pyrazolyl, furanyl, thiophenyl, thiazolyl, pyridyl being most preferred.

The term "heterocyclyl" is defined to include heteroaryl and in addition their unsaturated or partially unsaturated analogues.

Preferred values of $A^1$, $A^2$, $A^3$, $A^4$, $G^1$, L, $R^1$, $R^2$, $R^3$, $R^4$, $Y^1$, $Y^2$, $Y^3$, $Y^4$, $R^5$, $R^6$, $R^7$, $R^8$, $R^9$ and $R^{10}$, are, in any combination, as set out below.

Preferably no more than two of $A^1$, $A^2$, $A^3$ and $A^4$ are nitrogen.

Preferably $A^1$ is C—H or C—$R^5$, most preferably $A^1$ is C—$R^5$.

Preferably $A^2$ is C—H or C—$R^5$, most preferably $A^2$ is C—H.

Preferably $A^3$ is C—H or N, most preferably $A^3$ is C—H.
Preferably $A^4$ is C—H or N, most preferably $A^4$ is C—H.
Preferably $G^1$ is oxygen.

Preferably L is a single bond or $C_1$-$C_4$alkylene. More preferably L is a single bond or $CH_2$, most preferably a single bond.

Preferably $R^1$ is hydrogen, $C_1$-$C_8$alkyl, $C_1$-$C_8$alkylcarbonyl-, $C_1$-$C_8$alkoxy, $C_1$-$C_8$alkoxy-$C_1$-$C_8$alkyl, phenyl or phenyl substituted by one to three $R^6$, or $R^1$ is heterocyclyl or heterocyclyl substituted by one to three $R^6$ or $C_1$-$C_8$alkoxycarbonyl-, wherein the heterocyclyl is selected from pyridyl, pyridazinyl, pyrimidinyl, pyrazinyl, pyrazolyl, furanyl, thiophenyl, oxazolyl, isoxazolyl or thiazolyl, more preferably pyridyl, pyrazolyl, furanyl, thiophenyl or thiazolyl, more preferably pyridinyl, pyridazinyl, pyrimidinyl or pyrazinyl, more preferably pyridinyl or pyrimidinyl. More preferably $R^1$ is hydrogen, methyl, ethyl, methylcarbonyl-, or methoxycarbonyl-, more preferably hydrogen, methyl or ethyl, even more preferably hydrogen or methyl, most preferably hydrogen.

Preferably $R^2$ is hydrogen or methyl, most preferably hydrogen.

Preferably $R^3$ is chlorodifluoromethyl or trifluoromethyl, most preferably trifluoromethyl.

Preferably $R^4$ is aryl or aryl substituted by one to three $R^6$, more preferably $R^4$ is phenyl or phenyl substituted by one to three $R^6$, even more preferably $R^4$ is phenyl substituted by one to three $R^6$, more preferably $R^4$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, more preferably 3,5-dichlorophenyl-, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-. In one group of compounds $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichlorophenyl, 3-trifluoromethyl-phenyl, 4-bromo-3,5-dichlorophenyl, 3-bromo-5-chlorophenyl, 4-fluoro-3,5-dichlorophenyl or 3,4,5-trichloro-phenyl. In another group of compounds $R^4$ is 3,5-dibromo-phenyl, 3,5-dichloro-phenyl, 3,5-bis-(trifluoromethyl)-phenyl, 4-bromo-3,5-dichlorophenyl, or 3,4,5-trichloro-phenyl, most preferably $R^4$ is 3,5-dichloro-phenyl. In another group of compounds $R^4$ is group A1

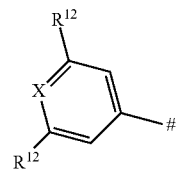

(A1)

wherein X is C—$R^{12}$ or nitrogen (preferably C—$R^{12}$) and each $R^{12}$ is independently hydrogen, halogen or trihalomethyl, wherein at least two $R^{12}$ are not hydrogen.

Preferably each $R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, or two $R^5$ on adjacent carbon atoms together form a —CH═CH—CH═CH— bridge, more preferably halogen, cyano, nitro, $C_1$-$C_8$alkyl, $C_2$-$C_8$ alkenyl, $C_3$-$C_8$cycloalkyl, $C_1$-$C_8$haloalkyl, even more preferably bromo, chloro, fluoro, cyano, nitro, methyl, ethyl, trifluoromethyl, cyclopropyl, vinyl, yet even more preferably bromo, chloro, fluoro, cyclopropyl, trifluoromethyl, vinyl, or methyl, most preferably chloro, bromo, fluoro, or methyl.

Preferably each $R^6$ is independently bromo, chloro, fluoro, cyano, nitro, methyl, ethyl, trifluoromethyl, methoxy, difluoromethoxy, trifluoromethoxy, more preferably chloro, fluoro, cyano, nitro, methyl, ethyl, trifluoromethyl, methoxy, or trifluoromethoxy, most preferably bromo, chloro, or trifluoromethyl.

Preferably $Y^1$ is $CR^7R^8$.

Preferably two of $Y^2$, $Y^3$ and $Y^4$ in the grouping —$Y^2$—$Y^3$—$Y^4$— together are —S—S—, —S—SO—, —SO—SO—, —SO—SO$_2$—, —SO$_2$—SO$_2$—, —O—N(—R$^9$)—, —O—S—, —O—SO—, —O—SO$_2$—, —N(—R$^9$)—N(—R$^9$)—, —N(—R$^9$)—S—, —N(—R$^9$)—S(O)— , or —N(—R$^9$)—SO$_2$—, more preferably —S—S—, —O—N(—R$^9$)—, —O—SO$_2$—, —N(—R$^9$)—N(—R$^9$)—, —N(—R$^9$)—S, —N(—R$^9$)—S(O)— or —N(—R$^9$)—SO$_2$.

The grouping —$Y^2$—$Y^3$—$Y^4$— may be selected from —C(R$^7$)(R$^8$)—N(—R$^9$)—N(—R$^9$)—, —C(R$^7$)(R$^8$)—N(—R$^9$)—O—, —C(R$^7$)(R$^8$)—N(—R$^9$)—S—, —C(R$^7$)(R$^8$)—N(—R$^9$)—SO—, —C(R$^7$)(R$^8$)—N(—R$^9$)—SO$_2$—, —C(R$^7$)(R$^8$)—O—N(—R$^9$)—, —C(R$^7$)(R$^8$)—O—S—, —C(R$^7$)(R$^8$)—O—SO—, —C(R$^7$)(R$^8$)—O—SO$_2$—, —C(R$^7$)(R$^8$)—S—N(—R$^9$)—, —C(R$^7$)(R$^8$)—S—O—, —C(R$^7$)(R$^8$)—S—S—, —C(R$^7$)(R$^8$)—S—SO—, —C(R$^7$)(R$^8$)—S—SO$_2$—, —C(R$^7$)(R$^8$)—SO—N(—R$^9$)—, —C(R$^7$)(R$^8$)—SO—O—, —C(R$^7$)(R$^8$)—SO—S—, —C(R$^7$)(R$^8$)—SO—SO—, —C(R$^7$)(R$^8$)—SO—SO$_2$—, —C(R$^7$)(R$^8$)—SO$_2$—N(—R$^9$)—, —C(R$^7$)(R$^8$)—SO$_2$—O—, —C(R$^7$)(R$^8$)—SO$_2$—S—, —C(R$^7$)(R$^8$)—SO$_2$—SO—, —C(R$^7$)(R$^8$)—SO$_2$—SO$_2$—, —C(=O)—N(—R$^9$)—N(—R$^9$)—, —C(=O)—N(—R$^9$)—O—, —C(=O)—N(—R$^9$)—S—, —C(=O)—N(—R$^9$)—SO—, —C(=O)—N(—R$^9$)—SO$_2$—, —C(=O)—O—N(—R$^9$)—, —C(=O)—O—S—, —C(=O)—O—SO—, —C(=O)—O—SO$_2$—, —C(=O)—S—N(—R$^9$)—, —C(=O)—S—O—, —C(=O)—S—S—, —C(=O)—S—SO—, —C(=O)—S—SO$_2$—, —N(—R$^9$)—N(—R$^9$)—C(R$^7$)(R$^8$), —N(—R$^9$)—N(—R$^9$)—C(=O), —N(—R$^9$)—N(—R$^9$)—S—, —N(—R$^9$)—N(—R$^9$)—SO—, —N(—R$^9$)—N(—R$^9$)—SO$_2$—, —N(—R$^9$)—O—C(R$^7$)(R$^8$), —N(—R$^9$)—O—C(=O)—, —N(—R$^9$)—O—N(—R$^9$)—, —N(—R$^9$)—O—S—, —N(—R$^9$)—O—SO—, —N(—R$^9$)—O—SO$_2$—, —N(—R$^9$)—S—C(R$^7$)(R$^8$), —N(—R$^9$)—S—C(=O)—, —N(—R$^9$)—S—N(—R$^9$)—, —N(—R$^9$)—S—O—, —N(—R$^9$)—S—S—, —N(—R$^9$)—S—SO—, —N(—R$^9$)—S—SO$_2$—, —N(—R$^9$)—SO—C(R$^7$)(R$^8$), —N(—R$^9$)—SO—N(—R$^9$)—, —N(—R$^9$)—SO—O—, —N(—R$^9$)—SO—S—, —N(—R$^9$)—SO$_2$—C(R$^7$)(R$^8$), —N(—R$^9$)—SO$_2$—N(—R$^9$)—, —N(—R$^9$)—SO$_2$—O—, —N(—R$^9$)—SO$_2$—S—, —O—N(—R$^9$)—C(R$^7$)(R$^8$)—, —O—N(—R$^9$)—C(=O)—, —O—N(—R$^9$)—S—, —O—N(—R$^9$)—SO—, —O—N(—R$^9$)—SO$_2$—, —N(—R$^9$)—O—N(—R$^9$)—, —N(—R$^9$)—O—S—, —N(—R$^9$)—O—SO—, —N(—R$^9$)—O—SO$_2$—, —N(—R$^9$)—S—C(R$^7$)(R$^8$)—, —N(—R$^9$)—S—C(=O)—, —N(—R$^9$)—S—N(—R$^9$)—, —N(—R$^9$)—S—O—, —N(—R$^9$)—S—S—, —N(—R$^9$)—S—SO—, —N(—R$^9$)—S—SO$_2$—, —N(—R$^9$)—SO—C(R$^7$)(R$^8$)—, —N(—R$^9$)—SO—N(—R$^9$)—, —N(—R$^9$)—SO—O—, —N(—R$^9$)—SO—S—, —N(—R$^9$)—SO$_2$—C(R$^7$)(R$^8$)—, —N(—R$^9$)—SO$_2$—N(—R$^9$)—, —N(—R$^9$)—SO$_2$—O—, —N(—R$^9$)—SO$_2$—S—, —S—N(—R$^9$)—C(R$^7$)(R$^8$)—, —S—N(—R$^9$)—C(=O)—, —S—N(—R$^9$)—N(—R$^9$)—, —S—N(—R$^9$)—O—, —S—N(—R$^9$)—S—, —S—N(—R$^9$)—SO—, —S—N(—R$^9$)—SO$_2$—, —S—O—C(R$^7$)(R$^8$)—, —S—O—C(=O)—, —S—O—N(—R$^9$)—, —S—S—C(R$^7$)(R$^8$)—, —S—S—C(=O)—, —S—S—S—, —S—SO—C(R$^7$)(R$^8$)—, —S—SO—C(=O)—, —S—SO$_2$—C(R$^7$)(R$^8$)—, —S—SO$_2$—C(=O)—, —SO—N(—R$^9$)—C(R$^7$)(R$^8$)—, —SO—N(—R$^9$)—C(=O)—, —SO—N(—R$^9$)—N(—R$^9$)—, —SO—N(—R$^9$)—O—, —SO—N(—R$^9$)—S—, —SO—N(—R$^9$)—SO—, —SO—N(—R$^9$)—SO$_2$—, —SO—O—C(R$^7$)(R$^8$)—, —SO—O—C(=O)—, —SO—S—C(R$^7$)(R$^8$)—, —SO—S—C(=O)—, —SO$_2$—S—N(—R$^9$)—, —SO$_2$—N(—R$^9$)—C(R$^7$)(R$^8$)—, —SO$_2$—N(—R$^9$)—C(=O)—, —SO$_2$—N(—R$^9$)—N(—R$^9$)—, —SO$_2$—N(—R$^9$)—O—, —SO$_2$—N(—R$^9$)—S—, —SO$_2$—N(—R$^9$)—SO$_2$—, —SO$_2$—O—C(R$^7$)(R$^8$)— and —SO$_2$—O—C(=O)—.

Preferably the grouping —$Y^2$—$Y^3$—$Y^4$— is selected from —C(R$^7$)(R$^8$)—N(—R$^9$)—N(—R$^9$)—, —C(R$^7$)(R$^8$)—N(—R$^9$)—O—, —C(R$^7$)(R$^8$)—N(—R$^9$)—S—, —C(R$^7$)(R$^8$)—N(—R$^9$)—SO$_2$—, —C(R$^7$)(R$^8$)—O—N(—R$^9$)—, —C(R$^7$)(R$^8$)—O—SO—, —C(R$^7$)(R$^8$)—O—SO$_2$—, —C(R$^7$)(R$^8$)—S—N(—R$^9$)—, —C(R$^7$)(R$^8$)—S—S—, —C(R$^7$)(R$^8$)—SO—O—, —C(R$^7$)(R$^8$)—SO$_2$—N(—R$^9$)—, —C(R$^7$)(R$^8$)—SO$_2$—O—, —C(=O)—N(—R$^9$)—N(—R$^9$)—, —C(=O)—N(—R$^9$)—O—, —C(=O)—N(—R$^9$)—S—, —C(=O)—O—N(—R$^9$)—, —C(=O)—S—N(—R$^9$)—, —N(—R$^9$)—N(—R$^9$)—C(R$^7$)(R$^8$)—, —N(R$^9$)—N(—R$^9$)—C(=O)—, —N(—R$^9$)—O—C(R$^7$)(R$^8$)—, —N(—R$^9$)—O—C(=O)—, —N(—R$^9$)—S—C(R$^7$)(R$^8$)—, —N(—R$^9$)—SO—N(—R$^9$)—, —N(—R$^9$)—SO$_2$—C(R$^7$)(R$^8$)—, —N(—R$^9$)—SO$_2$—N(—R$^9$)—, —N(—R$^9$)—SO$_2$—O—, —O—N(—R$^9$)—C(R$^7$)(R$^8$)—, —O—N(—R$^9$)—C(=O)—, —O—N(—R$^9$)—SO—, —O—N(—R$^9$)—SO$_2$—, —N(—R$^9$)—S—C(R$^7$)(R$^8$)—, —N(—R$^9$)—SO—C(R$^7$)(R$^8$)—, —N(—R$^9$)—SO—N(—R$^9$)—, —N(—R$^9$)—SO—O—, —N(—R$^9$)—SO$_2$—C(R$^7$)(R$^8$)—, —N(—R$^9$)—SO$_2$—N(—R$^9$)—, —N(—R$^9$)—SO$_2$—O—, —S—N(—R$^9$)—C(R$^7$)(R$^8$)—, —S—N(—R$^9$)—C(=O)—, —S—S—C(R$^7$)(R$^8$)—, —SO—N(—R$^9$)—N(—R$^9$)—, —SO—O—C(R$^7$)(R$^8$)—, —SO$_2$—N(—R$^9$)—C(R$^7$)(R$^8$)—, —SO$_2$—N(—R$^9$)—N(—R$^9$)—, —SO$_2$—N(—R$^9$)—O— and —SO$_2$—O—C(R$^7$)(R$^8$)—. More preferably the grouping —$Y^2$—$Y^3$—$Y^4$— is selected from —O—N(—R$^9$)—C(=O)—, —S—S—C(R$^7$)(R$^8$)—, —S—SO—C(R$^7$)(R$^8$)—, —O—N(—R$^9$)—(R$^7$)(R$^8$)—, —N(—R$^9$)—N(—R$^9$)—C(=O)—, —SO$_2$—N(—R$^9$)—C(R$^7$)(R$^8$)—, —C(R$^7$)(R$^8$)—N(—R$^9$)—O—, —C(R$^7$)(R$^8$)—N(—R$^9$)—O—, —C(=O)—N(—R$^9$)—O—, —C(=O)—N(R$^9$)—O—, —O—SO—O—, —C(R$^7$)(R$^8$)—N(—R$^9$)—SO$_2$, —N(—R$^9$)—SO$_2$—O—, —SO—O—C(R$^7$)(R$^8$)— and —N(—R$^9$)—SO—O—, even more preferably from —O—N(—R$^9$)—C(=O)—, —S—S—C(R$^7$)(R$^8$)—, —SO$_2$—N(—R$^9$)—C(R$^7$)(R$^8$)—, —C(R$^7$)(R$^8$)—N(—R$^9$)—O—, —C(=O)—N(—R$^9$)—O—, —SO—O—C(R$^7$)(R$^8$)— and —C(=O)—N(—R$^9$)—O—, even more preferably —O—N(—R$^9$)—C(=O)— and —SO—O—C(R$^7$)(R$^8$)—.

In one embodiment $Y^2$ or $Y^4$ is $CR^7R^8$ or $C=O$. According to this embodiment the grouping —$Y^2$—$Y^3$—$Y^4$— is preferably selected from —C(R$^7$)(R$^8$)—N(—R$^9$)—N(—R$^9$)—, —C(R$^7$)(R$^8$)—N(—R$^9$)—O—, —C(R$^7$)(R$^8$)—N(—R$^9$)—S—, —C(R$^7$)(R$^8$)—N(—R$^9$)—SO$_2$—, —C(R$^7$)(R$^8$)—O—N(—R$^9$)—, —C(R$^7$)(R$^8$)—O—SO—, —C(R$^7$)(R$^8$)—O—SO$_2$—, —C(R$^7$)(R$^8$)—S—N(—R$^9$)—, —C(R$^7$)(R$^8$)—S—S—, —C(R$^7$)(R$^8$)—SO—O—, —C(R$^7$)(R$^8$)—SO$_2$—N(—R$^9$)—, —C(R$^7$)(R$^8$)—SO$_2$—O—, —C(=O)—N(—R$^9$)—N(—R$^9$)—, —C(=O)—N(—R$^9$)—O—, —C(=O)—N(—R$^9$)—S—, —C(=O)—O—N(—R$^9$)—, —C(=O)—S—N(—R$^9$)—, —N(—R$^9$—N(—R$^9$)—C(R$^7$)(R$^8$)—, —N(—R$^9$)—N(—R$^9$)—C(=O)—, —N(—R$^9$)—O—C(R$^7$)(R$^8$)—, —N(—R$^9$)—O—C(=O)—, —N(—R$^9$)—S—C(R$^7$)(R$^8$)—, —N(—R$^9$)—SO$_2$—C(R$^7$)(R$^8$)—, —O—N(—R$^9$)—C(R$^7$)(R$^8$)—, —O—N(—R$^9$)—C(=O)—, —N(—R$^9$)—S—C(R$^7$)(R$^8$)—, —N(—R$^9$)—SO—C(R$^7$)(R$^8$)—, —S—N(—R$^9$)—C(R$^7$)(R$^8$)—, —S—N(—R$^9$)—C(=O), —S—S—C(R$^7$)(R$^8$)—, —SO—O—C(R$^7$)(R$^8$)—, —SO$_2$—N(—R$^9$)—C(R$^7$)(R$^8$)—, and —SO$_2$—O—C(R$^7$)(R$^8$)—.
More preferably the grouping —$Y^2$—$Y^3$—$Y^4$— is selected from —S—S—C(R$^7$)(R$^8$)—, —O—N(—R$^9$)—C(=O)—, —C(=O)—N(—R$^9$)—O—, —C(R$^7$)(R$^8$)—N(—R$^9$)—O—, —C(R$^7$)(R$^8$)—S—S—, —O—N(—R$^9$)—C(R$^7$)(R$^8$)—, —N(—R$^9$)—O—C(R$^7$)(R$^8$)—, —SO—O—C(R$^7$)(R$^8$)— and —C(R$^7$)(R$^8$)—N(—R$^9$)—O—. More preferably the grouping —Y$^2$—Y$^3$—Y$^4$— is selected from —S—S—C(R$^7$)(R$^8$)—, —O—N(—R$^9$)—C(=O)—, —C(=O)—N(—R$^9$)—O—, —SO—O—C(R$^7$)(R$^8$)— and —C(R$^7$)(R$^8$)—N(—R$^9$)—O—. More preferably the grouping —Y$^2$—Y$^3$—Y$^4$— is —O—N(—R$^9$)—C(=O)— or —SO—O—C(R$^7$)(R$^8$)—.

In one embodiment Y$^2$ or Y$^4$ is C=O. According to this embodiment the grouping —Y$^2$—Y$^3$—Y$^4$— is preferably selected from —C(=O)—N(—R$^9$)—N(—R$^9$)—, —C(=O)—N(—R$^9$)—O—, —C(=O)—N(—R$^9$)—S—, —C(=O)—O—N(—R$^9$)—, —C(=O)—S—N(—R$^9$)—, —N(—R$^9$)—N(—R$^9$)—C(=O)—, —N(—R$^9$)—O—C(=O)—, —O—N(—R$^9$)—C(=O)— and —S—N(—R$^9$)—C(=O). More preferably the grouping —Y$^2$—Y$^3$—Y$^4$— is selected from —O—N(—R$^9$)—C(=O)— and —C(=O)—N(—R$^9$)—O—.

In one embodiment Y$^2$ or Y$^4$ is CR$^7$R$^8$. According to this embodiment the grouping —Y$^2$—Y$^3$—Y$^4$— is preferably selected from —C(R$^7$)(R$^8$)—N(—R$^9$)—N(—R$^9$)—, —C(R$^7$)(R$^8$)—N(—R$^9$)—O—, —C(R$^7$)(R$^8$)—N(—R$^9$)—S—, —C(R$^7$)(R$^8$)—N(—R$^9$)—SO$_2$—, —C(R$^7$)(R$^8$)—O—N(—R$^9$)—, —C(R$^7$)(R$^8$)—O—SO—, —C(R$^7$)(R$^8$)—O—SO$_2$—, —C(R$^7$)(R$^8$)—S—N(—R$^9$)—, —C(R$^7$)(R$^8$)—S—S—, —C(R$^7$)(R$^8$)—SO—O—, —C(R$^7$)(R$^8$)—SO$_2$—N(—R$^9$)—, —C(R$^7$)(R$^8$)—SO$_2$—O—, —N(—R$^9$)—N(—R$^9$)—C(R$^7$)(R$^8$)—, —N(—R$^9$)—O—C(R$^7$)(R$^8$)—, —N(—R$^9$)—S—C(R$^7$)(R$^8$)—, —N(—R$^9$)—SO$_2$—C(R$^7$)(R$^8$)—, —O—N(—R$^9$)—C(R$^7$)(R$^8$)—, —N(—R$^9$)—S—C(R$^7$)(R$^8$)—, —N(—R$^9$)—SO—C(R$^7$)(R$^8$)—, —N(—R$^9$)—SO$_2$—C(R$^7$)(R$^8$)—, —S—N(—R$^9$)—C(R$^7$)(R$^8$), —S—S—C(R$^7$)(R$^8$)—, —SO—O—C(R$^7$)(R$^8$)—, —SO$_2$—N(—R$^9$)—C(R$^7$)(R$^8$)— and —SO$_2$—O—C(R$^7$)(R$^8$)—. More preferably the grouping —Y$^2$—Y$^3$—Y$^4$— is selected from —S—S—C(R$^7$)(R$^8$)—, —C(R$^7$)(R$^8$)—N(—R$^9$)—O—, —C(R$^7$)(R$^8$)—S—S—, —O—N(—R$^9$)—C(R$^7$)(R$^8$)—, —N(—R$^9$)—O—C(R$^7$)(R$^8$)—, —SO—O—C(R$^7$)(R$^8$)— and —C(R$^7$)(R$^8$)—N(—R$^9$)—O—. More preferably the grouping Y$^2$—Y$^3$—Y$^4$— is selected from —S—S—C(R$^7$)(R$^8$)—, —SO—O—C(R$^7$)(R$^8$)— and —C(R$^7$)(R$^8$)—N(—R$^9$)—O—.

In one embodiment Y$^2$ and Y$^4$ are independently N—R$^9$, O, S, SO or SO$_2$. According to this embodiment the grouping —Y$^2$—Y$^3$—Y$^4$— is preferably selected from —N(—R$^9$)—SO—N(—R$^9$)—, —N(—R$^9$)—SO$_2$—N(—R$^9$)—, —N(—R$^9$)—SO$_2$—O—, —O—N(—R$^9$)—SO—, —O—N(—R$^9$)—SO$_2$—, —N(—R$^9$)—SO—N(—R$^9$)—, —N(—R$^9$)—SO—O—, —N(—R$^9$)—SO$_2$—N(—R$^9$)—, —N(—R$^9$)—SO$_2$—O—, —SO—N(—R$^9$)—N(—R$^9$)—, —SO$_2$—N(—R$^9$)—N(—R$^9$)— and —SO$_2$—N(—R$^9$)—O—. More preferably the grouping Y$^2$—Y$^3$—Y$^4$— is selected from —N(—R$^9$)—SO$_2$—O—, —O—SO$_2$—O—, —N(—R$^9$)—SO$_2$—N(—R$^9$)—, —O—SO$_2$—N(—R$^9$)— and —N(—R$^9$)—SO$_2$—O—. More preferably the grouping —Y$^2$—Y$^3$—Y$^4$— is selected from —N(—R$^9$)—SO$_2$—O—, —O—SO$_2$—O—, —N(—R$^9$)—SO$_2$—N(—R$^9$)—, and —O—SO$_2$—N(—R$^9$)—.

In one embodiment Y$^1$ is CR$^7$R$^8$ or C=O; Y$^2$ and Y$^3$ are independently CR$^7$R$^8$, C=O, N—R$^9$, O, S, SO or SO$_2$; Y$^4$ is CR$^7$R$^8$, C=O, SO or SO$_2$. Preferably Y$^2$ and Y$^3$ are independently N—R$^9$, O, S, SO, SO$_2$. Preferably Y$^2$ and Y$^3$ are independently N—R$^9$, O or S. Preferably Y$^2$ is O or S. More preferably Y$^2$ is O. Preferably Y$^3$ is N—R$^9$. Preferably Y$^4$ is C=O. Preferably Y$^3$ is N—R$^9$ and Y$^4$ is C=O. Preferably Y$^2$ is O, Y$^3$ is N—R$^9$ and Y$^4$ is C=O. Preferably Y$^1$ is CR$^7$R$^8$, Y$^2$ is O, Y$^3$ is N—R$^9$ and Y$^4$ is C=O.

In one embodiment Y$^1$ is CR$^7$R$^8$, Y$^2$ and Y$^3$ are independently N—R$^9$, O, S, SO or SO$_2$ and Y$^4$ is CR$^7$R$^8$, C=O, SO or SO$_2$.

In one embodiment Y$^1$ is CR$^7$R$^8$, Y$^2$ is N—R$^9$, O, S, SO or SO$_2$, Y$^3$ is N—R$^9$, and Y$^4$ is CR$^7$R$^8$, C=O, SO or SO$_2$, preferably Y$^1$ is CR$^7$R$^8$, Y$^2$ is O or S, Y$^3$ is N—R$^9$, and Y$^4$ is C=O, preferably Y$^1$ is CR$^7$R$^8$, Y$^2$ is O, Y$^3$ is N—R$^9$, and Y$^4$ is C=O.

In one embodiment Y$^1$ is CR$^7$R$^8$, Y$^2$ is N—R$^9$, O, S, SO or SO$_2$, Y$^3$ is O or S, Y$^4$ is C=O, SO, or SO$_2$.

In one embodiment Y$^1$ is C=O, Y$^2$ is N—R$^9$ or O, Y$^3$ is N—R$^9$, Y$^4$ is C=O, SO, or SO$_2$.

In one embodiment Y$^1$ is CR$^7$R$^8$, C=O, Y$^2$ is CR$^7$R$^8$, C=O, Y$^3$ is N—R$^9$, O or S, and Y$^4$ is SO, or SO$_2$.

Preferably Y$^4$ is CR$^7$R$^8$ or C=O when L is a bond, e.g. the grouping —Y$^2$—Y$^3$—Y$^4$— is —S—S—C(R$^7$)(R$^8$)—, —SO—O—C(R$^7$)(R$^8$)— or —O—N(—R$^9$)—C(=O)—, more preferably —SO—O—C(R$^7$)(R$^8$)— or —O—N(—R$^9$)—C(=O)—.

Preferably when Y$^4$ is a heteroatom, L is C$_1$-C$_4$alkylene.
Preferably when Y$^4$ is NR$^9$, L is C$_1$-C$_4$alkylene, in which case Y$^3$ is preferably NR$^9$, O, S, SO or SO$_2$.
Preferably when Y$^4$ is O, L is C$_1$-C$_4$alkylene, in which case Y$^3$ is preferably NR$^9$.

In one embodiment L is a bond, Y$^1$ is CR$^7$R$^8$, Y$^2$ is O, Y$^3$ is N—R$^9$ and Y$^4$ is C=O.

In one embodiment —Y$^2$—Y$^3$—Y$^4$— is C(=O)—N(—R$^9$)—N(—R$^9$)—, —C(=O)—N(—R$^9$)—O—, —C(=O)—N(—R$^9$)—S—, —C(=O)—O—N(—R$^9$)—, —C(=O)—S—N(—R$^9$)—, —N(—R$^9$)—N(—R$^9$)—C(=O)—, —N(—R$^9$)—O—C(=O)—, —O—N(—R$^9$)—C(=O)—, —S—N(—R$^9$)—C(=O), —C(=S)—N(—R$^9$)—N(—R$^9$)—, —C(=S)—N(—R$^9$)—O—, —C(=S)—N(—R$^9$)—S—, —C(=S)—O—N(—R$^9$)—, —C(=S)—S—N(—R$^9$)—, —N(—R$^9$)—N(—R$^9$)—C(=S)—, —N(—R$^9$)—O—C(=S)—, —O—N(—R$^9$)—C(=S)— or —S—N(—R$^9$)—C(=S).

In one embodiment Y$^1$ is CR$^7$R$^8$, Y$^2$ is O, Y$^3$ is N—R$^9$ and Y$^4$ is C=O or C=S.

In all embodiments at least two adjacent ring atoms in the ring formed by Y$^1$, Y$^2$, Y$^3$ and Y$^4$ are heteroatoms. Preferably the ring formed by Y$^1$, Y$^2$, Y$^3$ and Y$^4$ does not contain two adjacent oxygen atoms. In some cases there may be no more than one oxygen ring atom in the ring formed by Y$^1$, Y$^2$, Y$^3$ and Y$^4$. Embodiments providing Y$^1$, Y$^2$, Y$^3$, Y$^4$ values may be combined with any of the values, including preferred values, of A$^1$, A$^2$, A$^3$, A$^4$, G$^1$, L, R$^1$, R$^2$, R$^3$, R$^4$, R$^5$, R$^6$, R$^7$, R$^8$, R$^9$ and R$^{10}$.

Preferably each R$^7$ is independently hydrogen, or C$_1$-C$_8$alkyl, most preferably hydrogen.
Preferably each R$^8$ is independently hydrogen, or C$_1$-C$_8$alkyl, most preferably hydrogen.
Preferably R$^7$ and R$^8$ are both hydrogen.
Preferably each R$^9$ is independently hydrogen, cyano-C$_1$-C$_8$alkyl, C$_1$-C$_8$alkyl, C$_3$-C$_8$cycloalkyl, C$_3$-C$_8$cycloalkyl where one carbon atom in the cycloalkyl group is replaced by O, S, S(O) or SO$_2$, or C$_3$-C$_8$cycloalkyl-C$_1$-C$_8$alkyl, C$_3$-C$_8$cycloalkyl-C$_1$-C$_8$alkyl where one carbon atom in the cycloalkyl group is replaced by O, S, S(O) or SO$_2$, or C$_1$-C$_8$haloalkyl, C$_1$-C$_8$hydroxyalkyl, C$_1$-C$_8$hydroxyalkyl, C$_2$-C$_8$alkenyl, C$_2$-C$_8$alkynyl, phenyl-C$_1$-C$_4$alkyl or phenyl-C$_1$-C$_4$alkyl wherein the phenyl moiety is substituted by one to three R$^{10}$, 5-6 membered heteroaryl-C$_1$-C$_4$alkyl or 5-6 membered heteroaryl-$C_1$-$C_4$alkyl wherein the heteroaryl moiety is substituted by one to three $R^{10}$; more preferably each $R^9$ is independently hydrogen, cyano-$C_1$-$C_8$alkyl-, $C_1$-$C_8$alkyl, $C_3$-$C_8$cycloalkyl, $C_3$-$C_8$cycloalkyl where one carbon atom in the cycloalkyl group is replaced by O, S, S(O) or $SO_2$, or $C_1$-$C_8$haloalkyl, $C_1$-$C_8$hydroxyalkyl, $C_2$-$C_8$alkenyl, $C_2$-$C_8$alkynyl, phenyl-$C_1$-$C_4$alkyl or phenyl-$C_1$-$C_4$alkyl wherein the phenyl moiety is substituted by one to three $R^{10}$, 5-6 membered heteroaryl-$C_1$-$C_4$alkyl or 5-6 membered heteroaryl-$C_1$-$C_4$alkyl wherein the heteroaryl moiety is substituted by one to three $R^{10}$; even more preferably each $R^9$ is independently hydrogen, cyano-$C_1$-$C_6$alkyl, $C_1$-$C_6$alkyl, $C_3$-$C_6$cycloalkyl, $C_3$-$C_6$cycloalkyl where one carbon atom in the cycloalkyl group is replaced by O, S, S(O) or $SO_2$, or $C_1$-$C_6$haloalkyl, $C_1$-$C_6$hydroxyalkyl, $C_1$-$C_6$alkoxy-$C_1$-$C_6$alkyl, $C_2$-$C_6$alkenyl, $C_2$-$C_6$alkynyl, phenyl-$CH_2$-alkyl or phenyl-$CH_2$— wherein the phenyl moiety is substituted by one to three $R^{10}$, furanyl or furanyl substituted by one to three $R^{10}$, triazolyl or triazolyl optionally substituted by one to three $R^{10}$; yet even more preferably each $R^9$ is independently hydrogen, $C_1$-$C_4$alkyl, $C_3$-$C_6$cycloalkyl, $C_1$-$C_4$haloalkyl, $C_1$-$C_4$hydroxyalkyl, $C_1$-$C_4$alkoxy-$C_1$-$C_4$alkyl, phenyl-$CH_2$-alkyl- or phenyl-$CH_2$— wherein the phenyl moiety is substituted by one to three $R^{10}$, furanyl or furanyl substituted by one to three $R^{10}$, thietanyl, oxetanyl, oxo-thietanyl, or dioxo-thietanyl; yet even more preferably each $R^9$ is independently methyl, ethyl, cyclopropyl, cyclobutyl, oxetanyl, thietanyl, trifluoroethyl, difluoroethyl, allyl, propargyl, cyanomethyl, benzyl, benzyl substituted by one to three $R^{10}$ or pyridine-methyl- or pyridine-methyl-substituted by one to three $R^{10}$. Ethyl and trifluoroethyl are particularly preferred. Heteroaryl preferably refers to pyridyl, pyridazinyl, pyrimidinyl, pyrazinyl, pyrazolyl, furanyl, thiophenyl, oxazolyl, isoxazolyl or thiazolyl, more preferably pyridyl, pyrazolyl, furanyl, thiophenyl or thiazolyl, most preferably pyridyl.

Preferably each $R^{10}$ is independently halogen, cyano, $C_1$-$C_8$haloalkyl, $C_1$-$C_8$alkoxy or $C_1$-$C_8$haloalkoxy, most preferably, fluoro, chloro, bromo, trifluoromethyl, trifluoromethoxy, cyano or methoxy.

In one embodiment the invention provides compounds of formula IA

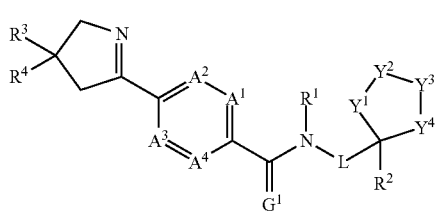

(IA)

wherein $A^1$, $A^2$, $A^3$, $A^4$, $G^1$, L, $Y^1$, $Y^2$, $Y^3$, $Y^4$, $R^1$, $R^2$, $R^3$, $R^4$ and their preferred values are as defined for a compound of formula (I); or a salt or N-oxide thereof.

In a further embodiment the invention provides compounds of formula IB

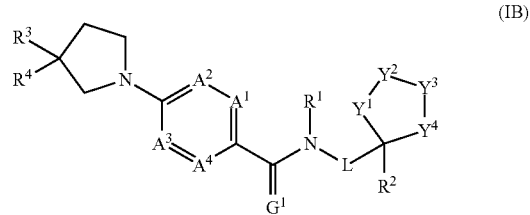

(IB)

wherein $A^1$, $A^2$, $A^3$, $A^4$, $G^1$, L, $Y^1$, $Y^2$, $Y^3$, $Y^4$, $R^1$, $R^2$, $R^3$, $R^4$ and their preferred values are as defined for a compound of formula (I); or a salt or N-oxide thereof.

In a further embodiment the invention provides compounds of formula IC

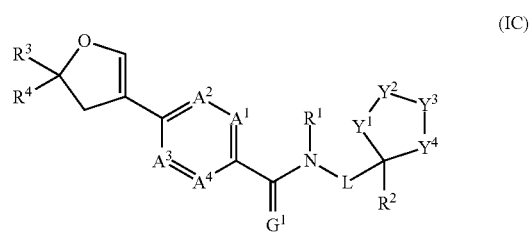

(IC)

wherein $A^1$, $A^2$, $A^3$, $A^4$, $G^1$, L, $Y^1$, $Y^2$, $Y^3$, $Y^4$, $R^1$, $R^2$, $R^3$, $R^4$ and their preferred values are as defined for a compound of formula (I); or a salt or N-oxide thereof, providing that providing that $Y^1$—$Y^2$—$Y^3$—$Y^4$ is not —$CH_2$—O—N($R^a$)—C(=O)—, wherein $R^a$ is hydrogen, methyl, ethyl, propyl, isopropyl, butyl, cyclopropyl, cyclopropyl-methyl, cyclobutyl, cyclobutyl-methyl, oxetanyl, thietanyl, trifluoroethyl, difluoroethyl, allyl, propargyl, cyanomethyl, benzyl, benzyl substituted by one to three $R^b$, or $R^a$ is pyridyl-methyl- or pyridyl-methyl-substituted by one to three $R^b$; and each $R^b$ is independently fluoro, chloro, bromo, trifluoromethyl, trifluoromethoxy, cyano or methoxy.

In a further embodiment the invention provides compounds of formula ID

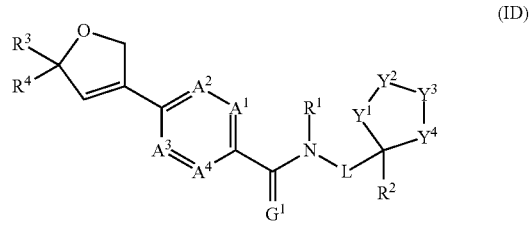

(ID)

wherein $A^1$, $A^2$, $A^3$, $A^4$, $G^1$, $Y^1$, $Y^2$, $Y^3$, $Y^4$, L, $R^1$, $R^2$, $R^3$, $R^4$ and their preferred values are as defined for a compound of formula (I); or a salt or N-oxide thereof, providing that providing that $Y^1$—$Y^2$—$Y^3$—$Y^4$ is not —$CH_2$—O—N($R^a$)—C(=O)—, wherein $R^a$ is hydrogen, methyl, ethyl, propyl, isopropyl, butyl, cyclopropyl, cyclopropyl-methyl, cyclobutyl, cyclobutyl-methyl, oxetanyl, thietanyl, trifluoroethyl, difluoroethyl, allyl, propargyl, cyanomethyl, benzyl, benzyl substituted by one to three $R^b$, or $R^a$ is pyridyl-methyl- or pyridyl-methyl-substituted by one to three $R^b$; and each $R^b$ is independently fluoro, chloro, bromo, trifluoromethyl, trifluoromethoxy, cyano or methoxy.

A preferred embodiment provides compounds of formula (Ia.A) wherein $A^1$ is C—$R^5$, $A^2$, $A^3$, and $A^4$ are C—H, $R^4$ is 3,5-dichloro-phenyl, L is a bond, and $G^1$, $R^1$, $R^2$, $R^3$, $R^4$, $Y^1$, $Y^2$, $Y^3$ and $Y^4$ are as defined for a compound of formula (I); or a salt or N-oxide thereof.

A preferred embodiment provides compounds of formula (Ia.B) wherein $A^1$ is C-Me, $A^2$, $A^3$, and $A^4$ are C—H, $R^4$ is 3,5-dichloro-phenyl, L is a bond, and $G^1$, $R^1$, $R^2$, $R^3$, $Y^1$, $Y^2$, $Y^3$ and $Y^4$ are as defined for a compound of formula (I); or a salt or N-oxide thereof.

A preferred embodiment provides compounds of formula (Ia.C)

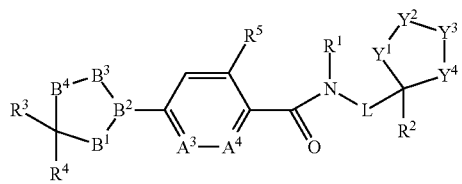

(Ia.C)

wherein $R^2$ is hydrogen or $C_1$-$C_4$ alkyl;

$R^3$ is $C_1$-$C_4$ haloalkyl;

$R^4$ is phenyl, or phenyl substituted by one to three $R^6$;

$R^5$ is halogen, nitro, $C_1$-$C_4$alkyl, $C_3$-$C_4$cycloalkyl, $C_2$-$C_4$alkenyl or $C_1$-$C_4$haloalkyl;

$A^3$ and $A^4$ are independently C—H or N;

L is a bond or methylene;

$B^1$, $B^2$, $B^3$, $B^4$, $R^1$, $R^6$, $Y^1$, $Y^2$, $Y^3$, and $Y^4$ are as defined for formula (I);

wherein at least two adjacent ring atoms in the ring formed by $Y^1$, $Y^2$, $Y^3$ and $Y^4$ are heteroatoms; or a salt or N-oxide thereof. Preferred values of $Y^1$, $Y^2$, $Y^3$, $Y^4$, $A^3$, $A^4$, $R^1$, $R^2$, $R^3$, $R^4$, $R^5$ and $R^6$ are as defined for formula I.

A preferred embodiment provides compounds of formula (Ia.D)

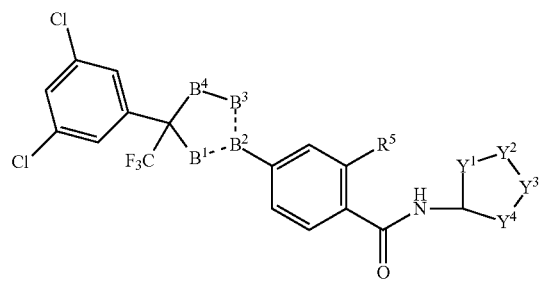

(Ia.D)

wherein $R^5$, $B^1$, $B^2$, $B^3$, $B^4$, $Y^1$, $Y^2$, $Y^3$, $Y^4$ and their preferred values are as defined for formula (I); wherein at least two adjacent ring atoms in the ring formed by $Y^1$, $Y^2$, $Y^3$ and $Y^4$ are heteroatoms; or a salt or N-oxide thereof.

A further preferred embodiment provides compounds of formula (Ia.E)

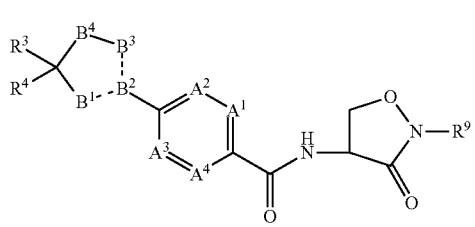

(Ia.E)

wherein $B^1$—$B^2$—$B^3$—$B^4$ is —$CH_2$—C=N—$CH_2$— or —$CH_2$—N—$CH_2$—$CH_2$—, and $A^1$, $A^2$, $A^3$, $A^4$, $R^3$, $R^4$ and $R^9$ and their preferred values are as defined for a compound of formula (I); or a salt or N-oxide thereof.

In one embodiment the invention provides compounds of formula Ia.E1

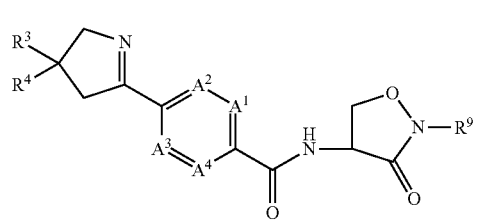

(Ia.E1)

wherein $A^1$, $A^2$, $A^3$, $A^4$, $R^3$, $R^4$ and $R^9$ and their preferred values are as defined for a compound of formula (I); or a salt or N-oxide thereof.

In one embodiment the invention provides compounds of formula Ia.E2

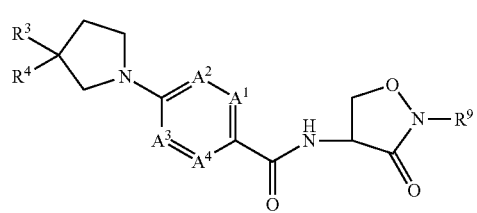

(Ia.E2)

wherein $A^1$, $A^2$, $A^3$, $A^4$, $R^3$, $R^4$ and $R^9$ and their preferred values are as defined for a compound of formula (I); or a salt or N-oxide thereof.

A further preferred embodiment provides compounds of formula (Ia.F)

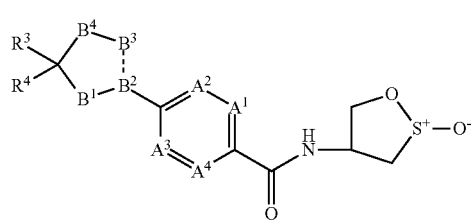

(Ia.F)

wherein $B^1$—$B^2$—$B^3$—$B^4$ is —$CH_2$—C=N—$CH_2$—, —$CH_2$—N—$CH_2$—$CH_2$—, —$CH_2$—C=CH—O— or —CH=C—$CH_2$—O—; and $A^1$, $A^2$, $A^3$, $A^4$, $R^3$ and $R^4$ and their preferred values are as defined for a compound of formula (I); or a salt or N-oxide thereof.

In one embodiment the invention provides compounds of formula Ia.F1

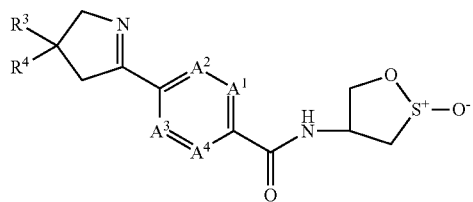

(Ia.F1)

$A^1$, $A^2$, $A^3$, $A^4$, $R^3$, and $R^4$ and their preferred values are as defined for a compound of formula (I); or a salt or N-oxide thereof.

In one embodiment the invention provides compounds of formula Ia.F2

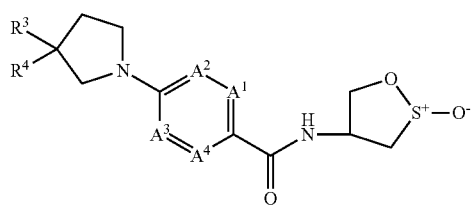

(Ia.F2)

$A^1$, $A^2$, $A^3$, $A^4$, $R^3$, and $R^4$ and their preferred values are as defined for a compound of formula (I); or a salt or N-oxide thereof.

In one embodiment the invention provides compounds of formula Ia.F3

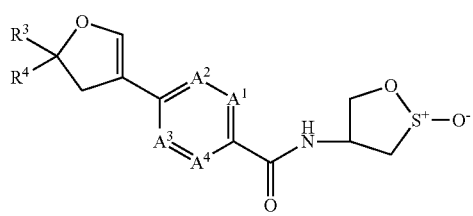

(Ia.F3)

$A^1$, $A^2$, $A^3$, $A^4$, $R^3$, and $R^4$ and their preferred values are as defined for a compound of formula (I); or a salt or N-oxide thereof.

In one embodiment the invention provides compounds of formula Ia.F4

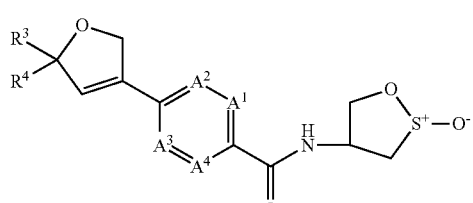

(Ia.F4)

$A^1$, $A^2$, $A^3$, $A^4$, $R^3$, and $R^4$ and their preferred values are as defined for a compound of formula (I); or a salt or N-oxide thereof.

Certain intermediates are novel and as such form a further aspect of the invention.

One group of novel intermediates are compounds of formula (Int-I)

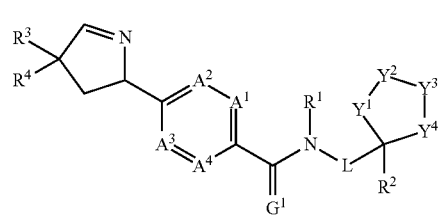

(Int-I)

wherein $A^1$, $A^2$, $A^3$, $A^4$, $G^1$, L, $R^1$, $R^2$, $R^3$, $R^4$, $Y^1$, $Y^2$, $Y^3$ and $Y^4$ are as defined for a compound of formula (I); or a salt or N-oxide thereof. The preferences for $A^1$, $A^2$, $A^3$, $A^4$, $G^1$, L, $R^1$, $R^2$, $R^3$, $R^4$, $Y^1$, $Y^2$, $Y^3$ and $Y^4$ are the same as the preferences set out for the corresponding substituents of a compound of formula (I). For example, the preferences for $A^1$, $A^2$, $A^3$, $A^4$, $G^1$, L, $R^1$, $R^2$, $R^3$, $R^4$, $Y^1$, $Y^2$, $Y^3$ and $Y^4$ may be the same as for formula (Ia.A), (Ia.B), (Ia.C), (Ia.D), (Ia.E), (Ia.E1), (Ia.E2), (Ia.F), (Ia.F1), (Ia.F2), (Ia.F3) or (Ia.F4).

Another group of novel intermediates are compounds of formula (Int-II)

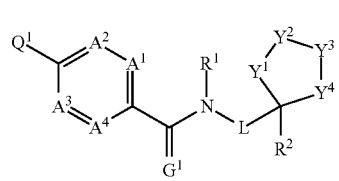

(Int-II)

wherein $Q^1$ is $CO_2H$ or $NH_2$, and wherein $A^1$, $A^2$, $A^3$, $A^4$, $G^1$, L, $R^1$, $R^2$, $Y^1$, $Y^2$, $Y^3$ and $Y^4$ are as defined for a compound of formula (I); or a salt or N-oxide thereof. The preferences for $A^1$, $A^2$, $A^3$, $A^4$, $G^1$, L, $R^1$, $R^2$, $Y^1$, $Y^2$, $Y^3$ and $Y^4$ are the same as the preferences set out for the corresponding substituents of a compound of formula (I). For example, the preferences for $A^1$, $A^2$, $A^3$, $A^4$, $G^1$, L, $R^1$, $R^2$, $Y^1$, $Y^2$, $Y^3$ and $Y^4$ may be the same as for formula (Ia.A), (Ia.B), (Ia.C), (Ia.D), (Ia.E), (Ia.E1), (Ia.E2), (Ia.F), (Ia.F1), (Ia.F2), (Ia.F3) or (Ia.F4).

Another group of novel intermediates are compounds of formula (Int-III)

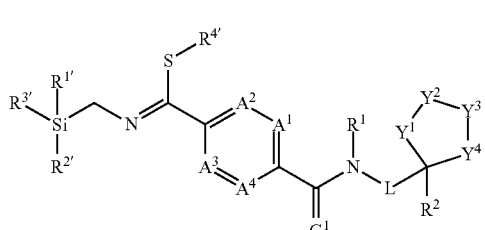

(Int-III)

wherein $R^{1'}$, $R^{2'}$ and $R^{3'}$ are independently of each other optionally substituted alkyl or optionally substituted phenyl, $R^{4'}$ is optionally substituted alkyl, and $A^1$, $A^2$, $A^3$, $A^4$, $G^1$, L, $R^1$, $R^2$, $Y^1$, $Y^2$, $Y^3$ and $Y^4$ as defined for a compound of formula (I); or a salt or N-oxide thereof. The preferences for $A^1, A^2, A^3, A^4, G^1, L, R^1, R^2, Y^1, Y^2, Y^3$ and $Y^4$ are the same as the preferences set out for the corresponding substituents of a compound of formula (I). For example, the preferences for $A^1, A^2, A^3, A^4, G^1, L, R^1, R^2, Y^1, Y^2, Y^3$ and $Y^4$ may be the same as for formula (Ia.A), (Ia.B), (Ia.C), (Ia.D), (Ia.E), (Ia.E1), (Ia.E2), (Ia.F), (Ia.F1), (Ia.F2), (Ia.F3) or (Ia.F4). Preferably $R^1$, $R^{2'}$ and $R^{3'}$ are each independently $C_1$-$C_8$alkyl or phenyl. Preferably $R^{4'}$ is $C_1$-$C_8$ alkyl.

Another group of novel intermediates are compounds of formula (Int-IV)

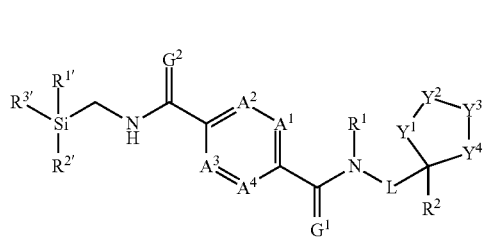

(Int-IV)

wherein $G^2$ is O or S, $R^{1'}$, $R^{2'}$ and $R^{3'}$ are independently of each other optionally substituted alkyl or optionally substituted phenyl, and $A^1, A^2, A^3, A^4, G^1, L, R^1, R^2, Y^1, Y^2, Y^3$ and $Y^4$ as defined for a compound of formula (I); or a salt or N-oxide thereof. The preferences for $A^1, A^2, A^3, A^4, G^1, L, R^1, R^2, Y^1, Y^2, Y^3$ and $Y^4$ are the same as the preferences set out for the corresponding substituents of a compound of formula (I). For example, the preferences for $A^1, A^2, A^3, A^4, G^1, L, R^1, R^2, Y^1, Y^2, Y^3$ and $Y^4$ may be the same as for formula (Ia.A), (Ia.B), (Ia.C), (Ia.D), (Ia.E), (Ia.E1), (Ia.E2), (Ia.F), (Ia.F1), (Ia.F2), (Ia.F3) or (Ia.F4). Preferably $R^{1'}$, $R^{2'}$ and $R^{3'}$ are each independently $C_1$-$C_8$alkyl or phenyl. Preferably $R^{4'}$ is $C_1$-$C_8$ alkyl.

Another group of novel intermediates are compounds of formula (Int-V)

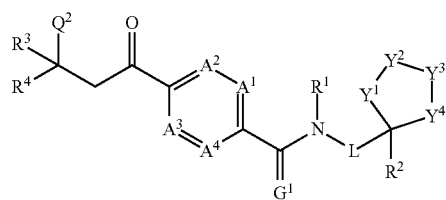

(Int-V)

wherein $Q^2$ is $CH_2$—$NO_2$, CN or group Qa

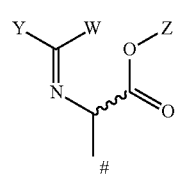

(Qa)

W is hydrogen or optionally substituted aryl, Y is optionally substituted aryl, and Z is optionally substituted alkyl or optionally substituted arylalkylene, and $A^1, A^2, A^3, A^4, G^1, L, R^1, R^2, R^3, R^4, Y^1, Y^2, Y^3$ and $Y^4$ are as defined for a compound of formula (I); or a salt or N-oxide thereof. The preferences for $A^1, A^2, A^3, A^4, G^1, L, R^1, R^2, R^3, R^4, Y^1, Y^2, Y^3$ and $Y^4$ are the same as the preferences set out for the corresponding substituents of a compound of formula (I). For example, the preferences for $A^1, A^2, A^3, A^4, G^1, L, R^1, R^2, R^3, R^4, Y^1, Y^2, Y^3$ and $Y^4$ may be the same as for formula (Ia.A), (Ia.B), (Ia.C), (Ia.D), (Ia.E), (Ia.E1), (Ia.E2), (Ia.F), (Ia.F1), (Ia.F2), (Ia.F3) or (Ia.F4). Preferably W is hydrogen or phenyl. Preferably Y is phenyl. Preferably Z is $C_1$-$C_8$alkyl, or phenyl-$C_1$-$C_8$alkyl.

Another group of novel intermediates are compounds of formula (Int-VI)

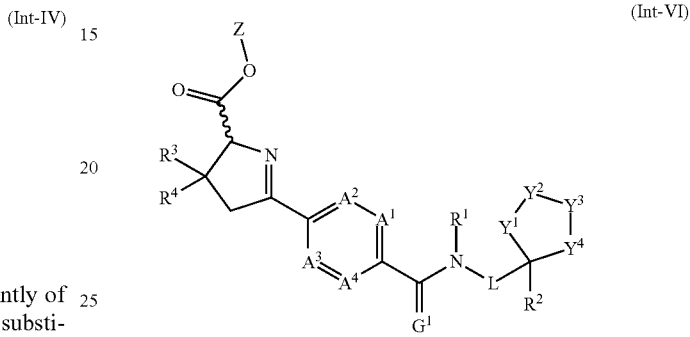

(Int-VI)

wherein Z is optionally substituted alkyl or optionally substituted arylalkylene, and $A^1, A^2, A^3, A^4, G^1, L, R^1, R^2, R^3, R^4, Y^1, Y^2, Y^3$ and $Y^4$ are as defined for a compound of formula (I); or a salt or N-oxide thereof. The preferences for $A^1, A^2, A^3, A^4, G^1, L, R^1, R^2, R^3, R^4, Y^1, Y^2, Y^3$ and $Y^4$ are the same as the preferences set out for the corresponding substituents of a compound of formula (I). For example, the preferences for $A^1, A^2, A^3, A^4, G^1, L, R^1, R^2, R^3, R^4, Y^1, Y^2, Y^3$ and $Y^4$ may be the same as for formula (Ia.A), (Ia.B), (Ia.C), (Ia.D), (Ia.E), (Ia.E1), (Ia.E2), (Ia.F), (Ia.F1), (Ia.F2), (Ia.F3) or (Ia.F4). Preferably Z is $C_1$-$C_8$alkyl, or phenyl-$C_1$-$C_8$alkyl.

Another group of novel intermediates are compounds of formula (Int-VII)

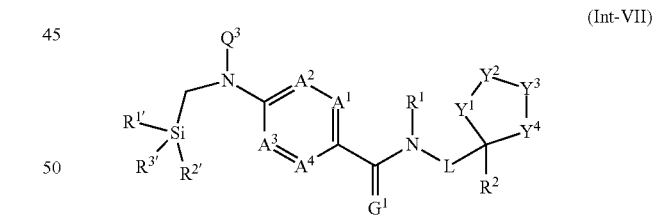

(Int-VII)

wherein $Q^3$ is $CH_2$—$OR^{4'}$ or $CH_2$—CN, $R^{1'}$, $R^{2'}$ and $R^{3'}$ are independently of each other optionally substituted alkyl or optionally substituted phenyl, $R^{4'}$ is optionally substituted alkyl, and $A^1, A^2, A^3, A^4, G^1, L, R^1, R^2, Y^1, Y^2, Y^3$ and $Y^4$ are as defined for a compound of formula (I); or a salt or N-oxide thereof. The preferences for $A^1, A^2, A^3, A^4, G^1, L, R^1, R^2, Y^1, Y^2, Y^3$ and $Y^4$ are the same as the preferences set out for the corresponding substituents of a compound of formula (I). For example, the preferences for $A^1, A^2, A^3, A^4, G^1, L, R^1, R^2, Y^1, Y^2, Y^3$ and $Y^4$ may be the same as for formula (Ia.A), (Ia.B), (Ia.C), (Ia.D), (Ia.E), (Ia.E1), (Ia.E2), (Ia.F), (Ia.F1), (Ia.F2), (Ia.F3) or (Ia.F4). Preferably $R^{1'}$, $R^{2'}$ and $R^{3'}$ are each independently $C_1$-$C_8$alkyl or phenyl. Preferably $R^{4'}$ is $C_1$-$C_8$ alkyl.

Another group of novel intermediates are compounds of formula (Int-VIII)

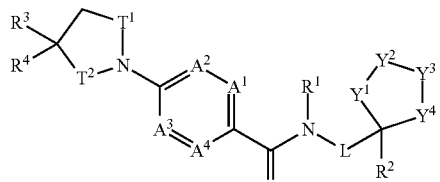
(Int-VIII)

wherein $T^1$ and $T^2$ are independently $CH_2$ or $C=O$, providing that at least one of $T^1$ and $T^2$ is $C=O$, and $A^1$, $A^2$, $A^3$, $A^4$, $G^1$, L, $R^1$, $R^2$, $R^3$, $R^4$, $Y^1$, $Y^2$, $Y^3$ and $Y^4$ are as defined for a compound of formula (I); or a salt or N-oxide thereof. The preferences for $A^1$, $A^2$, $A^3$, $A^4$, $G^1$, L, $R^1$, $R^2$, $R^3$, $R^4$, $Y^1$, $Y^2$, $Y^3$ and $Y^4$ are the same as the preferences set out for the corresponding substituents of a compound of formula (I). For example, the preferences for $A^1$, $A^2$, $A^3$, $A^4$, $G^1$, L, $R^1$, $R^2$, $R^3$, $R^4$, $Y^1$, $Y^2$, $Y^3$ and $Y^4$ may be the same as for formula (Ia.A), (Ia.B), (Ia.C), (Ia.D), (Ia.E) or (Ia.F).

The compounds in Table 1 to Table 120 below illustrate the compounds of the invention.

TABLE 1

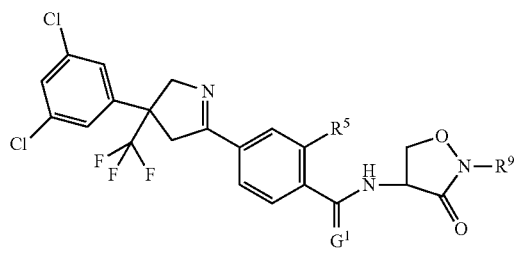
(Iaa)

Table 1 provides 295 compounds of formula (Iaa) wherein $G^1$ is oxygen, and $R^5$ and $R^9$ have the values listed in table X below.

TABLE 2

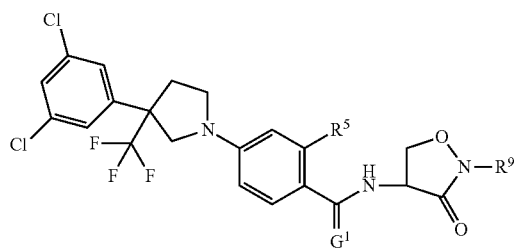
(Iba)

Table 2 provides 295 compounds of formula (Iba) wherein $G^1$ is oxygen, and $R^5$ and $R^9$ have the values listed in table X below.

TABLE 3

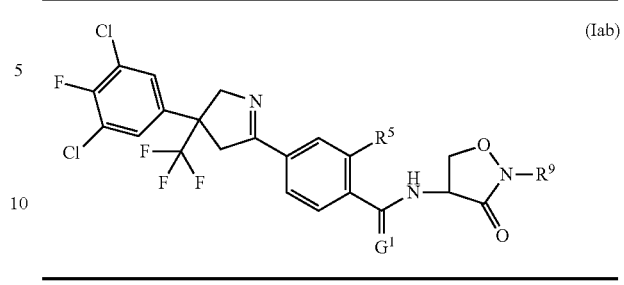
(Iab)

Table 3 provides 295 compounds of formula (Iab) wherein $G^1$ is oxygen, and $R^5$ and $R^9$ have the values listed in table X below.

TABLE 4

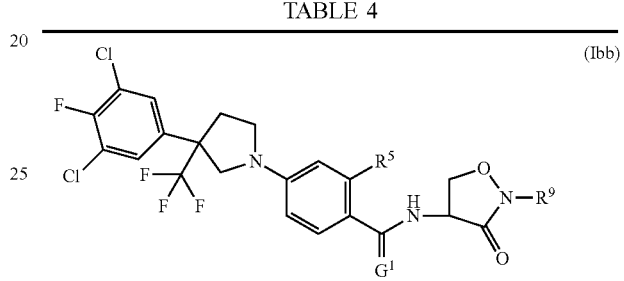
(Ibb)

Table 4 provides 295 compounds of formula (Ibb) wherein $G^1$ is oxygen, and $R^5$ and $R^9$ have the values listed in table X below.

TABLE 5

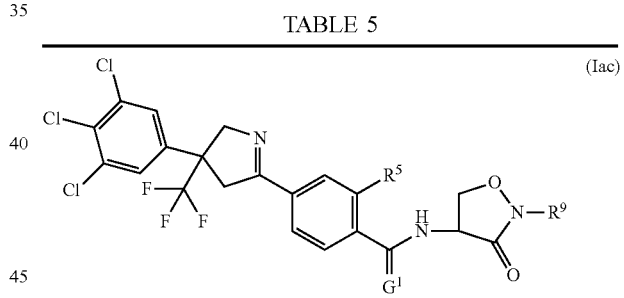
(Iac)

Table 5 provides 295 compounds of formula (Iac) wherein $G^1$ is oxygen, and $R^5$ and $R^9$ have the values listed in table X below.

TABLE 6

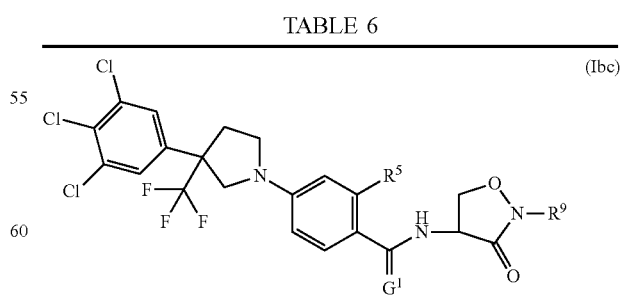
(Ibc)

Table 6 provides 295 compounds of formula (Ibc) wherein $G^1$ is oxygen, and $R^5$ and $R^9$ have the values listed in table X below.

TABLE 7

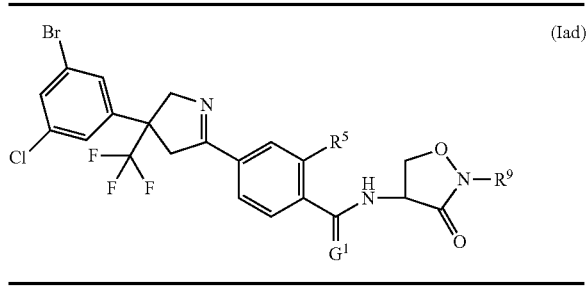
(Iad)

Table 7 provides 295 compounds of formula (Iad) wherein $G^1$ is oxygen, and $R^5$ and $R^9$ have the values listed in table X below.

TABLE 8

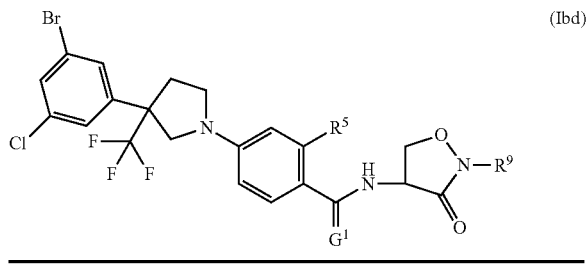
(Ibd)

Table 8 provides 295 compounds of formula (Ibd) wherein $G^1$ is oxygen, and $R^5$ and $R^9$ have the values listed in table X below.

TABLE 9

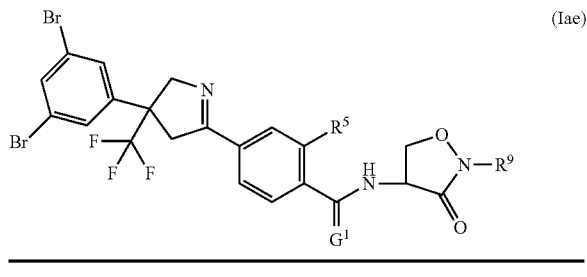
(Iae)

Table 9 provides 295 compounds of formula (Iae) wherein $G^1$ is oxygen, and $R^5$ and $R^9$ have the values listed in table X below.

TABLE 10

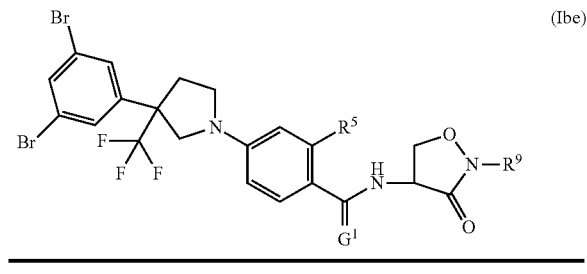
(Ibe)

Table 10 provides 295 compounds of formula (Ibe) wherein $G^1$ is oxygen, and $R^5$ and $R^9$ have the values listed in table X below.

TABLE 11

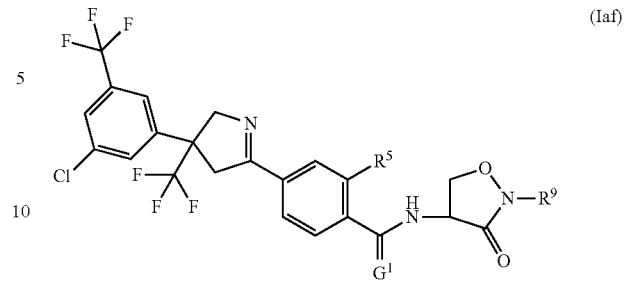
(Iaf)

Table 11 provides 295 compounds of formula (Iaf) wherein $G^1$ is oxygen, and $R^5$ and $R^9$ have the values listed in table X below.

TABLE 12

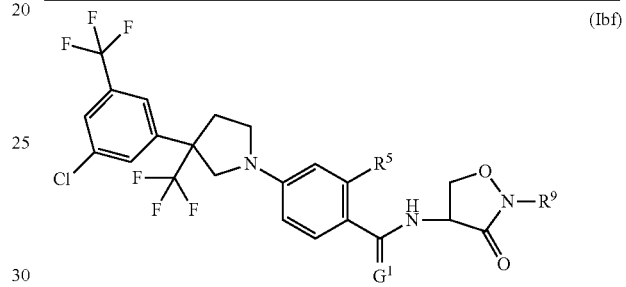
(Ibf)

Table 12 provides 295 compounds of formula (Ibf) wherein $G^1$ is oxygen, and $R^5$ and $R^9$ have the values listed in table X below.

TABLE 13

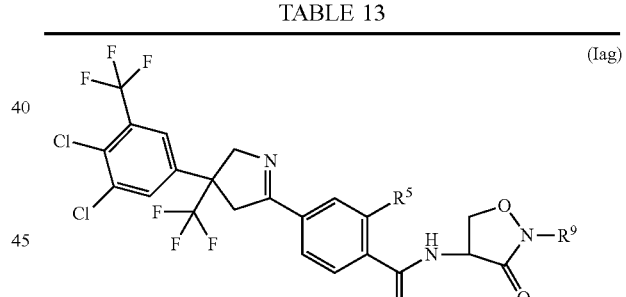
(Iag)

Table 13 provides 295 compounds of formula (Iag) wherein $G^1$ is oxygen, and $R^5$ and $R^9$ have the values listed in table X below.

TABLE 14

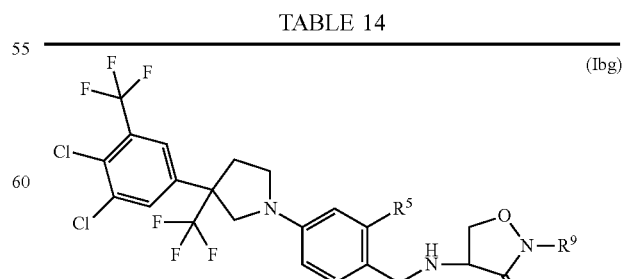
(Ibg)

Table 14 provides 295 compounds of formula (Iag) wherein $G^1$ is oxygen, and $R^5$ and $R^9$ have the values listed in table X below.

TABLE 15

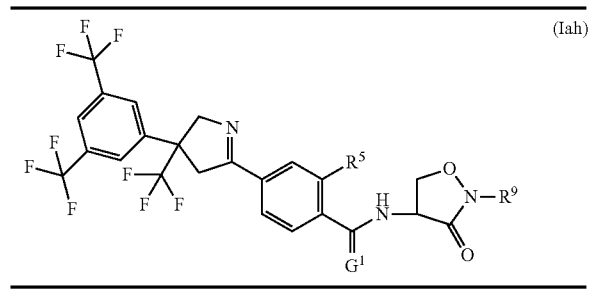

(Iah)

Table 15 provides 295 compounds of formula (Iah) wherein $G^1$ is oxygen, and $R^5$ and $R^9$ have the values listed in table X below.

TABLE 16

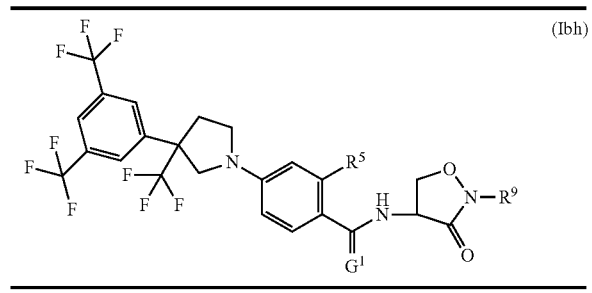

(Ibh)

Table 16 provides 295 compounds of formula (Ibh) wherein $G^1$ is oxygen, and $R^5$ and $R^9$ have the values listed in table X below.

TABLE 17

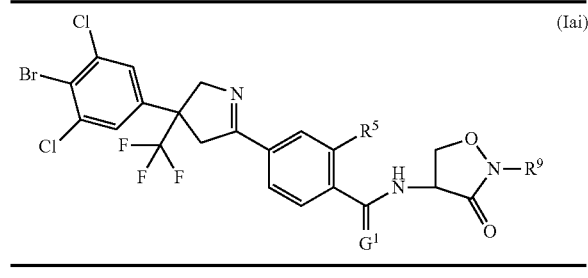

(Iai)

Table 17 provides 295 compounds of formula (Iai) wherein $G^1$ is oxygen, and $R^5$ and $R^9$ have the values listed in table X below.

TABLE 18

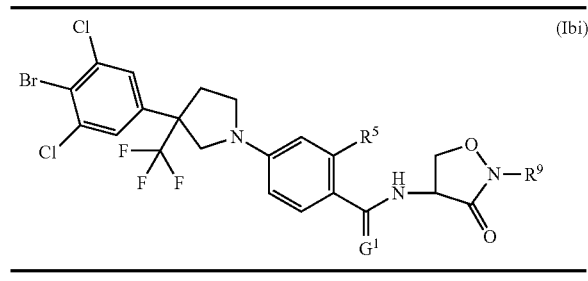

(Ibi)

Table 18 provides 295 compounds of formula (Ibi) wherein $G^1$ is oxygen, and $R^5$ and $R^9$ have the values listed in table X below.

TABLE 19

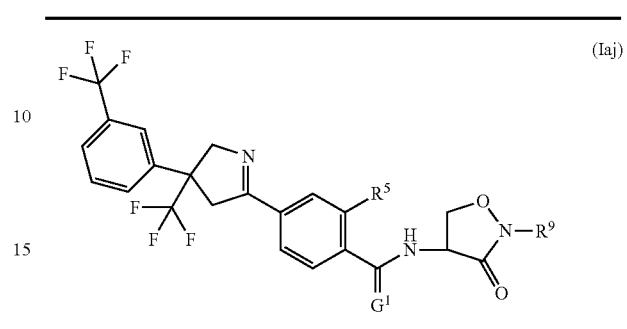

(Iaj)

Table 19 provides 295 compounds of formula (Iaj) wherein $G^1$ is oxygen, and $R^5$ and $R^9$ have the values listed in table X below.

TABLE 20

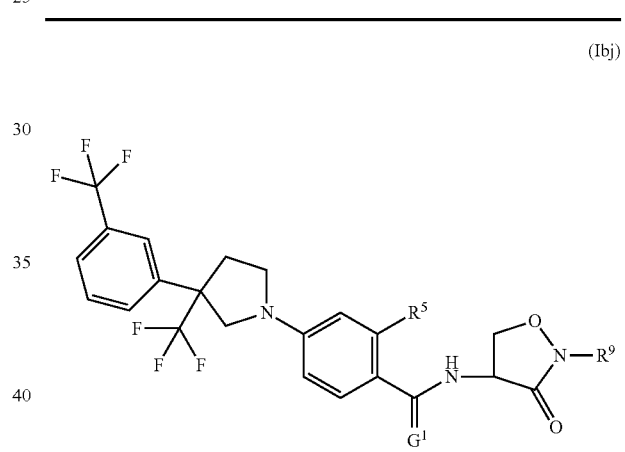

(Ibj)

Table 20 provides 295 compounds of formula (Ibj) wherein $G^1$ is oxygen, and $R^5$ and $R^9$ have the values listed in table X below.

TABLE 21

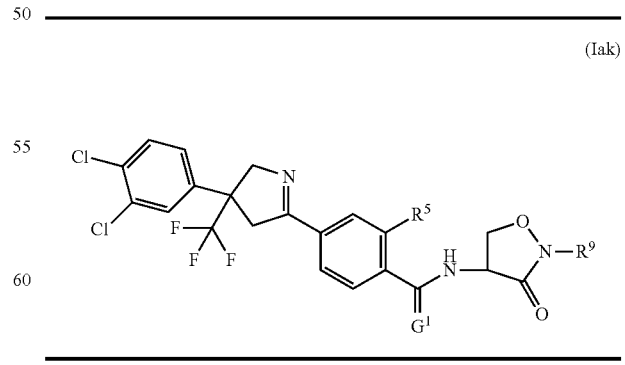

(Iak)

Table 21 provides 295 compounds of formula (Iak) wherein $G^1$ is oxygen, and $R^5$ and $R^9$ have the values listed in table X below.

TABLE 22

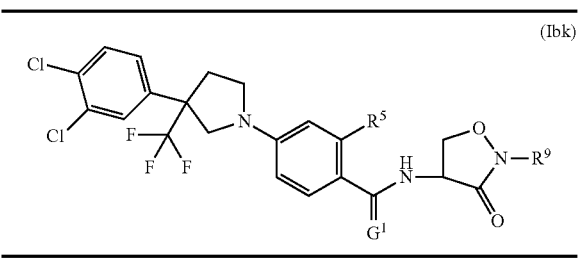
(Ibk)

Table 22 provides 295 compounds of formula (Ibk) wherein $G^1$ is oxygen, and $R^5$ and $R^9$ have the values listed in table X below.

TABLE 23

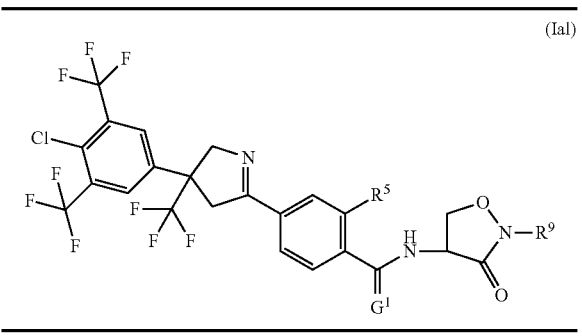
(Ial)

Table 23 provides 295 compounds of formula (Ial) wherein $G^1$ is oxygen, and $R^5$ and $R^9$ have the values listed in table X below.

TABLE 24

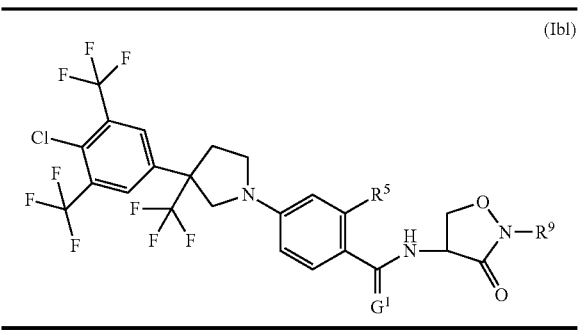
(Ibl)

Table 24 provides 295 compounds of formula (Ibl) wherein $G^1$ is oxygen, and $R^5$ and $R^9$ have the values listed in table X below.

TABLE 25

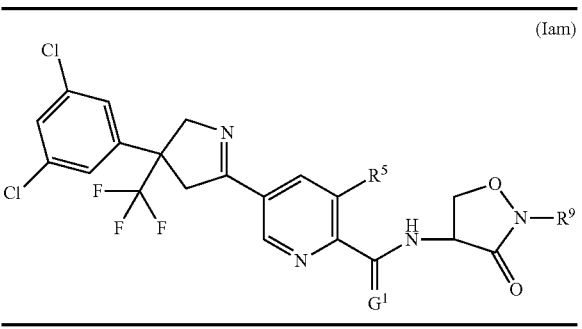
(Iam)

Table 25 provides 295 compounds of formula (Iam) wherein $G^1$ is oxygen, and $R^5$ and $R^9$ have the values listed in table X below.

TABLE 26

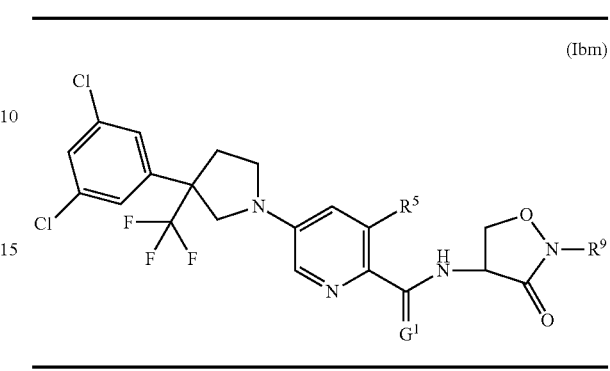
(Ibm)

Table 26 provides 295 compounds of formula (Ibm) wherein $G^1$ is oxygen, and $R^5$ and $R^9$ have the values listed in table X below.

TABLE 27

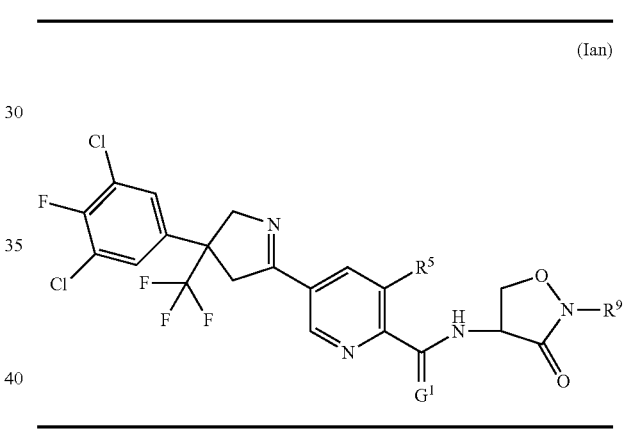
(Ian)

Table 27 provides 295 compounds of formula (Ian) wherein $G^1$ is oxygen, and $R^5$ and $R^9$ have the values listed in table X below.

TABLE 28

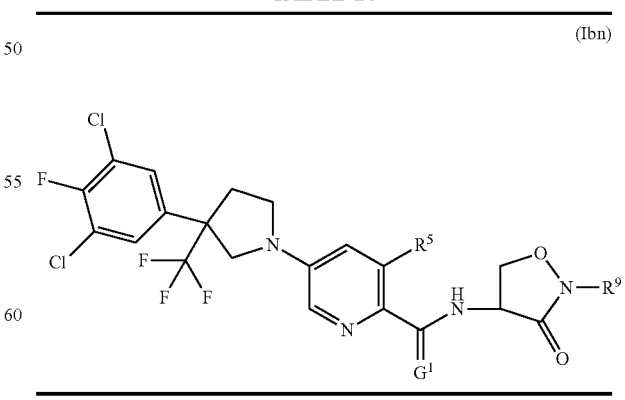
(Ibn)

Table 28 provides 295 compounds of formula (Ibn) wherein $G^1$ is oxygen, and $R^5$ and $R^9$ have the values listed in table X below.

TABLE 29

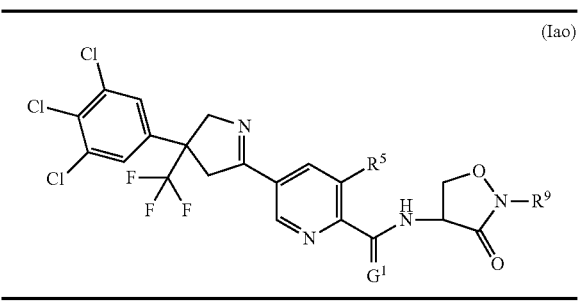
(Iao)

Table 29 provides 295 compounds of formula (Iao) wherein $G^1$ is oxygen, and $R^5$ and $R^9$ have the values listed in table X below.

TABLE 30

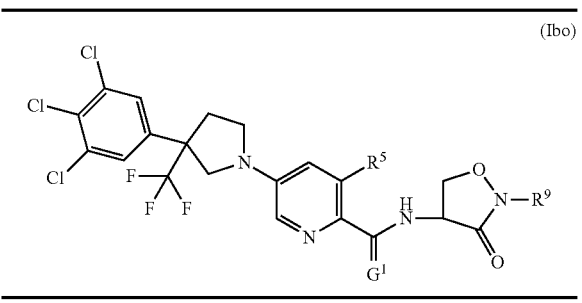
(Ibo)

Table 30 provides 295 compounds of formula (Ibo) wherein $G^1$ is oxygen, and $R^5$ and $R^9$ have the values listed in table X below.

TABLE 31

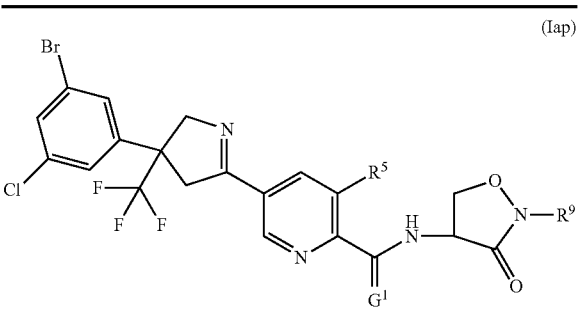
(Iap)

Table 31 provides 295 compounds of formula (Iap) wherein $G^1$ is oxygen, and $R^5$ and $R^9$ have the values listed in table X below.

TABLE 32

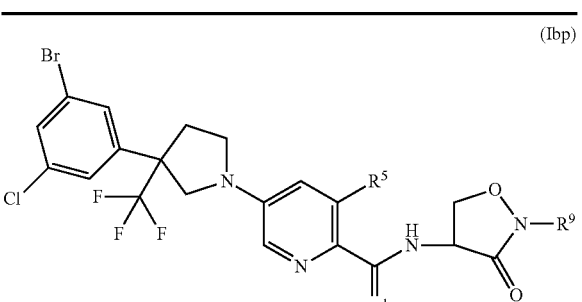
(Ibp)

Table 32 provides 295 compounds of formula (Ibp) wherein $G^1$ is oxygen, and $R^5$ and $R^9$ have the values listed in table X below.

TABLE 33

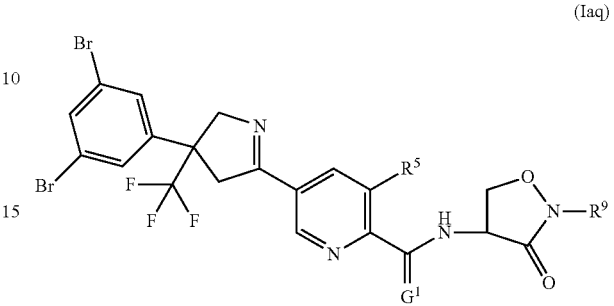
(Iaq)

Table 33 provides 295 compounds of formula (Iaq) wherein $G^1$ is oxygen, and $R^5$ and $R^9$ have the values listed in table X below.

TABLE 34

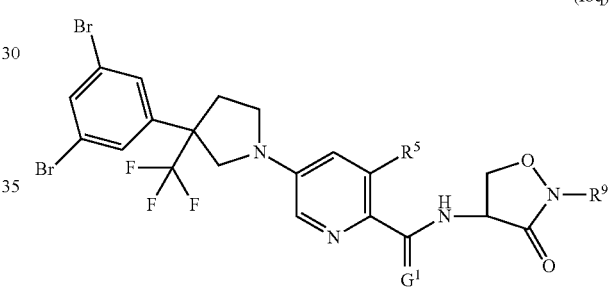
(Ibq)

Table 34 provides 295 compounds of formula (Ibq) wherein $G^1$ is oxygen, and $R^5$ and $R^9$ have the values listed in table X below.

TABLE 35

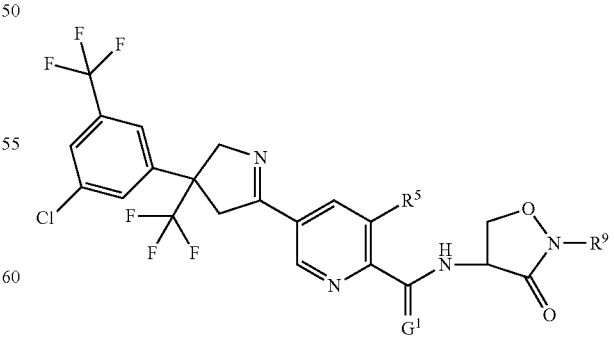
(Iar)

Table 35 provides 295 compounds of formula (Iar) wherein $G^1$ is oxygen, and $R^5$ and $R^9$ have the values listed in table X below.

TABLE 36

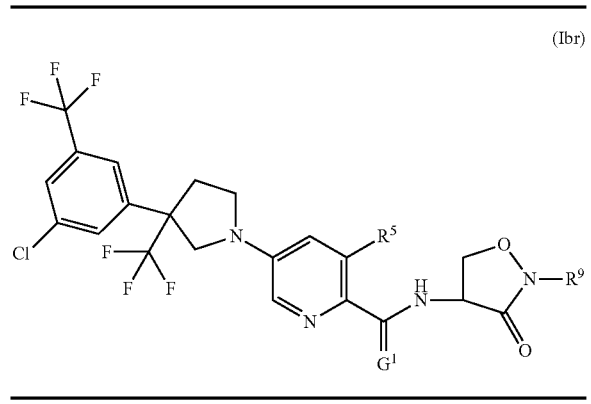

(Ibr)

Table 36 provides 295 compounds of formula (Ibr) wherein $G^1$ is oxygen, and $R^5$ and $R^9$ have the values listed in table X below.

TABLE 37

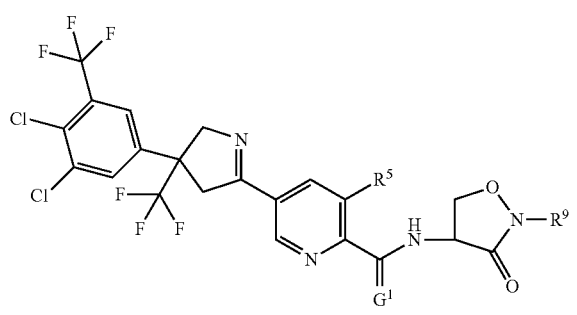

(Ias)

Table 37 provides 295 compounds of formula (Ias) wherein $G^1$ is oxygen, and $R^5$ and $R^9$ have the values listed in table X below.

TABLE 38

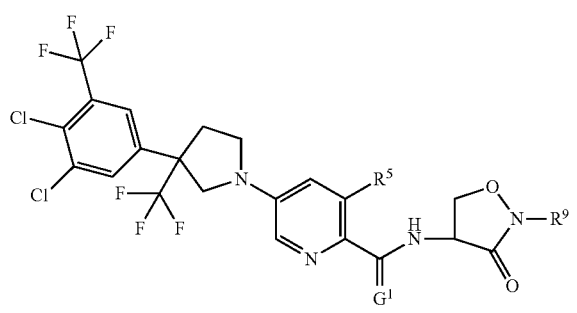

(Ibs)

Table 38 provides 295 compounds of formula (Ibs) wherein $G^1$ is oxygen, and $R^5$ and $R^9$ have the values listed in table X below.

TABLE 39

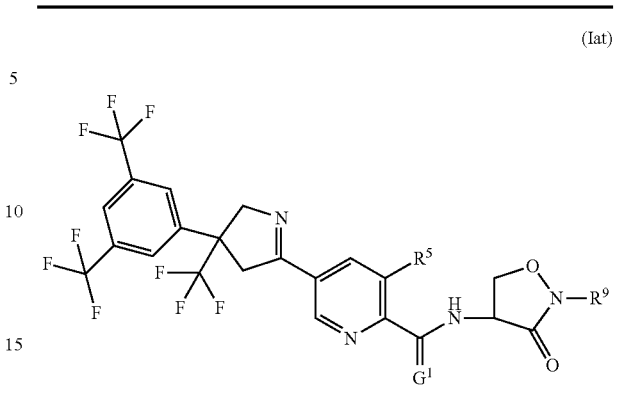

(Iat)

Table 39 provides 295 compounds of formula (Iat) wherein $G^1$ is oxygen, and $R^5$ and $R^9$ have the values listed in table X below.

TABLE 40

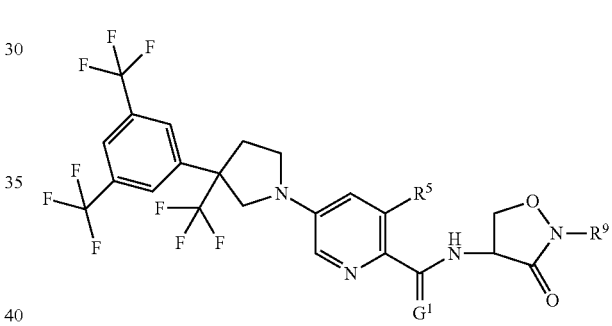

(Ibt)

Table 40 provides 295 compounds of formula (Ibt) wherein $G^1$ is oxygen, and $R^5$ and $R^9$ have the values listed in table X below.

TABLE 41

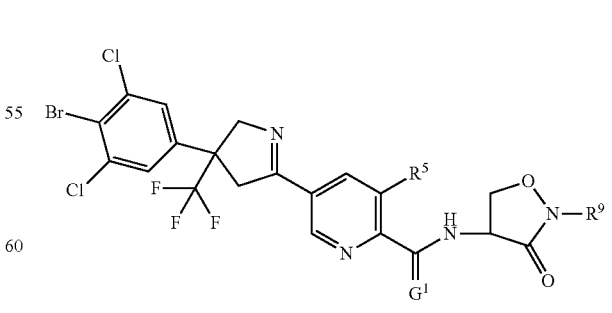

(Iau)

Table 41 provides 295 compounds of formula (Iau) wherein $G^1$ is oxygen, and $R^5$ and $R^9$ have the values listed in table X below.

TABLE 42

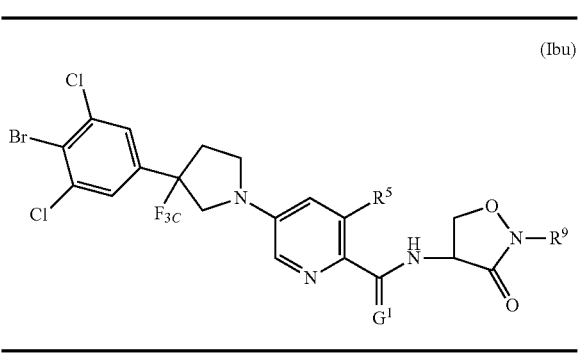

(Ibu)

Table 42 provides 295 compounds of formula (Ibu) wherein $G^1$ is oxygen, and $R^5$ and $R^9$ have the values listed in table X below.

TABLE 43

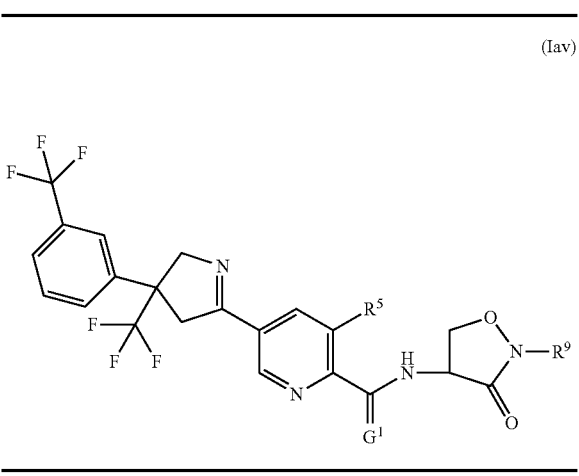

(Iav)

Table 43 provides 295 compounds of formula (Iav) wherein $G^1$ is oxygen, and $R^5$ and $R^9$ have the values listed in table X below.

TABLE 44

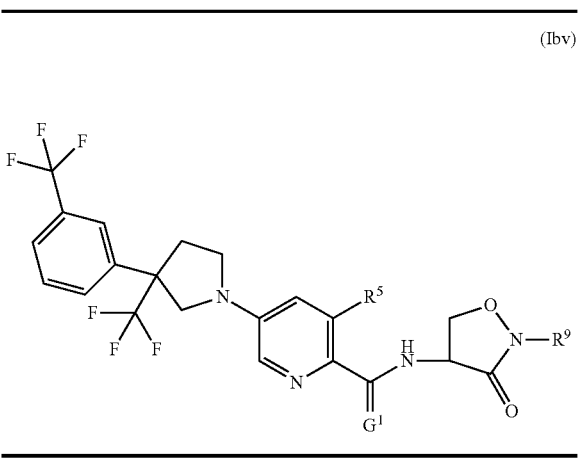

(Ibv)

Table 44 provides 295 compounds of formula (Ibv) wherein $G^1$ is oxygen, and $R^5$ and $R^9$ have the values listed in table X below.

TABLE 45

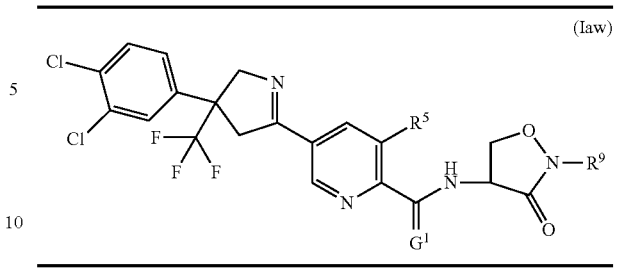

(Iaw)

Table 45 provides 295 compounds of formula (Iaw) wherein $G^1$ is oxygen, and $R^5$ and $R^9$ have the values listed in table X below.

TABLE 46

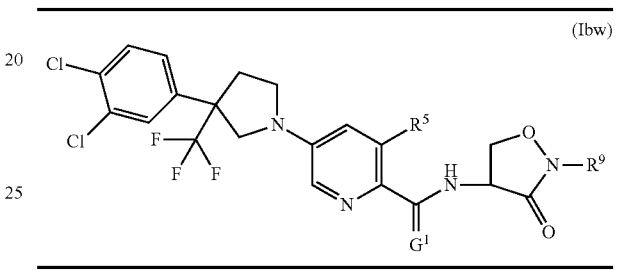

(Ibw)

Table 46 provides 295 compounds of formula (Ibw) wherein $G^1$ is oxygen, and $R^5$ and $R^9$ have the values listed in table X below.

TABLE 47

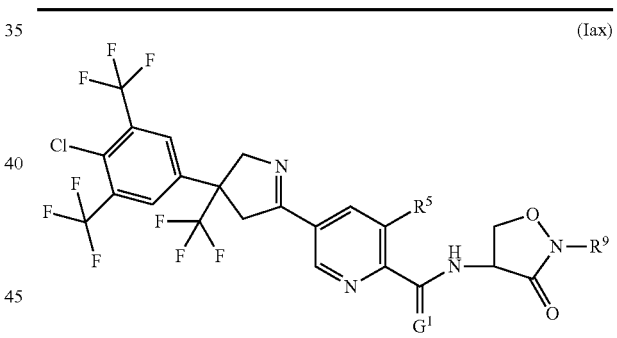

(Iax)

Table 47 provides 295 compounds of formula (Iax) wherein $G^1$ is oxygen, and $R^5$ and $R^9$ have the values listed in table X below.

TABLE 48

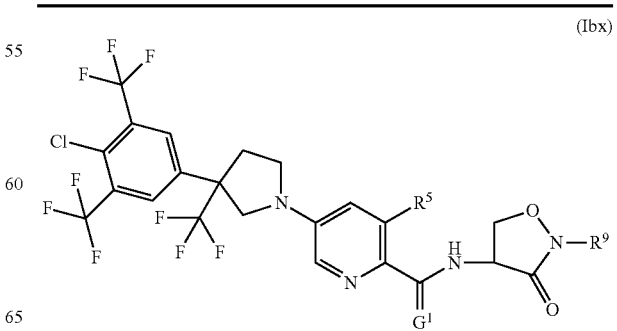

(Ibx)

Table 48 provides 295 compounds of formula (Ibx) wherein $G^1$ is oxygen, and $R^5$ and $R^9$ have the values listed in table X below.

TABLE 49

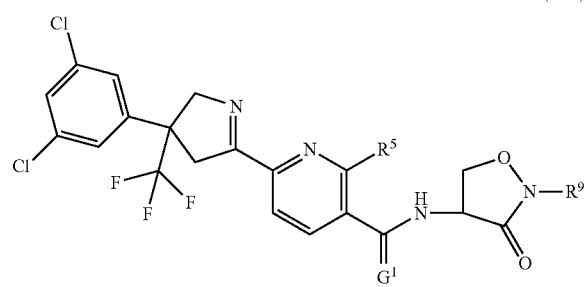
(Iaaa)

Table 49 provides 295 compounds of formula (Iaaa) wherein $G^1$ is oxygen, and $R^5$ and $R^9$ have the values listed in table X below.

TABLE 50

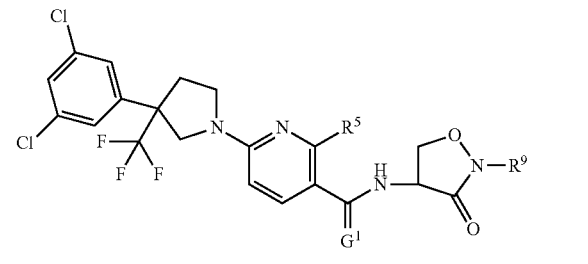
(Ibaa)

Table 50 provides 295 compounds of formula (Ibaa) wherein $G^1$ is oxygen, and $R^5$ and $R^9$ have the values listed in table X below.

TABLE 51

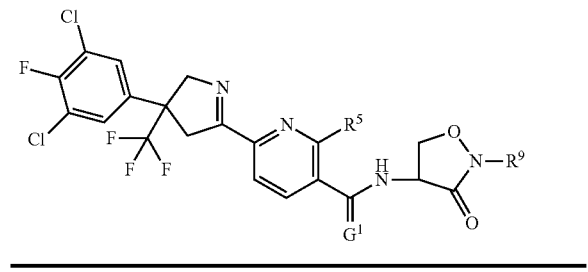
(Iaab)

Table 51 provides 295 compounds of formula (Iaab) wherein $G^1$ is oxygen, and $R^5$ and $R^9$ have the values listed in table X below.

TABLE 52

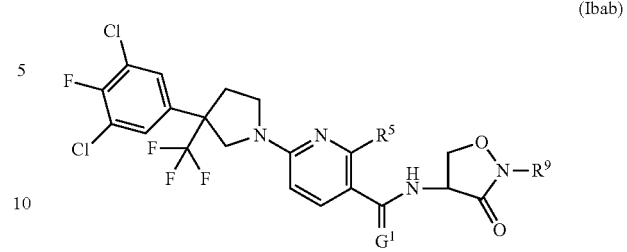
(Ibab)

Table 52 provides 295 compounds of formula (Ibab) wherein $G^1$ is oxygen, and $R^5$ and $R^9$ have the values listed in table X below.

TABLE 53

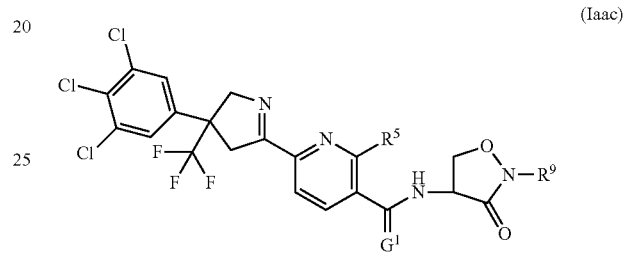
(Iaac)

Table 53 provides 295 compounds of formula (Iaac) wherein $G^1$ is oxygen, and $R^5$ and $R^9$ have the values listed in table X below.

TABLE 54

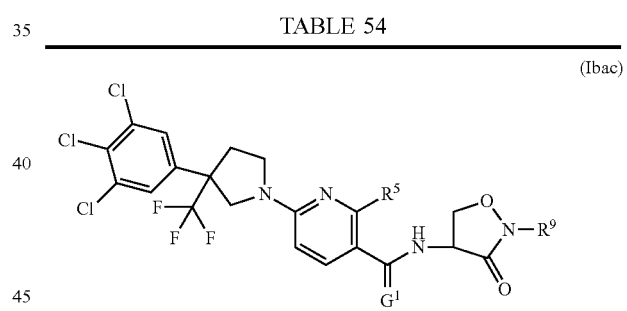
(Ibac)

Table 54 provides 295 compounds of formula (Ibac) wherein $G^1$ is oxygen, and $R^5$ and $R^9$ have the values listed in table X below.

TABLE 55

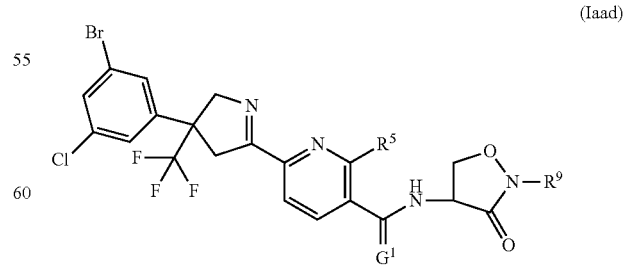
(Iaad)

Table 55 provides 295 compounds of formula (Iaad) wherein $G^1$ is oxygen, and $R^5$ and $R^9$ have the values listed in table X below.

TABLE 56

(Ibad)

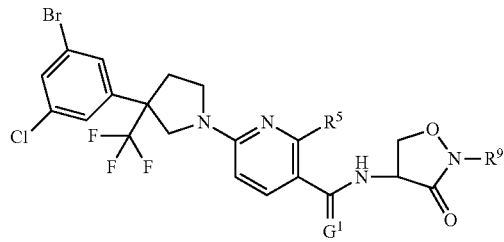

Table 56 provides 295 compounds of formula (Ibad) wherein $G^1$ is oxygen, and $R^5$ and $R^9$ have the values listed in table X below.

TABLE 57

(Iaae)

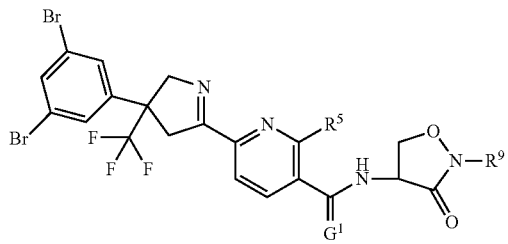

Table 57 provides 295 compounds of formula (Iaae) wherein $G^1$ is oxygen, and $R^5$ and $R^9$ have the values listed in table X below.

TABLE 58

(Ibae)

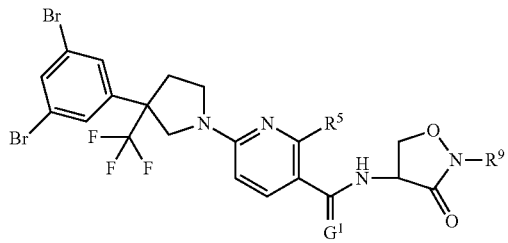

Table 58 provides 295 compounds of formula (Ibae) wherein $G^1$ is oxygen, and $R^5$ and $R^9$ have the values listed in table X below.

TABLE 59

(Iaaf)

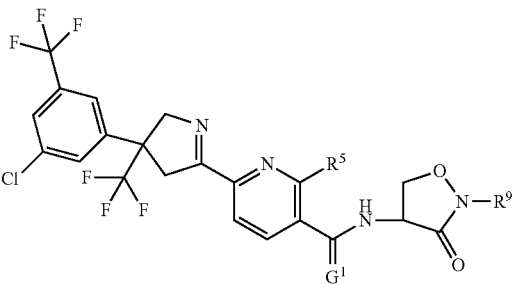

Table 59 provides 295 compounds of formula (Iaaf) wherein $G^1$ is oxygen, and $R^5$ and $R^9$ have the values listed in table X below.

TABLE 60

(Ibaf)

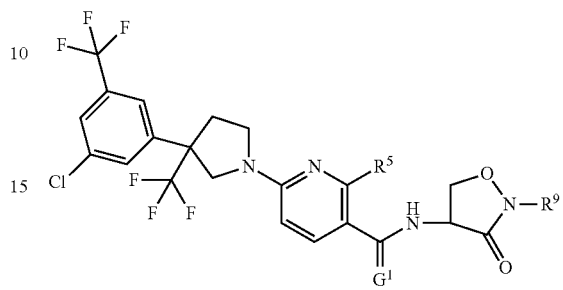

Table 60 provides 295 compounds of formula (Ibaf) wherein $G^1$ is oxygen, and $R^5$ and $R^9$ have the values listed in table X below.

TABLE 61

(Iaag)

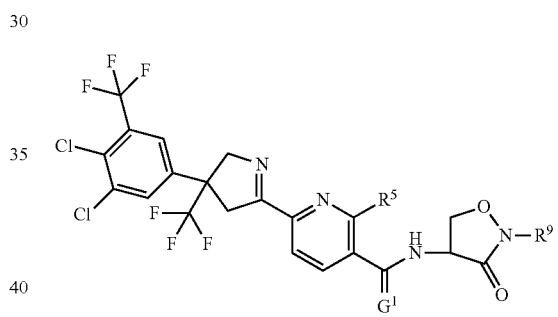

Table 61 provides 295 compounds of formula (Iaag) wherein $G^1$ is oxygen, and $R^5$ and $R^9$ have the values listed in table X below.

TABLE 62

(Ibag)

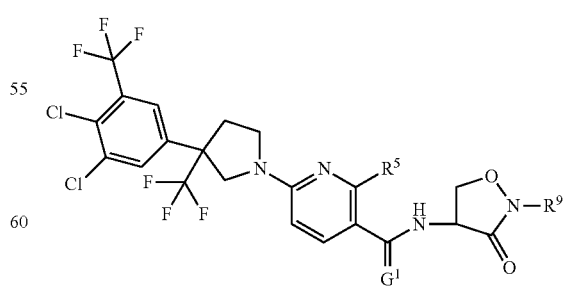

Table 62 provides 295 compounds of formula (Ibag) wherein $G^1$ is oxygen, and $R^5$ and $R^9$ have the values listed in table X below.

TABLE 63

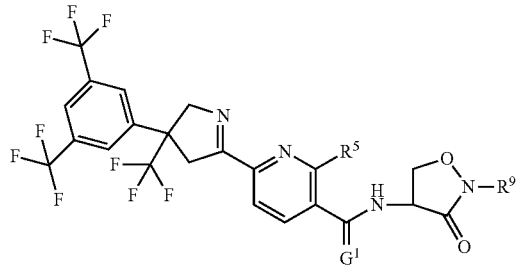
(Iaah)

Table 63 provides 295 compounds of formula (Iaah) wherein $G^1$ is oxygen, and $R^5$ and $R^9$ have the values listed in table X below.

TABLE 64

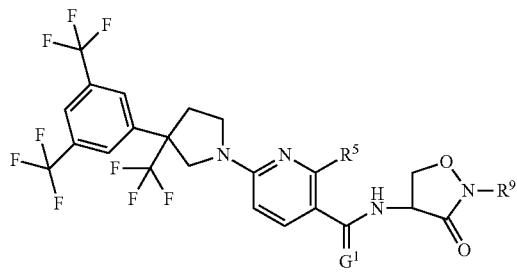
(Ibah)

Table 64 provides 295 compounds of formula (Ibah) wherein $G^1$ is oxygen, and $R^5$ and $R^9$ have the values listed in table X below.

TABLE 65

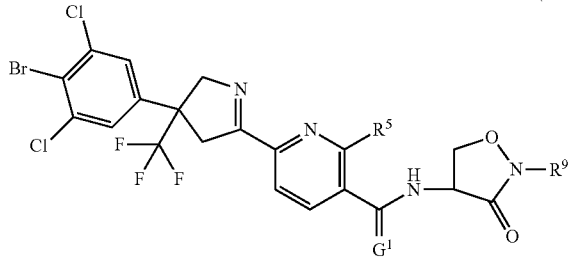
(Iaai)

Table 65 provides 295 compounds of formula (Iaai) wherein $G^1$ is oxygen, and $R^5$ and $R^9$ have the values listed in table X below.

TABLE 66

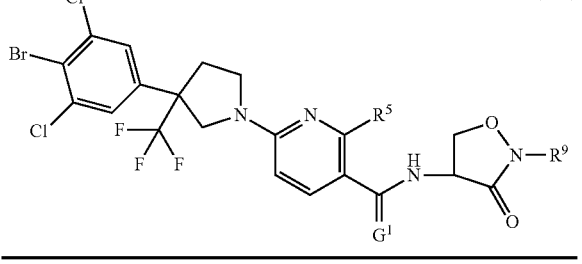
(Ibai)

Table 66 provides 295 compounds of formula (Ibai) wherein $G^1$ is oxygen, and $R^5$ and $R^9$ have the values listed in table X below.

TABLE 67

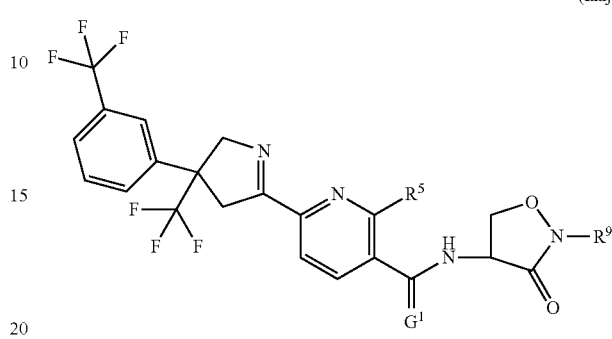
(Iaaj)

Table 67 provides 295 compounds of formula (Iaaj) wherein $G^1$ is oxygen, and $R^5$ and $R^9$ have the values listed in table X below.

TABLE 68

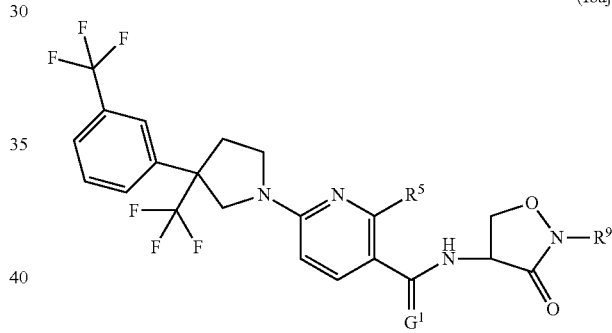
(Ibaj)

Table 68 provides 295 compounds of formula (Ibaj) wherein $G^1$ is oxygen, and $R^5$ and $R^9$ have the values listed in table X below.

TABLE 69

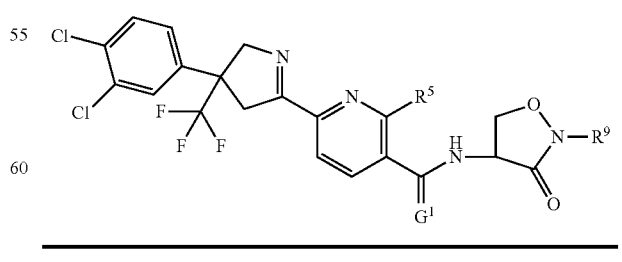
(Iaak)

Table 69 provides 295 compounds of formula (Iaak) wherein $G^1$ is oxygen, and $R^5$ and $R^9$ have the values listed in table X below.

TABLE 70

(Ibak)

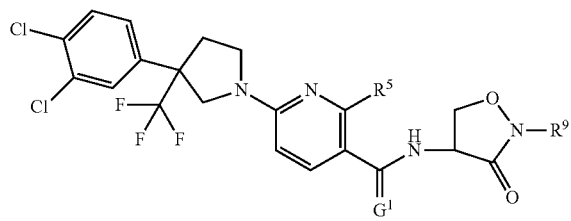

Table 70 provides 295 compounds of formula (Ibak) wherein $G^1$ is oxygen, and $R^5$ and $R^9$ have the values listed in table X below.

TABLE 71

(Iaal)

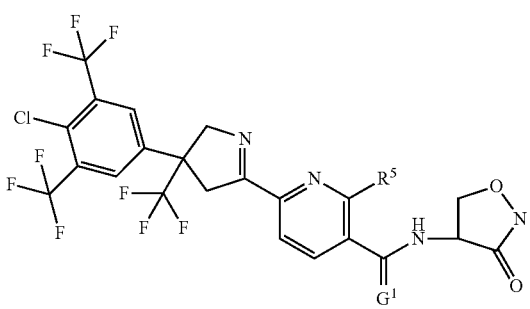

Table 71 provides 295 compounds of formula (Iaal) wherein $G^1$ is oxygen, and $R^5$ and $R^9$ have the values listed in table X below.

TABLE 72

(Ibal)

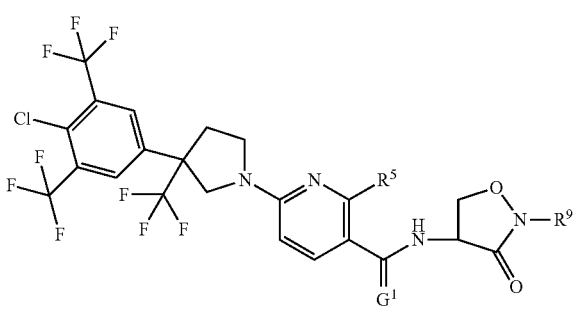

Table 72 provides 295 compounds of formula (Ibal) wherein $G^1$ is oxygen, and $R^5$ and $R^9$ have the values listed in table X below.

TABLE 73

(Iaba)

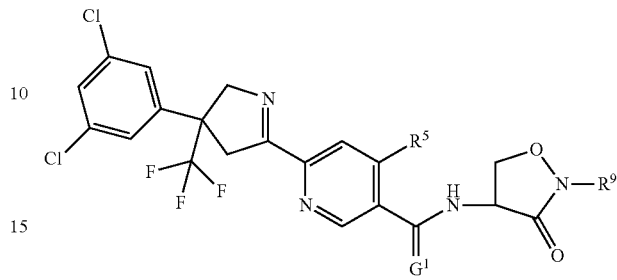

Table 73 provides 295 compounds of formula (Iaba) wherein $G^1$ is oxygen, and $R^5$ and $R^9$ have the values listed in table X below.

TABLE 74

(Ibba)

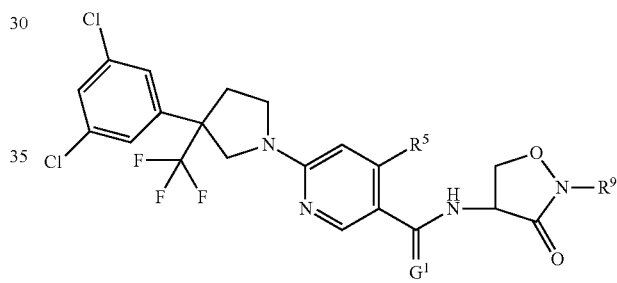

Table 74 provides 295 compounds of formula (Ibba) wherein $G^1$ is oxygen, and $R^5$ and $R^9$ have the values listed in table X below.

TABLE 75

(Iabb)

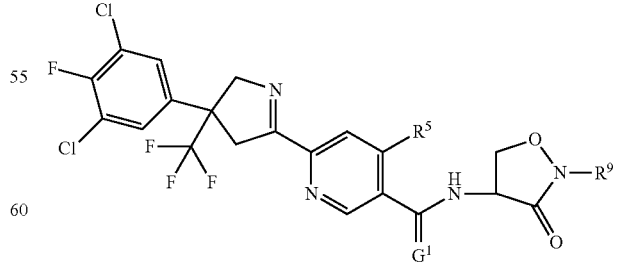

Table 75 provides 295 compounds of formula (Iabb) wherein $G^1$ is oxygen, and $R^5$ and $R^9$ have the values listed in table X below.

TABLE 76

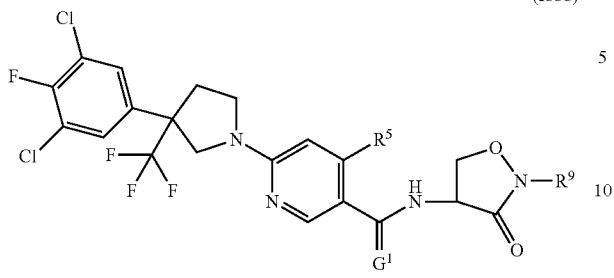

(Ibbb)

Table 76 provides 295 compounds of formula (Ibbb) wherein $G^1$ is oxygen, and $R^5$ and $R^9$ have the values listed in table X below.

TABLE 77

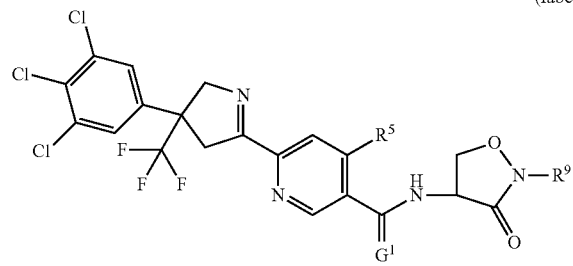

(Iabc)

Table 77 provides 295 compounds of formula (Iabc) wherein $G^1$ is oxygen, and $R^5$ and $R^9$ have the values listed in table X below.

TABLE 78

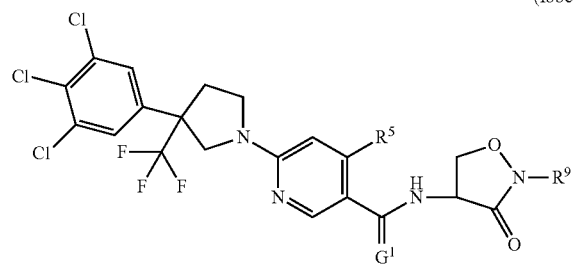

(Ibbc)

Table 78 provides 295 compounds of formula (Ibbc) wherein $G^1$ is oxygen, and $R^5$ and $R^9$ have the values listed in table X below.

TABLE 79

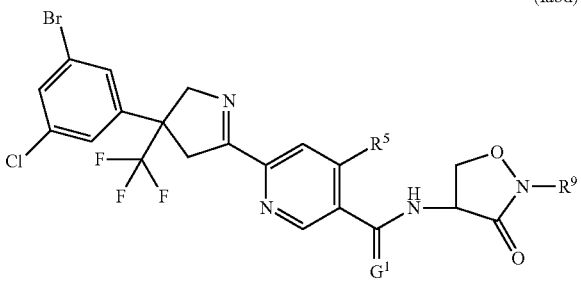

(Iabd)

Table 79 provides 295 compounds of formula (Iabd) wherein $G^1$ is oxygen, and $R^5$ and $R^9$ have the values listed in table X below.

TABLE 80

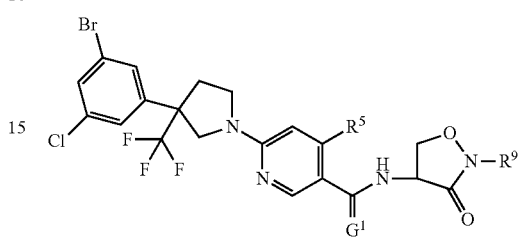

(Ibbd)

Table 80 provides 295 compounds of formula (Ibbd) wherein $G^1$ is oxygen, and $R^5$ and $R^9$ have the values listed in table X below.

TABLE 81

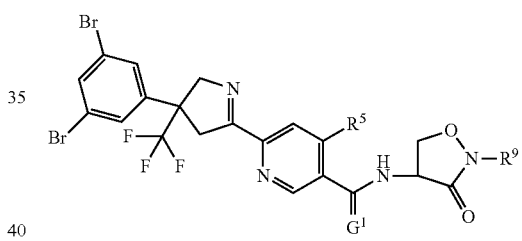

(Iabe)

Table 81 provides 295 compounds of formula (Iabe) wherein $G^1$ is oxygen, and $R^5$ and $R^9$ have the values listed in table X below.

TABLE 82

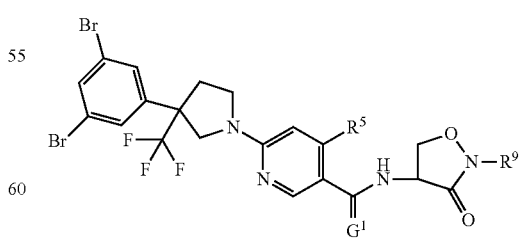

(Ibbe)

Table 82 provides 295 compounds of formula (Ibbe) wherein $G^1$ is oxygen, and $R^5$ and $R^9$ have the values listed in table X below.

TABLE 83

(Iabf)

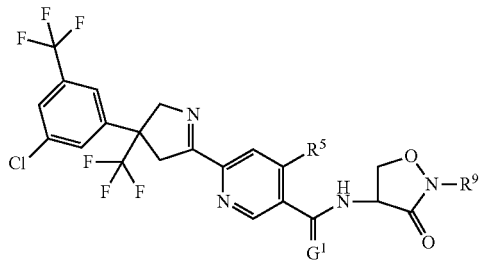

Table 83 provides 295 compounds of formula (Iabf) wherein $G^1$ is oxygen, and $R^5$ and $R^9$ have the values listed in table X below.

TABLE 84

(Ibbf)

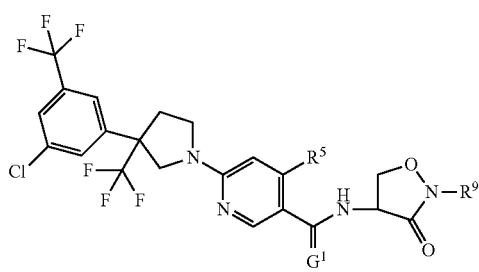

Table 84 provides 295 compounds of formula (Ibbf) wherein $G^1$ is oxygen, and $R^5$ and $R^9$ have the values listed in table X below.

TABLE 85

(Iabg)

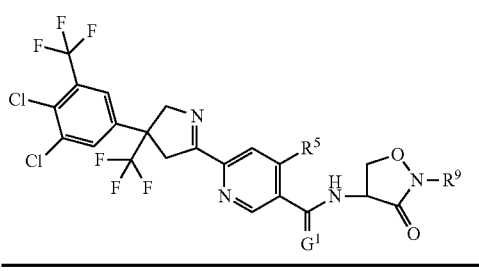

Table 85 provides 295 compounds of formula (Iabg) wherein $G^1$ is oxygen, and $R^5$ and $R^9$ have the values listed in table X below.

TABLE 86

(Ibbg)

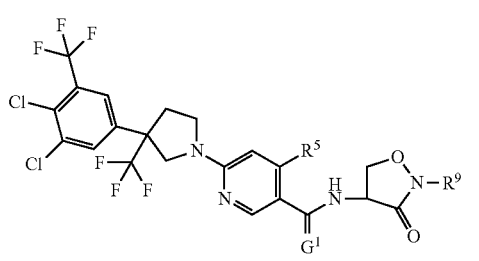

Table 86 provides 295 compounds of formula (Ibbg) wherein $G^1$ is oxygen, and $R^5$ and $R^9$ have the values listed in table X below.

TABLE 87

(Iabh)

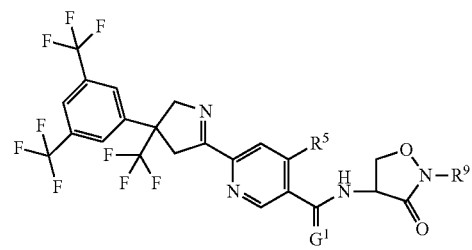

Table 87 provides 295 compounds of formula (Iabh) wherein $G^1$ is oxygen, and $R^5$ and $R^9$ have the values listed in table X below.

TABLE 88

(Ibbh)

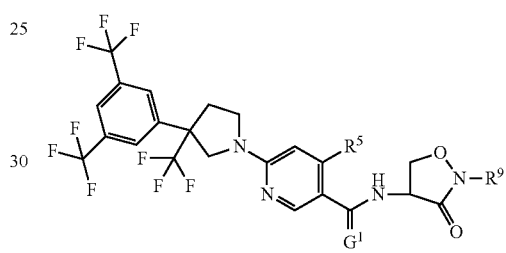

Table 88 provides 295 compounds of formula (Ibbh) wherein $G^1$ is oxygen, and $R^5$ and $R^9$ have the values listed in table X below.

TABLE 89

(Iabi)

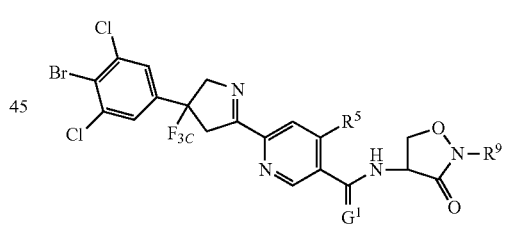

Table 89 provides 295 compounds of formula (Iabi) wherein $G^1$ is oxygen, and $R^5$ and $R^9$ have the values listed in table X below.

TABLE 90

(Ibbi)

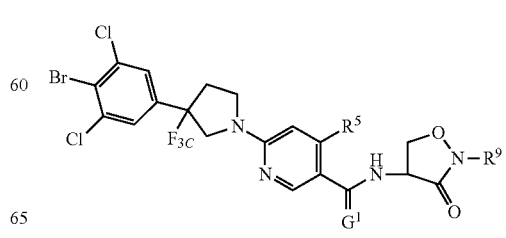

Table 90 provides 295 compounds of formula (Ibbi) wherein G¹ is oxygen, and R⁵ and R⁹ have the values listed in table X below.

TABLE 91

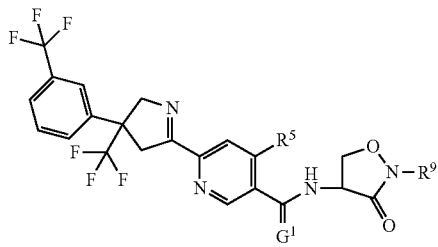

(Iabj)

Table 91 provides 295 compounds of formula (Iabj) wherein G¹ is oxygen, and R⁵ and R⁹ have the values listed in table X below.

TABLE 92

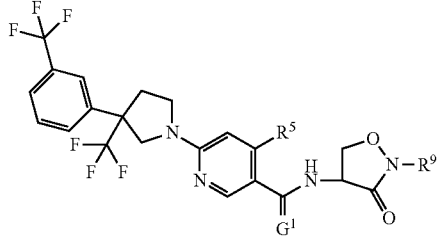

(Ibbi)

Table 92 provides 295 compounds of formula (Ibbi) wherein G¹ is oxygen, and R⁵ and R⁹ have the values listed in table X below.

TABLE 93

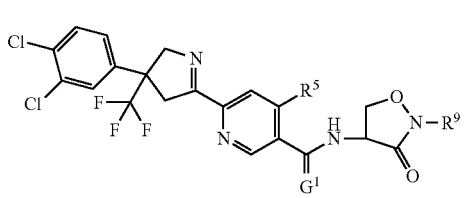

(Iabk)

Table 93 provides 295 compounds of formula (Iabk) wherein G¹ is oxygen, and R⁵ and R⁹ have the values listed in table X below.

TABLE 94

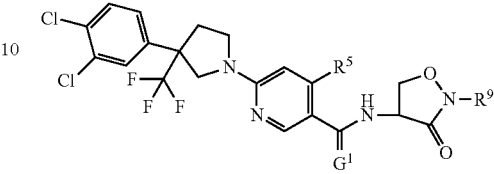

(Ibbk)

Table 94 provides 295 compounds of formula (Ibbk) wherein G¹ is oxygen, and R⁵ and R⁹ have the values listed in table X below.

TABLE 95

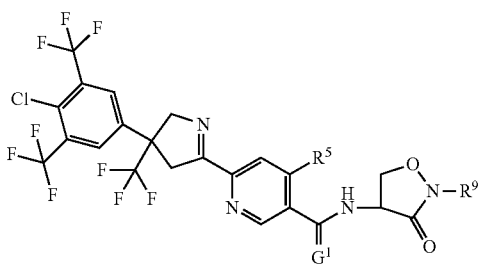

(Iabl)

Table 95 provides 295 compounds of formula (Iabl) wherein G¹ is oxygen, and R⁵ and R⁹ have the values listed in table X below.

TABLE 96

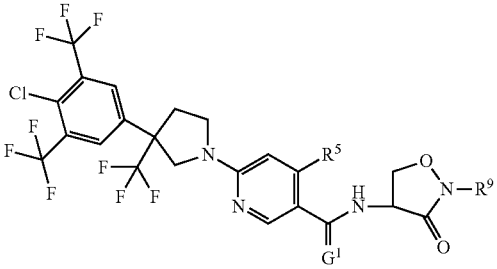

(Ibbl)

Table 96 provides 295 compounds of formula (Ibbl) wherein G¹ is oxygen, and R⁵ and R⁹ have the values listed in table X below.

TABLE 97

(Iaca)

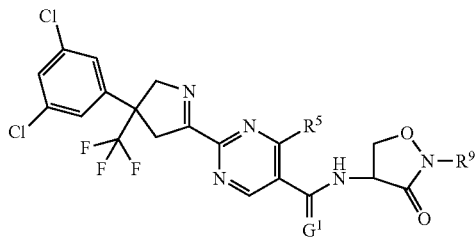

Table 97 provides 295 compounds of formula (Iaca) wherein $G^1$ is oxygen, and $R^5$ and $R^9$ have the values listed in table X below.

TABLE 98

(Ibca)

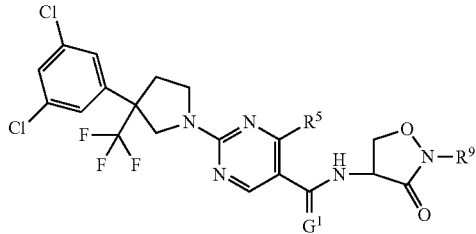

Table 98 provides 295 compounds of formula (Ibca) wherein $G^1$ is oxygen, and $R^5$ and $R^9$ have the values listed in table X below.

TABLE 99

(Iacb)

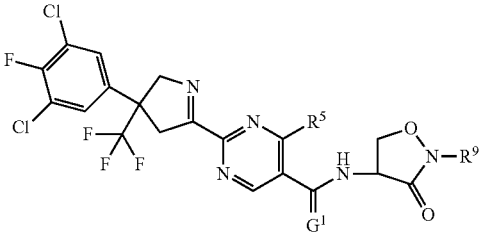

Table 99 provides 295 compounds of formula (Iacb) wherein $G^1$ is oxygen, and $R^5$ and $R^9$ have the values listed in table X below.

TABLE 100

(Ibcb)

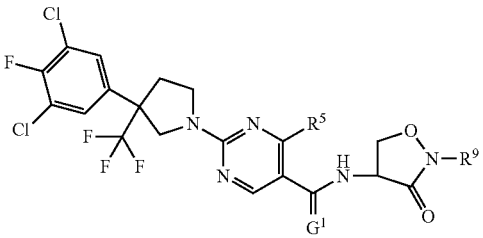

Table 100 provides 295 compounds of formula (Ibcb) wherein $G^1$ is oxygen, and $R^5$ and $R^9$ have the values listed in table X below.

TABLE 101

(Iacc)

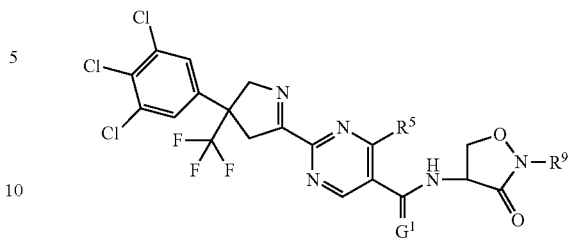

Table 101 provides 295 compounds of formula (Iacc) wherein $G^1$ is oxygen, and $R^5$ and $R^9$ have the values listed in table X below.

TABLE 102

(Ibcc)

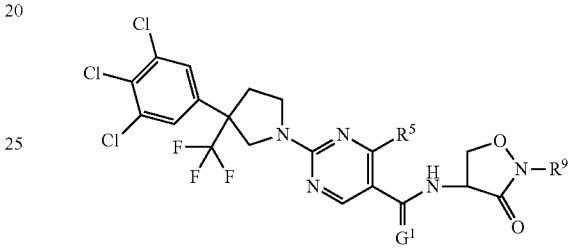

Table 102 provides 295 compounds of formula (Ibcc) wherein $G^1$ is oxygen, and $R^5$ and $R^9$ have the values listed in table X below.

TABLE 103

(Iacd)

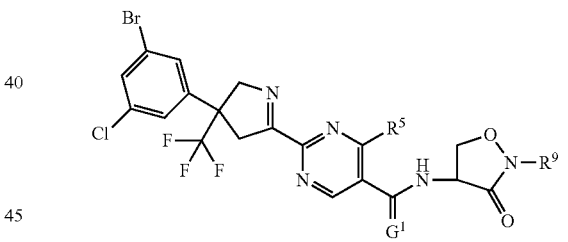

Table 103 provides 295 compounds of formula (Iacd) wherein $G^1$ is oxygen, and $R^5$ and $R^9$ have the values listed in table X below.

TABLE 104

(Ibcd)

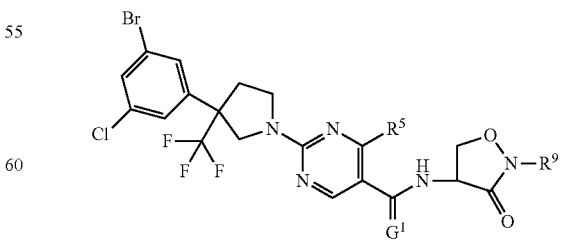

Table 104 provides 295 compounds f formula (Ibcd) wherein $G^1$ is oxygen, and $R^5$ and $R^9$ have the values listed in table X below.

TABLE 105

(Iace)

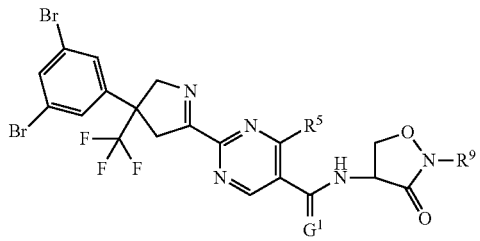

Table 105 provides 295 compounds of formula (Iace) wherein $G^1$ is oxygen, and $R^5$ and $R^9$ have the values listed in table X below.

TABLE 106

(Ibce)

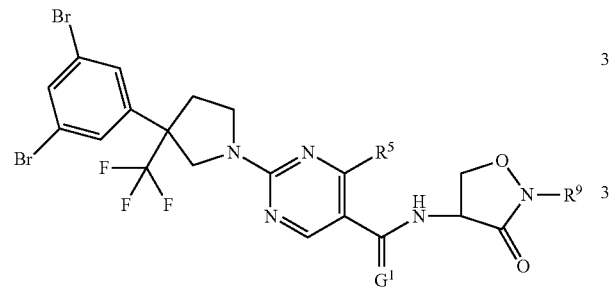

Table 106 provides 295 compounds of formula (Ibce) wherein $G^1$ is oxygen, and $R^5$ and $R^9$ have the values listed in table X below.

TABLE 107

(Iacf)

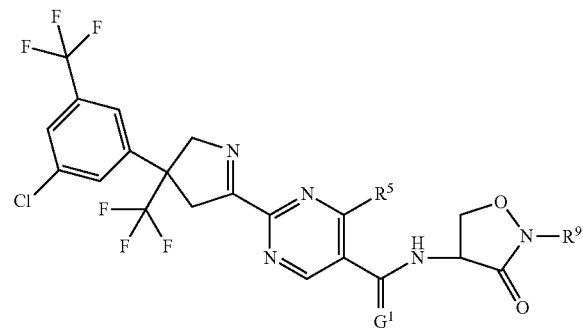

Table 107 provides 295 compounds of formula (Iacf) wherein $G^1$ is oxygen, and $R^5$ and $R^9$ have the values listed in table X below.

TABLE 108

(Ibcf)

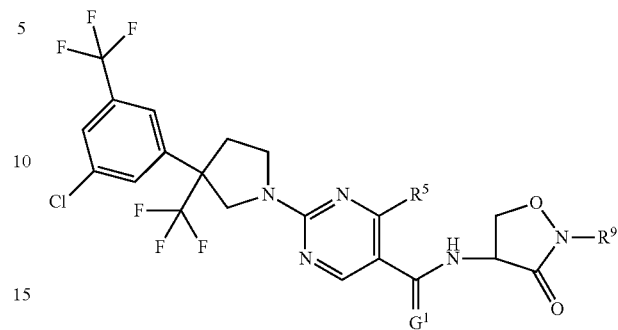

Table 108 provides 295 compounds of formula (Ibcf) wherein $G^1$ is oxygen, and $R^5$ and $R^9$ have the values listed in table X below.

TABLE 109

(Iacg)

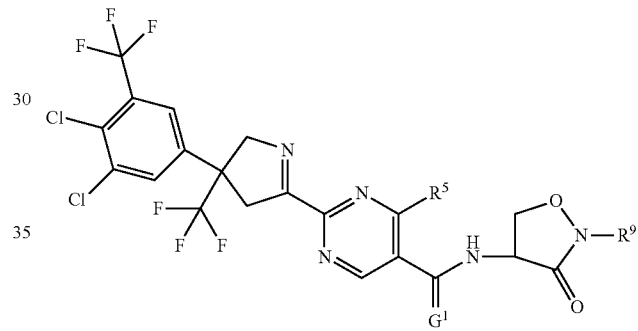

Table 109 provides 295 compounds of formula (Iacg) wherein $G^1$ is oxygen, and $R^5$ and $R^9$ have the values listed in table X below.

TABLE 110

(Ibcg)

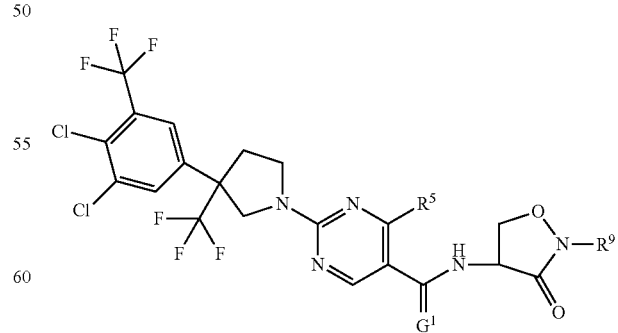

Table 110 provides 295 compounds of formula (Ibcg) wherein $G^1$ is oxygen, and $R^5$ and $R^9$ have the values listed in table X below.

TABLE 111

(Iach)

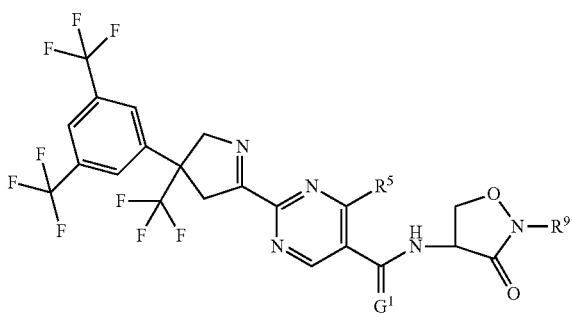

Table 111 provides 295 compounds of formula (Iach) wherein $G^1$ is oxygen, and $R^5$ and $R^9$ have the values listed in table X below.

TABLE 112

(Ibch)

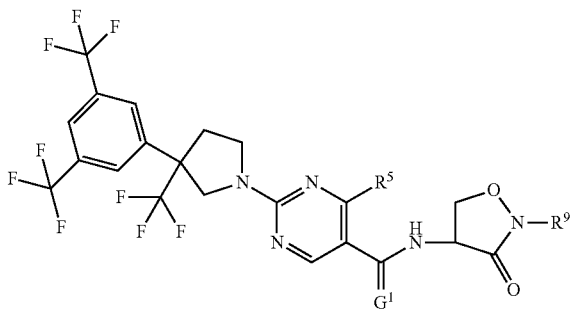

Table 112 provides 295 compounds of formula (Ibch) wherein $G^1$ is oxygen, and $R^5$ and $R^9$ have the values listed in table X below.

TABLE 113

(Iacl)

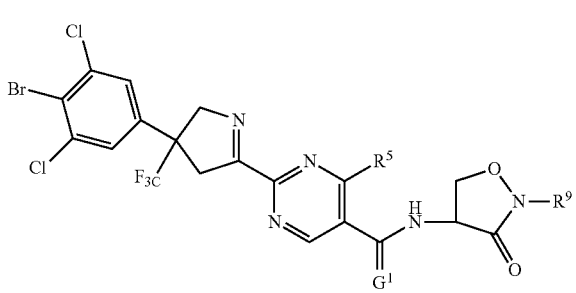

Table 113 provides 295 compounds of formula (IacI) wherein $G^1$ is oxygen, and $R^5$ and $R^9$ have the values listed in table X below.

TABLE 114

(Ibci)

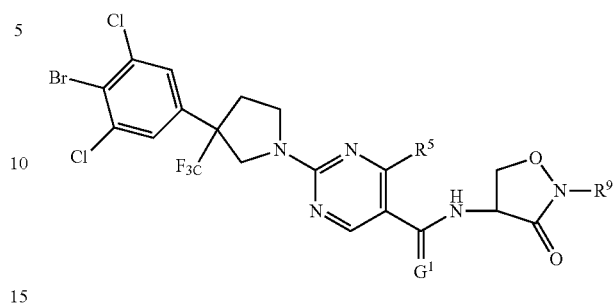

Table 114 provides 295 compounds of formula (Ibci) wherein $G^1$ is oxygen, and $R^5$ and $R^9$ have the values listed in table X below.

TABLE 115

(Iacj)

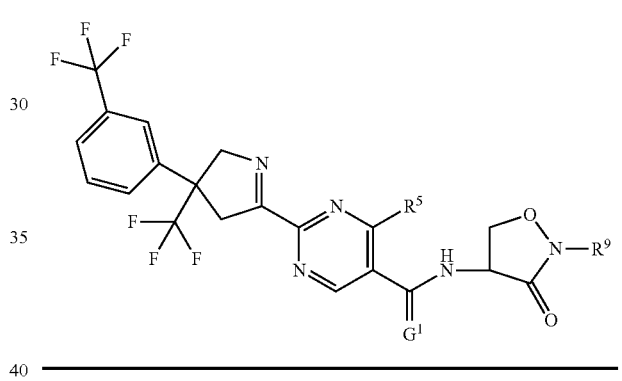

Table 115 provides 295 compounds of formula (Iacj) wherein $G^1$ is oxygen, and $R^5$ and $R^9$ have the values listed in table X below.

TABLE 116

(Ibci)

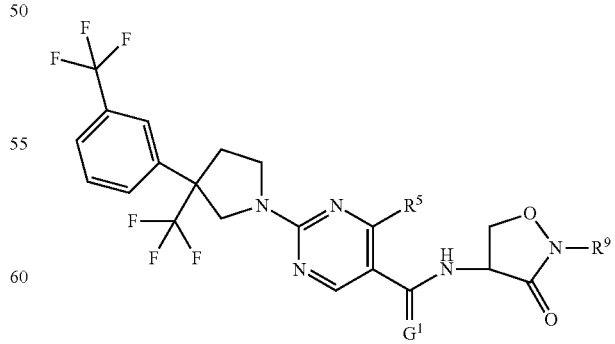

Table 116 provides 295 compounds of formula (Ibci) wherein $G^1$ is oxygen, and $R^5$ and $R^9$ have the values listed in table X below.

TABLE 117

(Iack)

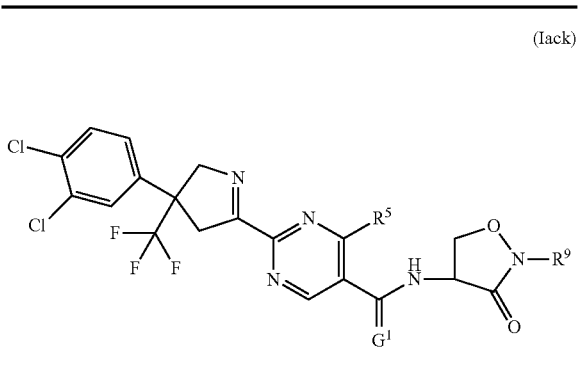

Table 117 provides 295 compounds of formula (Iack) wherein $G^1$ is oxygen, and $R^5$ and $R^9$ have the values listed in table X below.

TABLE 118

(Ibck)

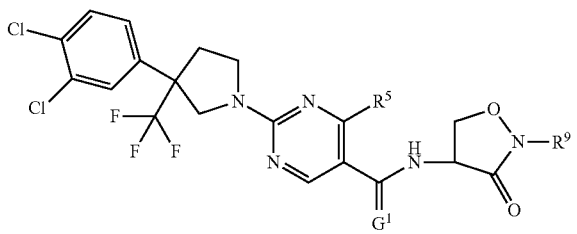

Table 118 provides 295 compounds of formula (Ibck) wherein $G^1$ is oxygen, and $R^5$ and $R^9$ have the values listed in table X below.

TABLE 119

(Iacl)

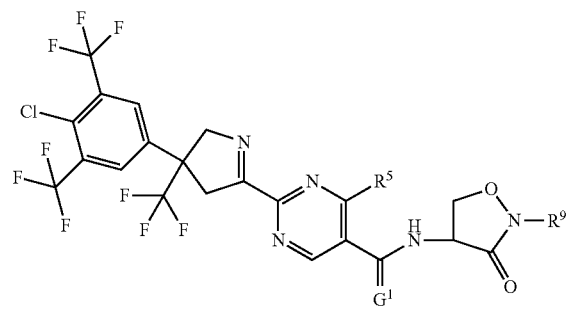

Table 119 provides 295 compounds of formula (Iacl) wherein $G^1$ is oxygen, and $R^5$ and $R^9$ have the values listed in table X below.

TABLE 120

(Ibcl)

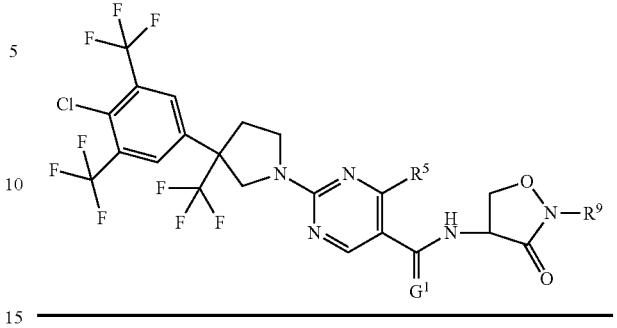

Table 120 provides 295 compounds of formula (Ibcl) wherein $G^1$ is oxygen, and $R^5$ and $R^9$ have the values listed in table X below.

Table X represents Table 1 when X is 1, Table 2 when X is 2, Table 3 when X is 3, Table 4 when X is 4, Table 5 when X is 5, Table 6 when X is 6, Table 7 when X is 7, Table 8 when X is 8, Table 9 when X is 9, Table 10 when X is 10, Table 11 when X is 11, Table 12 when X is 12, Table 13 when X is 13, Table 14 when X is 14, Table 15 when X is 15, Table 16 when X is 16, Table 17 when X is 17, Table 18 when X is 18, Table 19 when X is 19, Table 20 when X is 20, Table 21 when X is 21, Table 22 when X is 22, Table 23 when X is 23, Table 24 when X is 24, Table 25 when X is 25, Table 26 when X is 26, Table 27 when X is 27, Table 28 when X is 28, Table 29 when X is 29, Table 30 when X is 30, Table 31 when X is 31, Table 32 when X is 32, Table 33 when X is 33, Table 34 when X is 34, Table 35 when X is 35, Table 36 when X is 36, Table 37 when X is 37, Table 38 when X is 38, Table 39 when X is 39, Table 40 when X is 40, Table 41 when X is 41, Table 42 when X is 42, Table 43 when X is 43, Table 44 when X is 44, Table 45 when X is 45, Table 46 when X is 46, Table 47 when X is 47, Table 48 when X is 48, Table 49 when X is 49, Table 50 when X is 50, Table 51 when X is 51, Table 52 when X is 52, Table 53 when X is 53, Table 54 when X is 54, Table 55 when X is 55, Table 56 when X is 56, Table 57 when X is 57, Table 58 when X is 58, Table 59 when X is 59, Table 60 when X is 60, Table 61 when X is 61, Table 62 when X is 62, Table 63 when X is 63, Table 64 when X is 64, Table 65 when X is 65, Table 66 when X is 66, Table 67 when X is 67, Table 68 when X is 68, Table 69 when X is 69, Table 70 when X is 70, Table 71 when X is 71, Table 72 when X is 72, Table 73 when X is 73, Table 74 when X is 74, Table 75 when X is 75, Table 76 when X is 76, Table 77 when X is 77, Table 78 when X is 78, Table 79 when X is 79, Table 80 when X is 80, Table 81 when X is 81, Table 82 when X is 82, Table 83 when X is 83, Table 84 when X is 84, Table 85 when X is 85, Table 86 when X is 86, Table 87 when X is 87, Table 88 when X is 88, Table 89 when X is 89, Table 90 when X is 90, Table 91 when X is 91, Table 92 when X is 92, Table 93 when X is 93, Table 94 when X is 94, Table 95 when X is 95, Table 96 when X is 96, Table 97 when X is 97, Table 98 when X is 98, Table 99 when X is 99, Table 100 when X is 100, Table 101 when X is 101, Table 102 when X is 102, Table 103 when X is 103, Table 104 when X is 104, Table 105 when X is 105, Table 106 when X is 106, Table 107 when X is 107, Table 108 when X is 108, Table 109 when X is 109, Table 110 when X is 110, Table 111 when X is 111, Table 112 when X is 112, Table 113 when X is 113, Table 114 when X is 114, Table 115 when X is 115, Table 116 when X is 116, Table 117 when X is 117, Table 118 when X is 118, Table 119 when X is 119 and Table 120 when X is 120.

TABLE X

| Compound numbers | R⁵ | R⁹ |
|---|---|---|
| X.01 | methyl | ethyl- |
| X.02 | methyl | butyl- |
| X.03 | methyl | but-2-yl- |
| X.04 | methyl | 3-bromo-propyl- |
| X.05 | methyl | 2,2,2-trifluoro-ethyl- |
| X.06 | methyl | 3,3,3-trifluoro-propyl- |
| X.07 | methyl | 2-methoxy-ethyl- |
| X.08 | methyl | 1-methoxy-prop-2-yl- |
| X.09 | methyl | cyclobutyl- |
| X.10 | methyl | 2-methyl-cyclohex-1-yl- |
| X.11 | methyl | phenyl-methyl- |
| X.12 | methyl | 1-phenyl-eth-1-yl- |
| X.13 | methyl | 2-phenyl-eth-1-yl- |
| X.14 | methyl | (3-chloro-phenyl)-methyl- |
| X.15 | methyl | (2-fluoro-phenyl)-methyl- |
| X.16 | methyl | (4-methoxy-phenyl)-methyl- |
| X.17 | methyl | (2-trifluoromethyl-phenyl)-methyl- |
| X.18 | methyl | (2-trifluoromethoxy-phenyl)-methyl- |
| X.19 | methyl | (pyrid-2-yl)-methyl- |
| X.20 | methyl | (pyrid-3-yl)-methyl- |
| X.21 | methyl | (2-chloro-pyrid-5-yl)-methyl- |
| X.22 | methyl | (1-methyl-1H-imidazol-4-yl)-methyl- |
| X.23 | methyl | (furan-2-yl)-methyl- |
| X.24 | methyl | 2-(thiophen-2'-yl)-eth-1-yl- |
| X.25 | methyl | 2-(indol-3'-yl)-eth-1-yl- |
| X.26 | methyl | (1H-benzimidazol-2-yl)-methyl- |
| X.27 | methyl | (oxetan-2-yl)-methyl- |
| X.28 | methyl | (tetrahydrofuran-2-yl)-methyl- |
| X.29 | methyl | 2-([1',3']dioxolan-2'-yl)-eth-1-yl- |
| X.30 | methyl | 2-(morpholin-4'-yl)-eth-1-yl- |
| X.31 | methyl | 2-(benzo[1',3']dioxol-5'-yl)-eth-1-yl- |
| X.32 | methyl | (2,3-dihydro-benzo[1,4]dioxin-6-yl)-methyl- |
| X.33 | methyl | 2-chloro-phenyl- |
| X.34 | methyl | 3-fluoro-phenyl- |
| X.35 | methyl | 2-methyl-phenyl- |
| X.36 | methyl | 2-chloro-6-methyl-phenyl- |
| X.37 | methyl | 2-trifluoromethyl-phenyl- |
| X.38 | methyl | 2,4-dimethoxy-phenyl- |
| X.39 | methyl | 3-methyl-pyrid-2-yl- |
| X.40 | methyl | 1,3-dimethyl-1H-pyrazol-5-yl- |
| X.41 | methyl | 4-methyl-thiazol-2-yl- |
| X.42 | methyl | 5-methyl-thiadiazol-2-yl- |
| X.43 | methyl | quinolin-2-yl- |
| X.44 | methyl | quinolin-5-yl- |
| X.45 | methyl | benzothiazol-6-yl- |
| X.46 | methyl | 4-methyl-benzothiazol-2-yl- |
| X.47 | methyl | thietan-3-yl- |
| X.48 | methyl | 1-oxo-thietan-3-yl- |
| X.49 | methyl | 1,1-dioxo-thietan-3-yl- |
| X.50 | methyl | 3-methyl-thietan-3-yl- |
| X.51 | methyl | oxetan-3yl |
| X.52 | methyl | tetrahydropyran-4-yl |
| X.53 | methyl | hydrogen |
| X.54 | methyl | methyl |
| X.55 | methyl | propyl |
| X.56 | methyl | 2,2-difluoro-ethyl- |
| X.57 | methyl | 2-fluoro-ethyl- |
| X.58 | methyl | Isopropyl |
| X.59 | methyl | cyclopropyl |
| X.60 | chloro | but-2-yl- |
| X.61 | chloro | 3-bromo-propyl- |
| X.62 | chloro | 2,2,2-trifluoro-ethyl- |
| X.63 | chloro | 3,3,3-trifluoro-propyl- |
| X.64 | chloro | 2-methoxy-ethyl- |
| X.65 | chloro | 1-methoxy-prop-2-yl- |
| X.66 | chloro | cyclobutyl- |
| X.67 | chloro | 2-methyl-cyclohex-1-yl- |
| X.68 | chloro | phenyl-methyl- |
| X.69 | chloro | 1-phenyl-eth-1-yl- |
| X.70 | chloro | 2-phenyl-eth-1-yl- |
| X.71 | chloro | (3-chloro-phenyl)-methyl- |
| X.72 | chloro | (2-fluoro-phenyl)-methyl- |
| X.73 | chloro | (4-methoxy-phenyl)-methyl- |
| X.74 | chloro | (2-trifluoromethyl-phenyl)-methyl- |
| X.75 | chloro | (2-trifluoromethoxy-phenyl)-methyl- |
| X.76 | chloro | (pyrid-2-yl)-methyl- |
| X.77 | chloro | (pyrid-3-yl)-methyl- |
| X.78 | chloro | (2-chloro-pyrid-5-yl)-methyl- |
| X.79 | chloro | (1-methyl-1H-imidazol-4-yl)-methyl- |
| X.80 | chloro | (furan-2-yl)-methyl- |
| X.81 | chloro | 2-(thiophen-2'-yl)-eth-1-yl- |
| X.82 | chloro | 2-(indol-3'-yl)-eth-1-yl- |
| X.83 | chloro | (1H-benzimidazol-2-yl)-methyl- |
| X.84 | chloro | (oxetan-2-yl)-methyl- |
| X.85 | chloro | (tetrahydrofuran-2-yl)-methyl- |
| X.86 | chloro | 2-([1',3']dioxolan-2'-yl)-eth-1-yl- |
| X.87 | chloro | 2-(morpholin-4'-yl)-eth-1-yl- |
| X.88 | chloro | 2-(benzo[1',3']dioxol-5'-yl)-eth-1-yl- |
| X.89 | chloro | (2,3-dihydro-benzo[1,4]dioxin-6-yl)-methyl- |
| X.90 | chloro | 2-chloro-phenyl- |
| X.91 | chloro | 3-fluoro-phenyl- |
| X.92 | chloro | 2-methyl-phenyl- |
| X.93 | chloro | 2-chloro-6-methyl-phenyl- |
| X.94 | chloro | 2-trifluoromethyl-phenyl- |
| X.95 | chloro | 2,4-dimethoxy-phenyl- |
| X.96 | chloro | 3-methyl-pyrid-2-yl- |
| X.97 | chloro | 1,3-dimethyl-1H-pyrazol-5-yl- |
| X.98 | chloro | 4-methyl-thiazol-2-yl- |
| X.99 | chloro | 5-methyl-thiadiazol-2-yl- |
| X.100 | chloro | quinolin-2-yl- |
| X.101 | chloro | quinolin-5-yl- |
| X.102 | chloro | benzothiazol-6-yl- |
| X.103 | chloro | 4-methyl-benzothiazol-2-yl- |
| X.104 | chloro | thietan-3-yl- |
| X.105 | chloro | 1-oxo-thietan-3-yl- |
| X.106 | chloro | 1,1-dioxo-thietan-3-yl- |
| X.107 | chloro | 3-methyl-thietan-3-yl- |
| X.108 | chloro | oxetan-3yl |
| X.109 | chloro | tetrahydropyran-4-yl |
| X.110 | chloro | hydrogen |
| X.111 | chloro | methyl |
| X.112 | chloro | propyl |
| X.113 | chloro | 2,2-difluoro-ethyl- |
| X.114 | chloro | 2-fluoro-ethyl- |
| X.115 | chloro | ethyl- |
| X.116 | chloro | butyl- |
| X.117 | chloro | Isopropyl |
| X.118 | chloro | cyclopropyl |
| X.119 | trifluoromethyl | ethyl- |
| X.120 | trifluoromethyl | butyl- |
| X.121 | trifluoromethyl | but-2-yl- |
| X.122 | trifluoromethyl | 3-bromo-propyl- |
| X.123 | trifluoromethyl | 2,2,2-trifluoro-ethyl- |
| X.124 | trifluoromethyl | 3,3,3-trifluoro-propyl- |
| X.125 | trifluoromethyl | 2-methoxy-ethyl- |
| X.126 | trifluoromethyl | 1-methoxy-prop-2-yl- |
| X.127 | trifluoromethyl | cyclobutyl- |
| X.128 | trifluoromethyl | 2-methyl-cyclohex-1-yl- |
| X.129 | trifluoromethyl | phenyl-methyl- |
| X.130 | trifluoromethyl | 1-phenyl-eth-1-yl- |
| X.131 | trifluoromethyl | 2-phenyl-eth-1-yl- |
| X.132 | trifluoromethyl | (3-chloro-phenyl)-methyl- |
| X.133 | trifluoromethyl | (2-fluoro-phenyl)-methyl- |
| X.134 | trifluoromethyl | (4-methoxy-phenyl)-methyl- |
| X.135 | trifluoromethyl | (2-trifluoromethyl-phenyl)-methyl- |
| X.136 | trifluoromethyl | (2-trifluoromethoxy-phenyl)-methyl- |
| X.137 | trifluoromethyl | (pyrid-2-yl)-methyl- |
| X.138 | trifluoromethyl | (pyrid-3-yl)-methyl- |
| X.139 | trifluoromethyl | (2-chloro-pyrid-5-yl)-methyl- |
| X.140 | trifluoromethyl | (1-methyl-1H-imidazol-4-yl)-methyl- |
| X.141 | trifluoromethyl | (furan-2-yl)-methyl- |
| X.142 | trifluoromethyl | 2-(thiophen-2'-yl)-eth-1-yl- |
| X.143 | trifluoromethyl | 2-(indol-3'-yl)-eth-1-yl- |
| X.144 | trifluoromethyl | (1H-benzimidazol-2-yl)-methyl- |
| X.145 | trifluoromethyl | (oxetan-2-yl)-methyl- |
| X.146 | trifluoromethyl | (tetrahydrofuran-2-yl)-methyl- |
| X.147 | trifluoromethyl | 2-([1',3']dioxolan-2'-yl)-eth-1-yl- |

TABLE X-continued

| Compound numbers | R⁵ | R⁹ |
|---|---|---|
| X.148 | trifluoromethyl | 2-(morpholin-4'-yl)-eth-1-yl- |
| X.149 | trifluoromethyl | 2-(benzo[1',3']dioxol-5'-yl)-eth-1-yl- |
| X.150 | trifluoromethyl | (2,3-dihydro-benzo[1,4]dioxin-6-yl)-methyl- |
| X.151 | trifluoromethyl | 2-chloro-phenyl- |
| X.152 | trifluoromethyl | 3-fluoro-phenyl- |
| X.153 | trifluoromethyl | 2-methyl-phenyl- |
| X.154 | trifluoromethyl | 2-chloro-6-methyl-phenyl- |
| X.155 | trifluoromethyl | 2-trifluoromethyl-phenyl- |
| X.156 | trifluoromethyl | 2,4-dimethoxy-phenyl- |
| X.157 | trifluoromethyl | 3-methyl-pyrid-2-yl- |
| X.158 | trifluoromethyl | 1,3-dimethyl-1H-pyrazol-5-yl- |
| X.159 | trifluoromethyl | 4-methyl-thiazol-2-yl- |
| X.160 | trifluoromethyl | 5-methyl-thiadiazol-2-yl- |
| X.161 | trifluoromethyl | quinolin-2-yl- |
| X.162 | trifluoromethyl | quinolin-5-yl- |
| X.163 | trifluoromethyl | benzothiazol-6-yl- |
| X.164 | trifluoromethyl | 4-methyl-benzothiazol-2-yl- |
| X.165 | trifluoromethyl | thietan-3-yl- |
| X.166 | trifluoromethyl | 1-oxo-thietan-3-yl- |
| X.167 | trifluoromethyl | 1,1-dioxo-thietan-3-yl- |
| X.168 | trifluoromethyl | 3-methyl-thietan-3-yl- |
| X.169 | trifluoromethyl | oxetan-3yl |
| X.170 | trifluoromethyl | tetrahydropyran-4-yl |
| X.171 | trifluoromethyl | hydrogen |
| X.172 | trifluoromethyl | methyl |
| X.173 | trifluoromethyl | propyl |
| X.174 | trifluoromethyl | 2,2-difluoro-ethyl- |
| X.175 | trifluoromethyl | 2-fluoro-ethyl- |
| X.176 | trifluoromethyl | Isopropyl |
| X.177 | trifluoromethyl | cyclopropyl |
| X.178 | bromo | but-2-yl- |
| X.179 | bromo | 3-bromo-propyl- |
| X.180 | bromo | 2,2,2-trifluoro-ethyl- |
| X.181 | bromo | 3,3,3-trifluoro-propyl- |
| X.182 | bromo | 2-methoxy-ethyl- |
| X.183 | bromo | 1-methoxy-prop-2-yl- |
| X.184 | bromo | cyclobutyl- |
| X.185 | bromo | 2-methyl-cyclohex-1-yl- |
| X.186 | bromo | phenyl-methyl- |
| X.187 | bromo | 1-phenyl-eth-1-yl- |
| X.188 | bromo | 2-phenyl-eth-1-yl- |
| X.189 | bromo | (3-chloro-phenyl)-methyl- |
| X.190 | bromo | (2-fluoro-phenyl)-methyl- |
| X.191 | bromo | (4-methoxy-phenyl)-methyl- |
| X.192 | bromo | (2-trifluoromethyl-phenyl)-methyl- |
| X.193 | bromo | (2-trifluoromethoxy-phenyl)-methyl- |
| X.194 | bromo | (pyrid-2-yl)-methyl- |
| X.195 | bromo | (pyrid-3-yl)-methyl- |
| X.196 | bromo | (2-chloro-pyrid-5-yl)-methyl- |
| X.197 | bromo | (1-methyl-1H-imidazol-4-yl)-methyl- |
| X.198 | bromo | (furan-2-yl)-methyl- |
| X.199 | bromo | 2-(thiophen-2'-yl)-eth-1-yl- |
| X.200 | bromo | 2-(indol-3'-yl)-eth-1-yl- |
| X.201 | bromo | (1H-benzimidazol-2-yl)-methyl- |
| X.202 | bromo | (oxetan-2-yl)-methyl- |
| X.203 | bromo | (tetrahydrofuran-2-yl)-methyl- |
| X.204 | bromo | 2-([1',3']dioxolan-2'-yl)-eth-1-yl- |
| X.205 | bromo | 2-(morpholin-4'-yl)-eth-1-yl- |
| X.206 | bromo | 2-(benzo[1',3']dioxol-5'-yl)-eth-1-yl- |
| X.207 | bromo | (2,3-dihydro-benzo[1,4]dioxin-6-yl)-methyl- |
| X.208 | bromo | 2-chloro-phenyl- |
| X.209 | bromo | 3-fluoro-phenyl- |
| X.210 | bromo | 2-methyl-phenyl- |
| X.211 | bromo | 2-chloro-6-methyl-phenyl- |
| X.212 | bromo | 2-trifluoromethyl-phenyl- |
| X.213 | bromo | 2,4-dimethoxy-phenyl- |
| X.214 | bromo | 3-methyl-pyrid-2-yl- |
| X.215 | bromo | 1,3-dimethyl-1H-pyrazol-5-yl- |
| X.216 | bromo | 4-methyl-thiazol-2-yl- |
| X.217 | bromo | 5-methyl-thiadiazol-2-yl- |
| X.218 | bromo | quinolin-2-yl- |
| X.219 | bromo | quinolin-5-yl- |
| X.220 | bromo | benzothiazol-6-yl- |
| X.221 | bromo | 4-methyl-benzothiazol-2-yl- |
| X.222 | bromo | thietan-3-yl- |
| X.223 | bromo | 1-oxo-thietan-3-yl- |
| X.224 | bromo | 1,1-dioxo-thietan-3-yl- |
| X.225 | bromo | 3-methyl-thietan-3-yl- |
| X.226 | bromo | oxetan-3yl |
| X.227 | bromo | tetrahydropyran-4-yl |
| X.228 | bromo | hydrogen |
| X.229 | bromo | methyl |
| X.230 | bromo | propyl |
| X.231 | bromo | 2,2-difluoro-ethyl- |
| X.232 | bromo | 2-fluoro-ethyl- |
| X.233 | bromo | ethyl- |
| X.234 | bromo | butyl- |
| X.235 | bromo | Isopropyl |
| X.236 | bromo | cyclopropyl |
| X.237 | fluoro | ethyl- |
| X.238 | fluoro | butyl- |
| X.239 | fluoro | but-2-yl- |
| X.240 | fluoro | 3-bromo-propyl- |
| X.241 | fluoro | 2,2,2-trifluoro-ethyl- |
| X.242 | fluoro | 3,3,3-trifluoro-propyl- |
| X.243 | fluoro | 2-methoxy-ethyl- |
| X.244 | fluoro | 1-methoxy-prop-2-yl- |
| X.245 | fluoro | cyclobutyl- |
| X.246 | fluoro | 2-methyl-cyclohex-1-yl- |
| X.247 | fluoro | phenyl-methyl- |
| X.248 | fluoro | 1-phenyl-eth-1-yl- |
| X.249 | fluoro | 2-phenyl-eth-1-yl- |
| X.250 | fluoro | (3-chloro-phenyl)-methyl- |
| X.251 | fluoro | (2-fluoro-phenyl)-methyl- |
| X.252 | fluoro | (4-methoxy-phenyl)-methyl- |
| X.253 | fluoro | (2-trifluoromethyl-phenyl)-methyl- |
| X.254 | fluoro | (2-trifluoromethoxy-phenyl)-methyl- |
| X.255 | fluoro | (pyrid-2-yl)-methyl- |
| X.256 | fluoro | (pyrid-3-yl)-methyl- |
| X.257 | fluoro | (2-chloro-pyrid-5-yl)-methyl- |
| X.258 | fluoro | (1-methyl-1H-imidazol-4-yl)-methyl- |
| X.259 | fluoro | (furan-2-yl)-methyl- |
| X.260 | fluoro | 2-(thiophen-2'-yl)-eth-1-yl- |
| X.261 | fluoro | 2-(indol-3'-yl)-eth-1-yl- |
| X.262 | fluoro | (1H-benzimidazol-2-yl)-methyl- |
| X.263 | fluoro | (oxetan-2-yl)-methyl- |
| X.264 | fluoro | (tetrahydrofuran-2-yl)-methyl- |
| X.265 | fluoro | 2-([1',3']dioxolan-2'-yl)-eth-1-yl- |
| X.266 | fluoro | 2-(morpholin-4'-yl)-eth-1-yl- |
| X.267 | fluoro | 2-(benzo[1',3']dioxol-5'-yl)-eth-1-yl- |
| X.268 | fluoro | (2,3-dihydro-benzo[1,4]dioxin-6-yl)-methyl- |
| X.269 | fluoro | 2-chloro-phenyl- |
| X.270 | fluoro | 3-fluoro-phenyl- |
| X.271 | fluoro | 2-methyl-phenyl- |
| X.272 | fluoro | 2-chloro-6-methyl-phenyl- |
| X.273 | fluoro | 2-trifluoromethyl-phenyl- |
| X.274 | fluoro | 2,4-dimethoxy-phenyl- |
| X.275 | fluoro | 3-methyl-pyrid-2-yl- |
| X.276 | fluoro | 1,3-dimethyl-1H-pyrazol-5-yl- |
| X.277 | fluoro | 4-methyl-thiazol-2-yl- |
| X.278 | fluoro | 5-methyl-thiadiazol-2-yl- |
| X.279 | fluoro | quinolin-2-yl- |
| X.280 | fluoro | quinolin-5-yl- |
| X.281 | fluoro | benzothiazol-6-yl- |
| X.282 | fluoro | 4-methyl-benzothiazol-2-yl- |
| X.283 | fluoro | thietan-3-yl- |
| X.284 | fluoro | 1-oxo-thietan-3-yl- |
| X.285 | fluoro | 1,1-dioxo-thietan-3-yl- |
| X.286 | fluoro | 3-methyl-thietan-3-yl- |
| X.287 | fluoro | oxetan-3yl |
| X.288 | fluoro | tetrahydropyran-4-yl |
| X.289 | fluoro | hydrogen |
| X.290 | fluoro | methyl |
| X.291 | fluoro | propyl |
| X.292 | fluoro | 2,2-difluoro-ethyl- |
| X.293 | fluoro | 2-fluoro-ethyl- |
| X.294 | fluoro | Isopropyl |
| X.295 | fluoro | cyclopropyl |

Compounds of formula I include at least one chiral centre and may exist as compounds of formula I* or compounds of formula I**. Compounds I* and I** are enantiomers if there is no other chiral center or epimers otherwise.

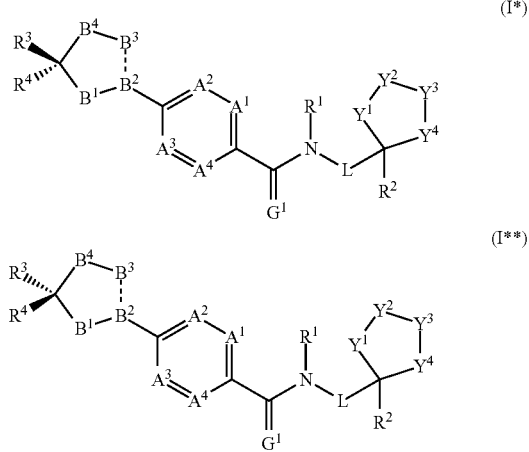

Generally compounds of formula I** are more biologically active than compounds of formula I*. The invention includes mixtures of compounds I* and I in any ratio e.g. in a molar ratio of 1:99 to 99:1, e.g. 10:1 to 1:10, e.g. a substantially 50:50 molar ratio. In an enantiomerically (or epimerically) enriched mixture of formula I, the molar proportion of compound I** compared to the total amount of both enantiomers is for example greater than 50%, e.g. at least 55, 60, 65, 70, 75, 80, 85, 90, 95, 96, 97, 98, or at least 99%. Likewise, in enantiomerically (or epimerically) enriched mixture of formula I*, the molar proportion of the compound of formula I* compared to the total amount of both enantiomers (or epimerically) is for example greater than 50%, e.g. at least 55, 60, 65, 70, 75, 80, 85, 90, 95, 96, 97, 98, or at least 99%. Enantiomerically (or epimerically) enriched mixtures of formula I** are preferred. Each compound shown in Tables 1 to 120 represents a specific disclosure of a compound according to formula I* as well as specific disclosure of a compound according to formula I**.

The compounds of the invention may be made by a variety of methods as shown in Schemes 1 to 15.

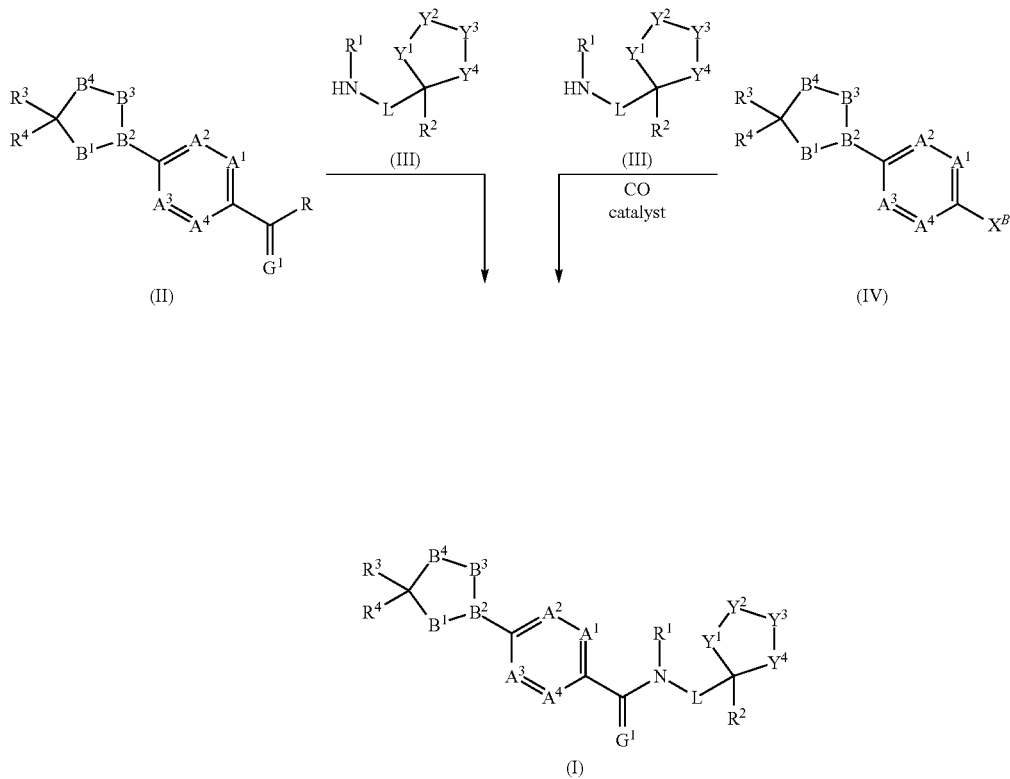

1) Compounds of formula (I) wherein $G^1$ is oxygen, can be prepared by reacting a compound of formula (II) wherein $G^1$ is oxygen and R is OH, $C_1$-$C_6$alkoxy or Cl, F or Br, with an amine of formula (III) as shown in Scheme 1. When R is OH such reactions are usually carried out in the presence of a coupling reagent, such as N,N'-dicyclohexylcarbodiimide ("DCC"), 1-ethyl-3-(3-dimethylamino-propyl)-carbodiimide hydrochloride ("EDC") or bis(2-oxo-3-oxazolidinyl)phosphonic chloride ("BOP—Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula (III) are either known in the literature or can be prepared using methods known to a person skilled in the art. Some of these methods are described in the preparation examples.

2) Acid halides of formula (II), wherein $G^1$ is oxygen and R is Cl, F or Br, may be made from carboxylic acids of formula (II), wherein $G^1$ is oxygen and R is OH, under standard conditions, as described for example in WO2008/128711

3) Carboxylic acids of formula (II), wherein $G^1$ is oxygen and R is OH, may be formed from esters of formula (II), wherein $G^1$ is oxygen and R is $C_1$-$C_6$alkoxy as described for example in WO2008128711 (when $B^1$—$B^2$—$B^3$—$B^4$ is $CH_2$—N—$CH_2$—$CH_2$—) and WO2009/072621 (when $B^1$—$B^2$—$B^3$—$B^4$ is —$CH_2$—C=N—$CH_2$—) and as described below (when $B^1$—$B^2$—$B^3$—$B^4$ is —$CH_2$—C=CH—O— or —CH=C—$CH_2$—O—).

4) Compounds of formula (I) wherein $G^1$ is oxygen, can be prepared by reacting a compound of formula (IV) wherein $X^B$ is a leaving group, for example a halogen, such as bromo, with carbon monoxide and an amine of formula (III), in the presence of a catalyst, such as palladium(II) acetate or bis-(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

5) Compounds of formula (IV) wherein $X^B$ is a leaving group, for example a halogen, such as bromo, can be made by a various of methods, for example as described in WO2009/080250.

6) Compounds of formula (I), wherein $G^1$ is sulfur, may be made by treatment of a compound of formula (II), wherein $G^1$ is oxygen and R is OH, $C_1$-$C_6$alkoxy or Cl, F or Br, with a thio-transfer reagent such as Lawesson's reagent or phosphorus pentasulfide prior to elaborating to compounds of formula (I), as described under 1).

In all the following schemes, $A^1$, $A^2$, $A^3$ and $A^4$ are as described for compounds of formula (I), and P can be a leaving group, for example a halogen, such as bromo, iodo, chloro or described by one of the two groups A and B:

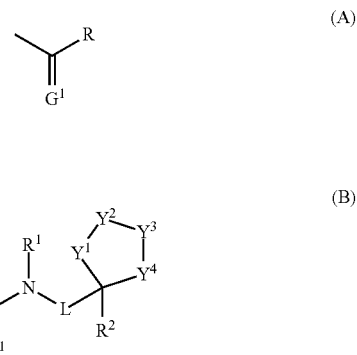

wherein $G^1$ is oxygen and R is OH, $C_1$-$C_{12}$alkoxy or Cl, F or Br, and $R^1$, $R^2$, L, $Y^1$, $Y^2$, $Y^3$ and $Y^4$ are as described for compounds of formula (I).

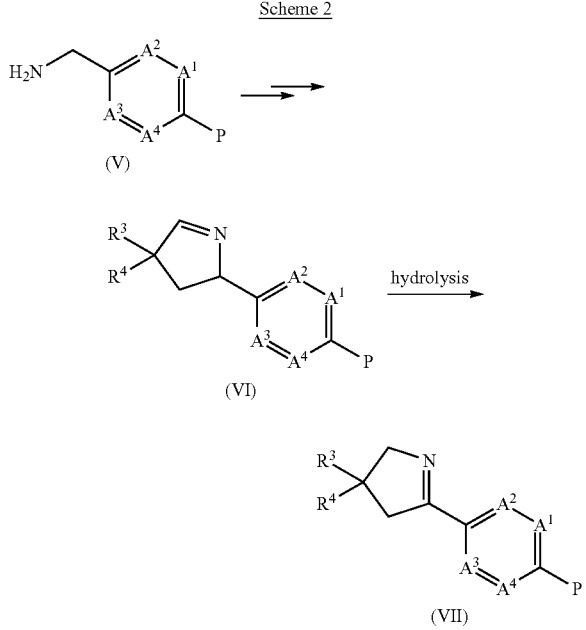

7) Alternatively, compounds of formula (VII) can be prepared by various methods from an intermediate of formula (VI) as shown in Scheme 2 according to similar methods to those described in WO2010/149506. An intermediate of formula (VI) can be prepared for example from an intermediate of formula (V) as described in the same reference.

Scheme 3

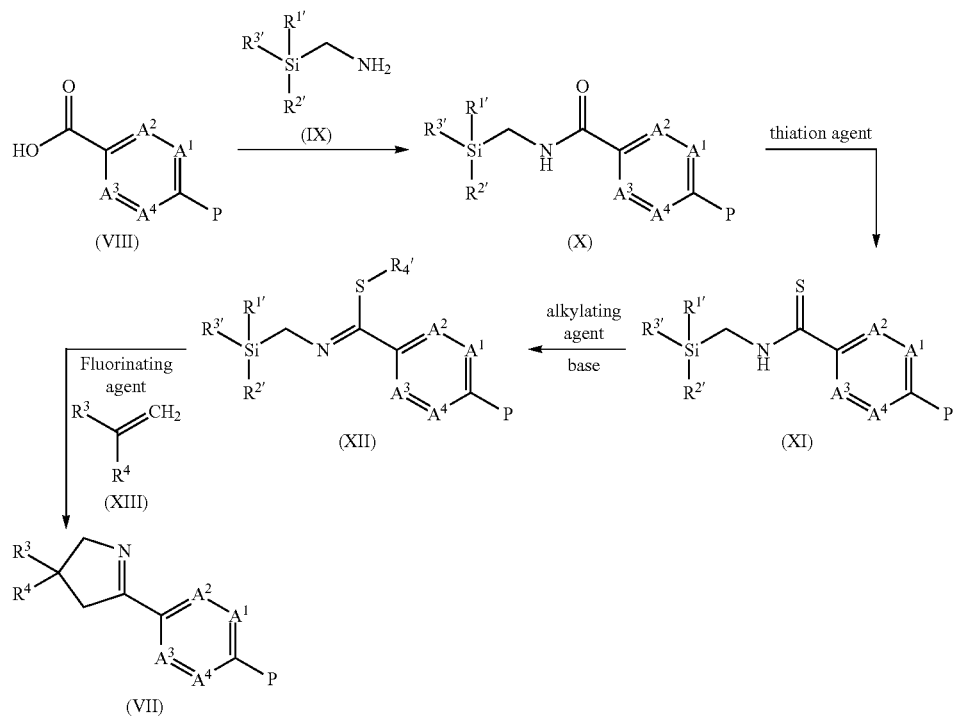

8) Alternatively, compounds of formula (VII) can be prepared by various methods from an intermediate of formula (XII) as shown in Scheme 3 according to similar methods to those described in WO2010/149506. The intermediates of formula (XII) can be prepared for example as described in the same reference.

Scheme 4

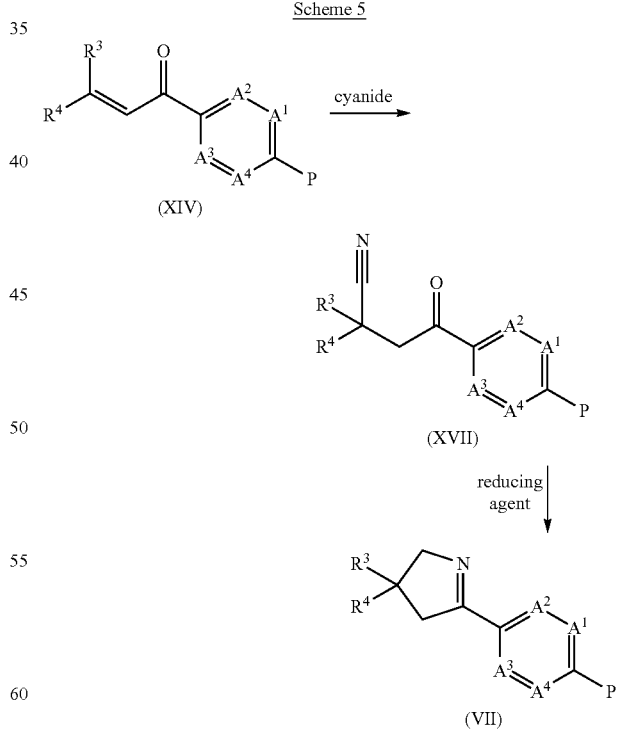

9) Alternatively, compounds of formula (VII) can be prepared by various methods from an intermediate of formula (XV) or (XVI) as shown in Scheme 4 according to similar methods to those described in WO20/10149506. The intermediates of formula (XV) can be prepared for example as described in the same reference.

10) Alternatively, compounds of formula (VII) can be prepared by various methods from an intermediate of formula (XVII) as shown in Scheme 5 according to similar methods to those described in WO20/10149506. The intermediates of formula (XVII) can be prepared for example as described in the same reference.

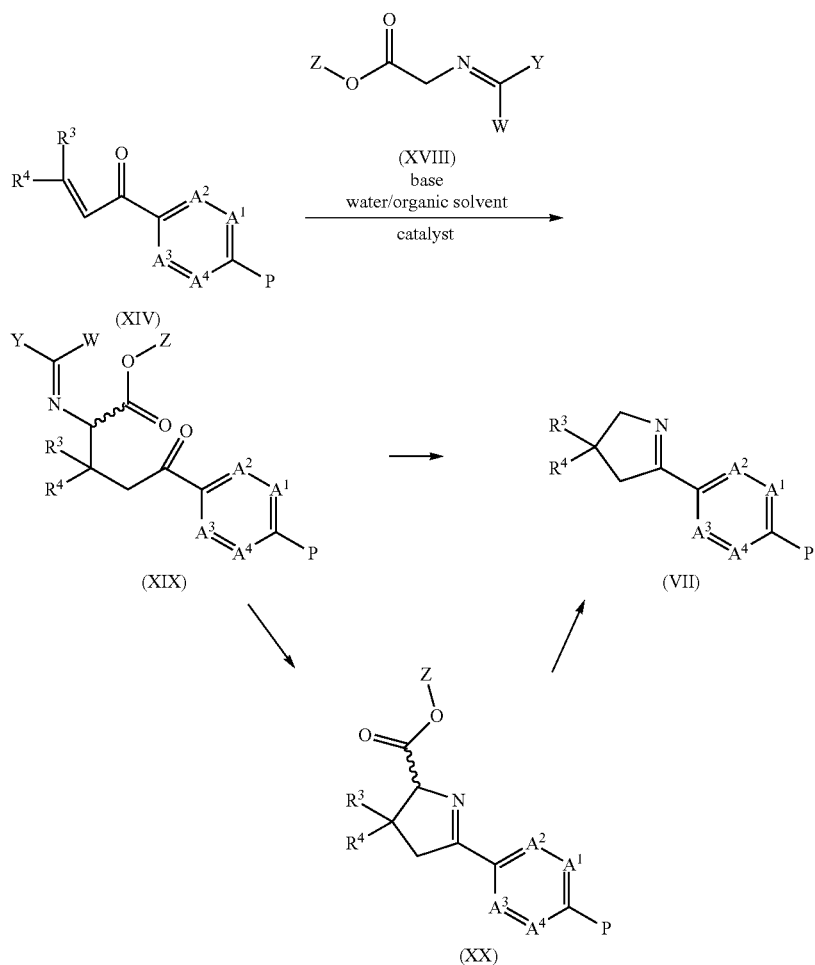

Scheme 6

11) Compounds of formula (XIX) wherein $R^3$ and $R^4$ are as defined for the compound of formula I, and wherein W is hydrogen or optionally substituted aryl, Y is optionally substituted aryl, and Z is optionally substituted alkyl or optionally substituted arylalkylene, can be prepared by reacting a compound of formula (XIV) with a glycine Schiff base of formula (XVIII), in the presence of base. In most cases it is advantageous to conduct the reaction using a solvent at a dilution of 0.1 M to 1 M, preferably 0.3 M to 0.5 M. Suitable organic solvents could be used, for example toluene, 1,2-dichloroethane, dichloromethane, tetrahydrofuran, methanol or ethyl acetate. The reaction temperature is usually between 0° C. to 100° C., preferably between 40 and 100° C. When a solvent is used the reactants are usually at a dilution of e.g. between 0.1 M to 1 M. The reaction time is usually between 0 and 96 hours, preferably between 0 and 12 hours. Suitable bases include amines, such as triethylamine, 2,5-dimethylpiperazine, tetramethylpiperidine, 4-dimethylamino pyridine, potassium carbonate, metal alkoxides, such as sodium t-butoxide or metal fluorides, such as cesium fluoride.

12) Compounds of formula (XX) can be prepared by deprotecting and cyclizing compounds of formula (XIX). Suitable conditions for this transformation include acidic conditions, for instance the presence of strong acids such as trifluoroacetic acid, sulfonic acid or hydrochloric acid. Suitable solvents can be used, for example acetone, dimethylsulfoxide, dimethylformamide, toluene, xylenes, 1,2-dichloroethane, dichloromethane, tetrahydrofuran, methanol ethanol, tert-butanol, water or ethyl acetate at a temperature from 0° C. to 140° C., preferably between 0° C. and 80° C., and at dilution of e.g. between 0.1 M to 1 M. The reaction time is usually between 1 and 24 hours, preferably between 1 and 6 hours.

13) Alternatively, compounds of formula (VII) can be prepared by decarboxylating compounds of formula (XX). Suitable conditions for this transformation involve heating the compounds in a suitable media, which depending on the group Z may include some standard additives known by a person skilled in the art. Suitable solvents can be used, for example acetone, dimethylsulfoxide, dimethylformamide, toluene, xylenes, 1,2-dichloroethane, dichloromethane, tetrahydrofuran, methanol, ethanol, tert-butanol, water or ethyl acetate. The temperature is usually between 0° C. and 200° C., preferably between 50 and 180° C. Where a solvent is used, the reactants are usually at dilution of e.g. between 0.1 M to 1 M. The reaction time is usually between 0 and 96 hours, preferably between 0 and 24 hours. The reaction can also be performed under microwave conditions, preferably between 40 and 180° C., In some cases, however, it is necessary or useful to add an additive, such as a metal halide, for instance sodium chloride or potassium iodide, or a metal cyanide, such as sodium cyanide to the reaction media, or a base (e.g. when group Z is alkyl). In the case where Z is aryl-methylene (e.g. benzyl), suitable deprotection conditions include hydrogenation conditions. The most useful solvents are alcohols such as methanol or ethanol and in most cases it is advantageous to conduct the reaction at dilution between 0.1 M to 1 M, preferably 0.3 M to 0.5 M. The amount of catalyst, such as palladium on charcoal added is usually between 0.1 molar equivalent and 0.50 molar equivalents and the reaction time in most cases is between 1 hour and 6 hours.

14) Compounds of formula (VII) can be prepared by deprotecting, decarboxylating and cyclizing compounds of formula (XIX) according to a one-pot stepwise procedure without isolating the intermediates. Suitable conditions for this transformation include acidic conditions, for instance the presence of strong acids such as trifluoroacetic acid or hydrochloric acid, or basic conditions, depending on the group Z. Suitable solvents could be used, for example acetone, dimethylsulfoxide, dimethylformamide, toluene, xylenes, 1,2-dichloroethane, dichloromethane, tetrahydrofuran, methanol, ethanol, tert-butanol, water or ethyl acetate. The temperature is usually between 0° C. and 200° C., preferably between 50 and 180° C. Where a solvent is used the reactants are usually at dilution of e.g. between 0.1 M to 1 M. The reaction time is usually between 1 and 96 hours, preferably between 1 and 12 hours. The reaction can also be performed under microwave conditions, preferably between 40 and 180° C. In some cases, however, it is necessary or useful to add an additive, such as a metal halide, for instance sodium chloride or potassium iodide, or a metal cyanide, such as sodium cyanide to the reaction media.

Enantiomerically enriched mixtures of compounds of formula (VII) may be prepared, for example, according to schemes 4, 5 or 6 by formation of intermediate XV, XVII or XIX via an asymmetric Michael addition, see for example J. Org. Chem. 2008, 73, 3475-3480 and references cited therein" and J. Am. Chem. Soc. 2008, 130, 6072-6073. See also PCT/EP2011/059823.

Scheme 7

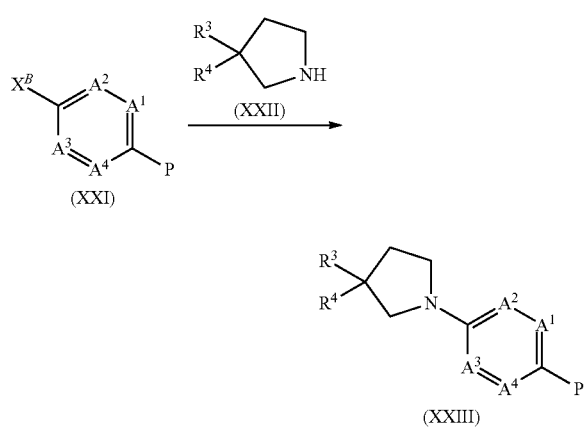

15) Alternatively, compounds of formula (XXIII) can be prepared by reaction of compound of formula (XXI) with an amine compound of formula (XXII) as shown in Scheme 7 in the absence or the presence of a catalyst, such as palladium(II) acetate or bis(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

Compounds of formula (XXII) can be prepared according to a method developed in the literature: Tetrahedron (1996), 52, (1), 59-70 and Tetrahedron Letters (1993), 34, (20), 3279-82.

16) Compounds of formula (XXI) wherein $X^B$ is a leaving group, for example a halogen, such as bromo, can be prepared as described in WO09080250.

Scheme 8

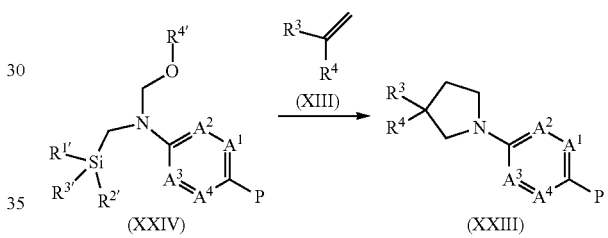

17) Compounds of formula (XXIII) can be prepared by reaction of compound of formula (XXV) wherein $R^{1'}$, $R^{2'}$ and $R^{3'}$ are independently of each other optionally substituted alkyl or optionally substituted phenyl groups, with styrene of formula (XIII) according to a method developed in the literature: Journal of Medicinal Chemistry (1990), 33(2), 849-54.

18) Compounds of formula (XXIII) can be prepared by reaction of compound of formula (XXIV) wherein $R^{4'}$ is optionally substituted alkyl group, $R^{1'}$, $R^{2'}$ and $R^{3'}$ are independently of each other optionally substituted alkyl or optionally substituted phenyl groups, with styrene of formula (XIII) according to a method developed in the literature: Tetrahedron (1996), 52, (1), 59-70 and Tetrahedron Letters (1993), 34, (20), 3279-82.

Scheme 9

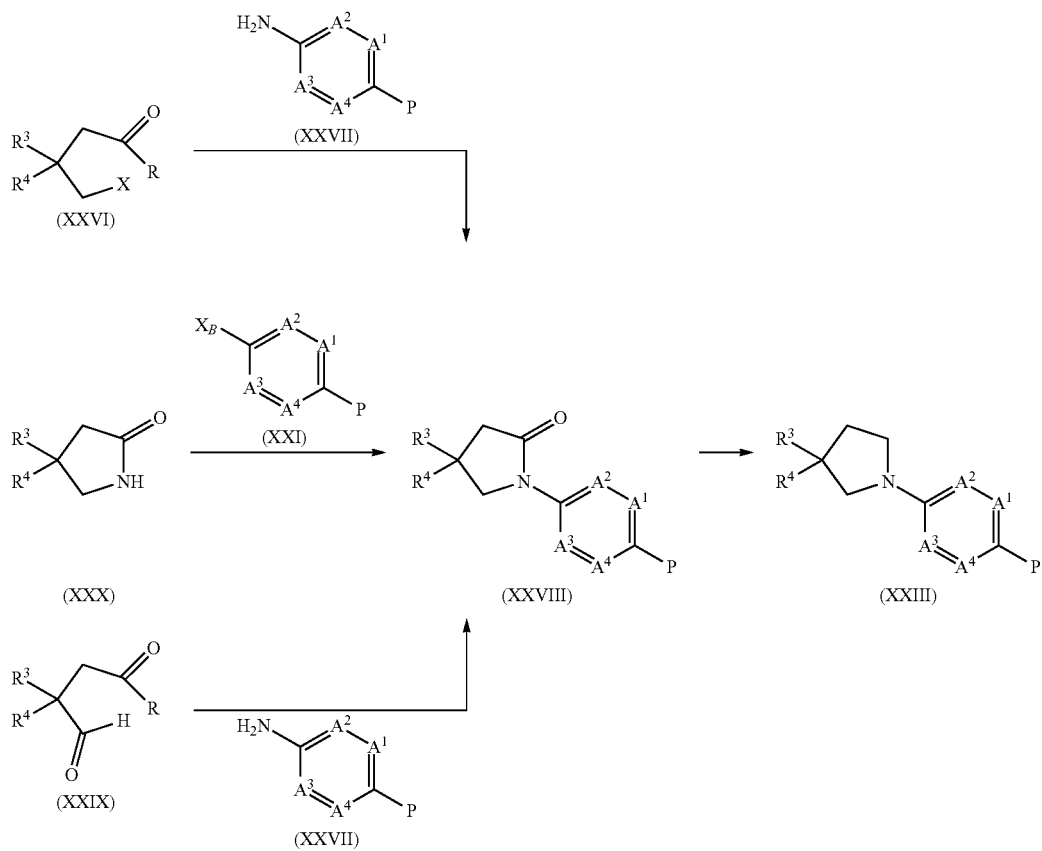

19) Compounds of formula (XXIII) can be prepared by reduction of compounds of formula (XXVIII) with a metal hydride, for instance according to a method developed in the literature: Journal of Pharmaceutical Sciences (1978), 67(7), 953-6.

20) Compounds of formula (XXVIII) can be prepared by reaction of compound of formula (XXX) with a compound of formula (XXI) as described in 15).

Compounds of formula (XXX) can be prepared by many methods as described in the literature (Bioorganic & Medicinal Chemistry Letters (2010), 20(1), 362-365).

21) Compounds of formula (XXVIII) can be prepared by reaction of compound of formula (XXVI) wherein R is OH, $C_1$-$C_6$alkoxy or Cl, F or Br, with a compound of formula (XXVII) under standard reductive amination conditions.

22) Compounds of formula (XXVI) can be prepared by many methods as described in the literature (US patent US 2005148792).

23) Compounds of formula (XXVIII) can be prepared by reaction of compound of formula (XXVI) wherein R is OH, $C_1$-$C_6$alkoxy or Cl, F or Br, and X is a leaving group, such as a mesylate, a tosylate or an halogen with a compound of formula (XXVII) under standard substitution reaction conditions.

Scheme 10

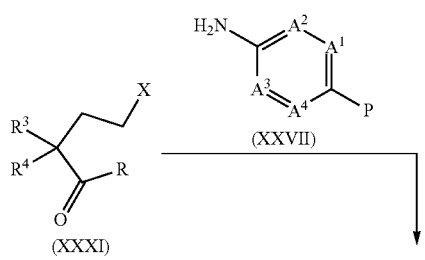

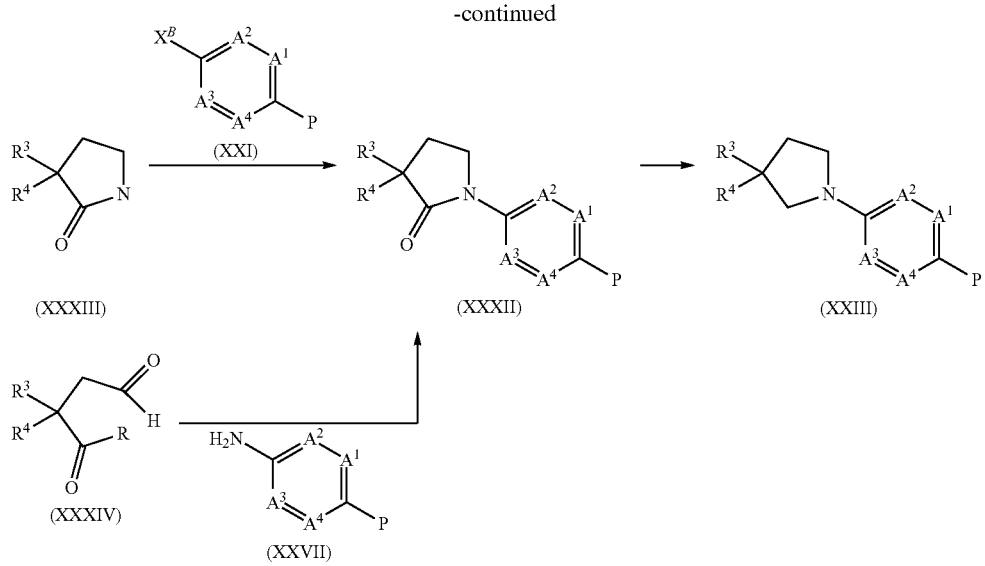

24) Compounds of formula (XXIII) can be prepared by reduction of compounds of formula (XXXII) with a metal hydride, for instance according to a method developed in the literature: Tetrahedron: Asymmetry (1999), 10(20), 3877-3881

25) Compounds of formula (XXXII) can be prepared by reaction of compound of formula (XXXIII) with a compound of formula (XXI) as described in 15).

formula (XXVII) under standard reductive amination conditions.

28) Compounds of formula (XXXIV) can be prepared by many methods as described in the literature.

29) Compounds of formula (XXXIII) can be prepared by reaction of compound of formula (XXXI) wherein R is OH, $C_1$-$C_6$alkoxy or Cl, F or Br, and X is a leaving group, such as a mesylate, a tosylate or an halogen with a compound of formula (XXXVII) under standard substitution reaction conditions.

Scheme 11

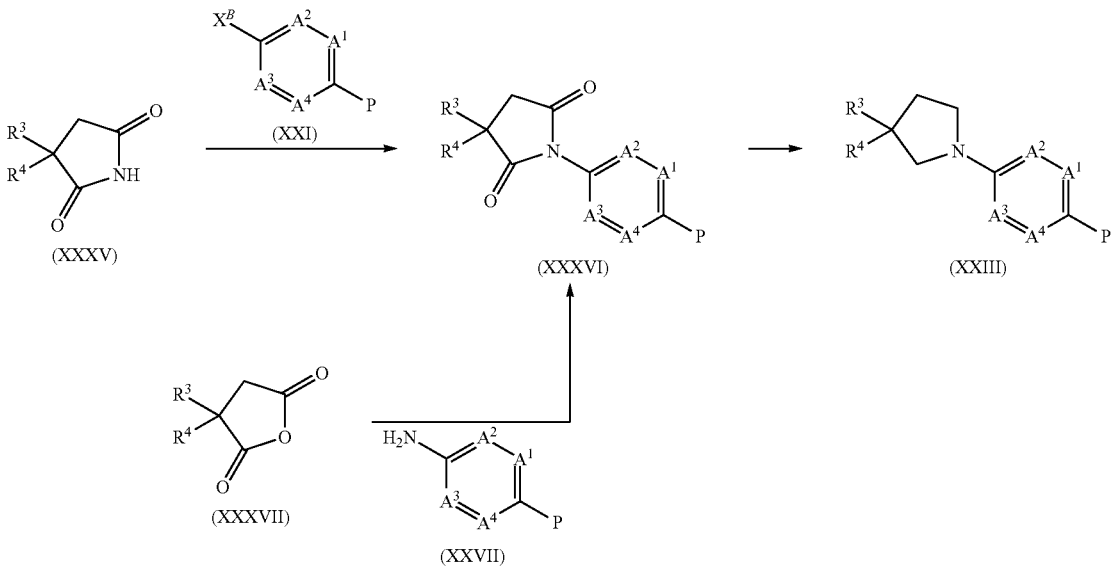

26) Compounds of formula (XXXIII) can be prepared by many methods as described in the literature (Tetrahedron: Asymmetry (1999), 10(20), 3877-3881).

27) Compounds of formula (XXXII) can be prepared by reaction of compound of formula (XXXIV) wherein R is OH, $C_1$-$C_6$alkoxy or Cl, F or Br, with a compound of 30) Compounds of formula (XXIII) can be prepared by reduction of compounds of formula (XXXVI) with a metal hydride, for instance according to a method developed in the literature (ARKIVOC, 2003, 5, And U.S. Pat. No. 4,524, 206).

31) Compounds of formula (XXXVI) can be prepared by reaction of compound of formula (XXXV) with a compound of formula (XXI) as described in 15).

32) Compounds of formula (XXXVI) can be prepared by reaction of compound of formula (XXXVII) with a compound of formula (XXVII) under standard substitution reaction conditions.

Scheme 12

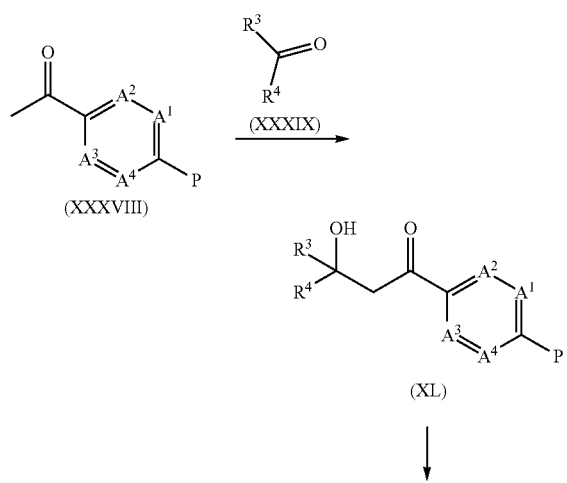

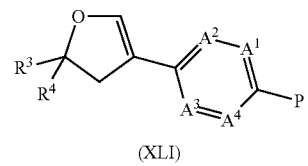

(XLI)

33) Compounds of formula (XLI) can be prepared by reacting a compound of formula (XL) with trimethylsilyl-diazomethane, in the presence of an organometallic reagent, such as methyl lithium, in a suitable solvent, such as tetrahydrofuran, diethyl ether, N,N-dimethylformamide or dimethoxyethane. The reaction is carried out at a temperature of from −78° C. to 100° C., preferably from −78° C. to ambient temperature. Compounds of formula (XL) are either known compounds or can be prepared using methods described for example in WO2007/074789, preferably by reacting a compound of formula (XXXVIII) with a ketone of formula (XXXIX).

Scheme 13

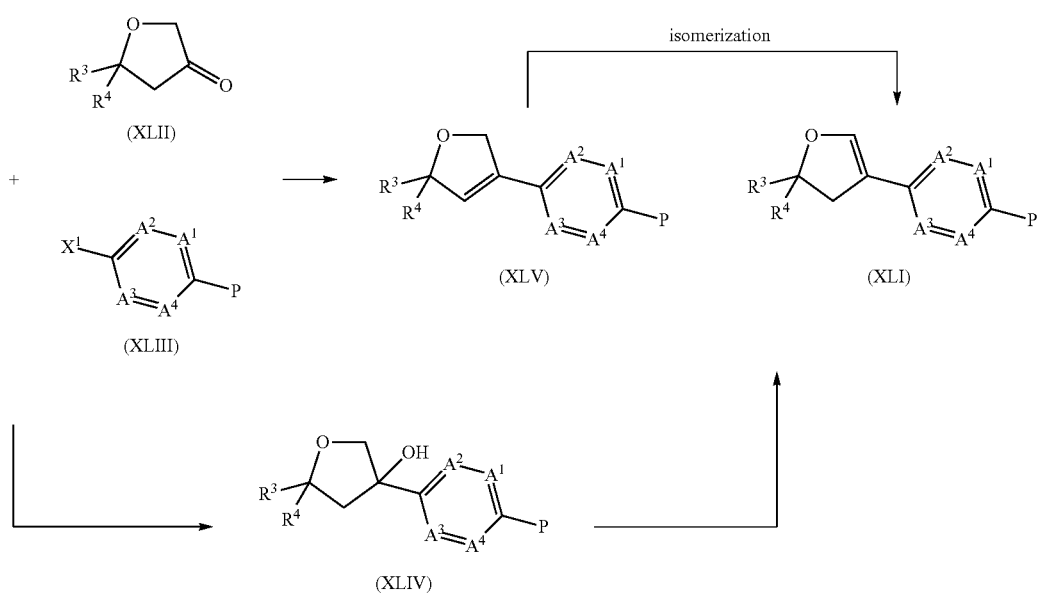

34) Alternatively, 2,3-dihydrofuran compounds of formula (XLI) may be prepared by isomerisation of 2,5-dihydrofuran of formula (XLV) using a metal catalyst such as RhCl(PPh$_3$)$_3$, RhH(PPh$_3$)$_4$, H$_2$Ru(CO)(PPh$_3$)$_3$, RuCl$_3$, HClRu(CO)(PPh$_3$)$_3$ or H$_2$Ru(PPh$_3$)$_4$ in a solvent such as toluene or an alcoholic solvent such as ethanol at a temperature of between room temperature and 150° C., preferably between 80° C. and 120° C. Such conditions of isomerisation of 2,5-dihydrofuran compounds have been described in *Chem. Eur. J.* 2003, 9, 4442-4451 using the general catalytic isomerisation described by M. Mori et al in *J. Org. Chem.* 2000, 65, 3966-3970 or M. Bartok et al in *J. Organomet. Chem.* 1985, 297, C37-C40. Alternatively, the isomerisation may be performed in the presence of basic oxide metal catalysts such as MgO, CaO, SrO, or La$_2$O$_3$ as described by K. Tanabe in *Chem. Lett.* 1981, 341-342 for the isomerisation of 2,5-dihydrofuran.

35) Compounds of formula (XLV) and (XLI) can be prepared by reacting a compound of formula (XLIII) wherein X$^1$ is a leaving group, for example a halogen, such as iodo or bromo with a compound of formula (XLII), in the presence of a metal, such as catalyst, such as magnesium, lithium, indium, cerium or zinc, in a suitable solvent, such as tetrahydrofuran, diethyl ether or N,N-dimethylformamide. The reaction is carried out at a temperature of from −78° C. to 100° C., preferably from −78° C. to ambient temperature.

36) Compounds of formula (XLIV) can be prepared by reacting a compound of formula (XLIII) with a compound of formula (XLII), in the presence of a metal, such as magnesium, indium, cerium, zinc, or an organolithium reagent, such as n-butyl lithium, in a suitable solvent, such as tetrahydrofuran, diethyl ether or N,N-dimethylformamide. The reaction is carried out at a temperature of from −100° C. to 100° C., preferably from −100° C. to ambient temperature.

37) Compounds of formula (XLV) and (XLI) can be prepared by reacting a compound of formula (XLIV) in the presence of an acid, such as p-toluenesulfonic acid or sulphuric acid, or in the presence of a dehydrating agent, such as POCl$_3$ in a suitable solvent, such as tetrahydrofuran, diethyl ether or dichloromethane. The reaction is carried out at a temperature of from −78° C. to 100° C., preferably from −40° C. to ambient temperature.

38) Alternatively, compounds of formula (XLV) and (XLI) can be obtained by reacting a compound of formula (XLIV) in the presence of a chlorinating agent, such as thionyl chloride or oxalyl chloride, or an acetylating agent, such as acetic anhydride in the presence of a base, such as triethylamine, potassium carbonate or pyridine, in a suitable solvent, such as tetrahydrofuran, diethyl ether or dichloromethane. The reaction is carried out at a temperature of from −78° C. to 100° C., preferably from −40° C. to ambient temperature.

39) Compounds of formula (XLIII) are either known compounds or can be prepared by known methods to the person skilled in the art. Compounds of formula (XLII) can be prepared as described in

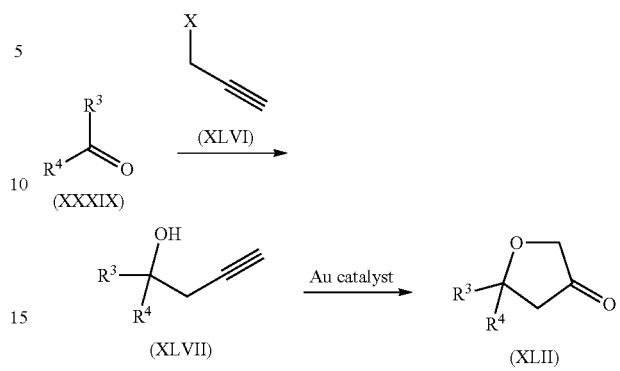

Scheme 14

40) Compounds of formula (XLII) can be prepared by hydrative cyclisation of a compound of formula (XLVII) These reactions are usually carried out in the presence of a suitable lewis acid, such as a gold catalyst, as described in *J. Am. Chem. Soc.*, 2010, 132 (10), pp 3258-3259. The reaction is usually carried out using (Triphenylphosphine)gold(I) bis(trifluoromethanesulfonyl)imidate, in the presence of a pyridine N-oxyde, such as 5-Bromo-1-oxy-nicotinic acid methyl ester and an acid, such as methanesulfonic acid, in an aprotic solvent, such as 1,2-dichloroethane. The reaction is carried out at a temperature of from 0° C. to 100° C., preferably from 0° C. to 40° C.

41) Compounds of formula (XLVII) can be prepared by reacting a ketone of formula (XXXIX) with a compound of formula (XLVI), where X is a halogen. These reactions are usually carried out in the presence of a metal, such as magnesium, lithium, indium, cerium or zinc, in a suitable solvent, such as tetrahydrofuran, diethyl ether or N,N-dimethylformamide. The reaction is carried out at a temperature of from −78° C. to 100° C., preferably from −78° C. to ambient temperature. Alternatively, compounds of formula (XLVII) can be prepared by reacting a compound of formula (XXXIX) with a compound of formula (XLVI), where X is a trialkylsilyl group. These reactions are usually carried out in the presence of strong base, such as lithium diisopropylamide, in a suitable solvent, such as tetrahydrofuran, diethyl ether or N,N-dimethylformamide. The reaction is carried out at a temperature of from −78° C. to 100° C., preferably from −78° C. to ambient temperature.

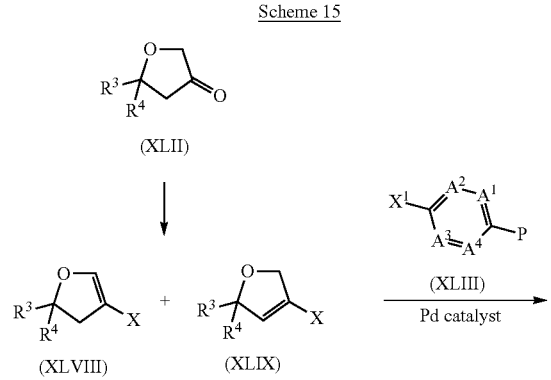

Scheme 15

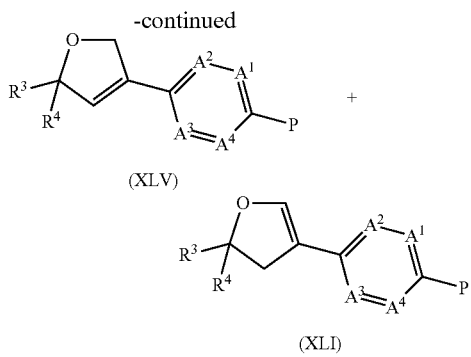

42) Compounds of formula (XLV) (and compounds of formula (XLI)) can be prepared by reacting a compound of formula (XLVIII) (and respectively compounds of formula (XLIX)) wherein X is a leaving group, for example a halogen, such as bromo, or a triflate, with a compound of formula (XLIII) wherein $X^1$ is a boron derivative, such as a boronic acid, a pinacolboronate, or a trifluoroborate salt, in a Suzuki coupling reaction, in the presence of a palladium catalyst, such as palladium acetate or tetrakis(triphenylphosphine) palladium, in a suitable solvent, such as 1,4-dioxane, touene, acetonitrile or N,N-dimethylformamide. The reaction is carried out at a temperature of from −20° C. to 150° C., preferably from ambient temperature to 100° C. Alternatively, compounds of formula (XLV) (and compounds of formula (XLI)) can be prepared by reacting a compound of formula (XLVIII) (and respectively compounds of formula (XLIX)) wherein X is a leaving group, for example a halogen, such as bromo, or a triflate with a compound of formula (XLIII) wherein $X^1$ is a trialkylstannane derivative, such as tributyltin, or respectively an organozinc derivative in a Stille or Negishi coupling reaction, in the presence of a palladium catalyst, such as palladium acetate or tetrakis (triphenylphosphine) palladium, in a suitable solvent, such as 1,4-dioxane, touene, acetonitrile or N,N-dimethylformamide.

43) Compounds of formula (XLVIII) (and compounds of formula (XLIX)) wherein X is a halogen, such as bromo, can be prepared by reacting a compound of formula (XLII) with a brominating agent, such as phosphoric tribromide, in a suitable solvent, such as tetrahydrofuran, or chloroform, dichloromethane. The reaction is carried out at a temperature of from −40° C. to 100° C., preferably from −40° C. to ambient temperature. Alternatively, compounds of formula (XLVIII) (and compounds of formula (XLIX)) wherein X is a triflate, can be prepared by reacting a compound of formula (XLII) with a triflating agent, such as triflic anhydride or N,N-bis(trifluoromethanesulfonyl)aniline, in the presence of a base, such as 4-picoline, sodium or potassium hexamethyldisilylamide, lithium diisopropylamide, triethylamine or 2,6-lutidine in a suitable solvent, such as tetrahydrofuran, chloroform or dichloromethane. The reaction is carried out at a temperature of from −100° C. to 150° C., preferably from −40° C. to 100° C.

The compounds according to the present invention show a potential insecticidal action and can therefore be used as an insecticide. Furthermore, the compounds according to the present invention can exhibit a strong control effect against harmful insects, without substantially imposing any harmful side effects to cultivated plants. The compounds of the present invention can thus be used for the control of a wide range of pest species, for example, harmful sucking insects, chewing insects, as well as other plant parasitic pests, storage insects, hygiene pests and the like, and can be applied for the purpose of disinfestations and extermination thereof.

Harmful Animal Pest are for Example:

As for insects, coleopterans, for example, *Callosobruchus chinensis, Sitophilus zeamais, Tribolium castaneum, Epilachna vigintioctomaculata, Agriotesfuscicollis, Anomala rufocuprea, Leptinotarsa decemlineata, Diabrotica* spp., *Monochamus alternatus, Lissorhoptrus oryzophilus, Lyctus bruneus, Aulacophora femoralis*; lepidopterans, for example, *Lymantria dispar, Malacosoma neustria*), *Pieris rapae, Spodoptera litura, Mamestra brassicae, Chilo suppressalis*), *Pyrausta nubilalis, Ephestia cautella, Adoxophyes orana, Carpocapsa pomonella, Agrotisfucosa, Galleria mellonella, Plutella maculipennis, Heliothis virescens, Phyllocnistis citrella*; hemipterans, for example, *Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nezara* spp., *Trialeurodes vaporariorm, Psylla* spp.; thysanopterans, for example, *Thrips palmi, Franklinella occidental*; orthopterans, for example, *Blatella germanica, Periplaneta americana, Gryllotalpa Africana, Locusta migratoria migratoriodes*; isopterans, for example, *Reticulitermes speratus, Coptotermes formosanus*; dipterans, for example, *Musca domestica, Aedes aegypti, Hylemia platura, Culex pipiens, Anopheles sinensis, Culex tritaeniorhynchus, Liriomyza trifolii*.

As for acari, for example, *Tetranychus cinnabarinus, Tetranychus urticae, Panonychus citri, Aculops pelekassi, Tarsonemus* spp.

As for nematodes, for example, *Meloidogyne incognita, Bursaphelenchus lignicolus Mamiya et Kiyohara, Aphelenchoides besseyi, Heterodera glycines, Pratylenchus* spp.

Additionally, the compounds according to the present invention may show a good plant tolerance and favourable toxicity to warm-blooded animals and being tolerated well by the environment, and thus are suitable for protecting plants and plant parts. Application of the compounds of the invention may result in increasing the harvest yields, improving the quality of the harvested material.

Additionally, the compounds can be used for controlling animal pests, in particular insects, arachnids, helminths, nematodes and molluscs, which are encountered in agriculture, in horticulture, the field of veterinary medicine, in forests, in gardens and leisure facilities, in the protection of stored products and of materials, and in the hygiene sector. They may preferably be employed as plant protection agents. They may be active against normally sensitive and resistant species and against all or some stages of development.

These Pests Include Inter Alia:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimeruspyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscehdes obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apogonia* spp., *Atomaria* spp., *Attagenus* spp., *Bruchidius obtectus*, *Bruchus* spp., *Ceuthorhynchus* spp., *Cleonus mendicus*, *Conoderus* spp., *Cosmopolites* spp., *Costelytra zealandica*, *Curculio* spp., *Cryptorhynchus lapathi*, *Dermestes* spp., *Diabrotica* spp., *Epilachna* spp., *Faustinus cubae*, *Gibbium psylloides*, *Heteronychus arator*, *Hylamorpha elegans*, *Hylotrupes bajulus*, *Hypera postica*, *Hypothenemus* spp., *Lachnosterna consanguinea*, *Leptinotarsa decemlineata*, *Lissorhoptrus oryzophilus*, *Lixus* spp., *Lyctus* spp., *Meligethes aeneus*, *Melolontha melolontha*, *Migdolus* spp., *Monochamus* spp., *Naupactus xanthographus*, *Niptus hololeucus*, *Oryctes rhinoceros*, *Oryzaephilus surinamensis*, *Otiorrhynchus sulcatus*, *Oxycetonia jucunda*, *Phaedon cochleariae*, *Phyllophaga* spp., *Popilliajaponica*, *Premnotrypes* spp., *Psylliodes chrysocephala*, *Ptinus* spp., *Rhizobius ventralis*, *Rhizopertha dominica*, *Sitophilus* spp., *Sphenophorus* spp., *Sternechus* spp., *Symphyletes* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinellafrit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloidesfuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It may be furthermore possible to control protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelopsfurcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Mono-morium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupaluspiniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*,

*Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

All plants and plant parts can be treated in accordance with the invention.

Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights.

Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes.

The plant parts also include harvested material, and vegetative and generative propagation material, for example cuttings, tubers, rhizomes, offshoots and seeds. Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

In a preferred embodiment, wild plant species and plant cultivars, or those obtained by conventional biological breeding methods, such as crossing or protoplast fusion, and parts thereof, are treated.

Compounds of formula I may be used on transgenic plants (including cultivars) obtained by genetic engineering methods and/or by conventional methods. These are understood as meaning plants having novel properties ("traits") which have been obtained by conventional breeding, by mutagenesis or by recombinant DNA techniques. Depending on the plant species or plant cultivars, their location and growth conditions (soils, climate, vegetation period, diet), the treatment according to the invention may also result in superadditive ("synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soybean, potatoes, sugar beet, tomatoes, peas and other vegetable varieties, cotton, tobacco, oilseed rape and also fruit plants (with the fruits apples, pears, citrus fruits and grapes).

Compounds of formula I may be used on transgenic plants that are capable of producing one or more pesticidal proteins which confer upon the transgenic plant tolerance or resistance to harmful pests, e.g. insect pests, nematode pests and the like. Such pesticidal proteins include, without limitation, Cry proteins from *Bacillus thuringiensis* Cry1Ab, Cry1Ac, Cry1F, Cry2Ab, Cry2Ae, Cry3A, Cry3Bb, or Cry9C; engineered proteins such as modified Cry3A (U.S. Pat. No. 7,030,295) or Cry1A.105; or vegetative insecticidal proteins such as Vip1, Vip2 or Vip3. A full list of Bt Cry proteins and VIPs useful in the invention can be found on the worldwide web at *Bacillus thuringiensis* Toxin Nomenclature Database maintained by the University of Sussex (see also, Crickmore et al. (1998) *Microbiol. Mol. Biol. Rev.* 62:807-813). Other pesticidal proteins useful in the invention include proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. Further examples of such pesticidal proteins or transgenic plants capable of synthesizing such proteins are disclosed, e.g., in EP-A 374753, WO 93/007278, WO 95/34656, EP-A 427529, EP-A 451878, WO 03/18810 and WO 03/52073. The methods for producing such transgenic plants are generally known to the person skilled in the art and some of which are commercially available such as Agrisure®CB (P1) (corn producing Cry1Ab), Agrisure®RW (P2) (corn producing mCry3A), Agrisure® Viptera (P3) (corn hybrids producing Vip3Aa); Agrisure300GT (P4) (corn hybrids producing Cry1Ab and mCry3A); YieldGard® (P5) (corn hybrids producing the Cry1Ab protein), YieldGard® Plus (P6) (corn hybrids producing Cry1Ab and Cry3Bb1), Genuity® SmartStax® (P7) (corn hybrids with Cry1A.105, Cry2Ab2, Cry1F, Cry34/35, Cry3Bb); Herculex® I (P8) (corn hybrids producing Cry1Fa) and Herculex®RW (P9) (corn hybrids producing Cry34Ab1, Cry35Ab1 and the enzyme Phosphinothricin-N-Acetyltransferase [PAT]); NuCOTN®33B (P10) (cotton cultivars producing Cry1Ac), Bollgard® I (P11) (cotton cultivars producing Cry1Ac), Bollgard®II (P12) (cotton cultivars producing Cry1Ac and Cry2Ab2) and VIPCOT® (P13) (cotton cultivars producing a Vip3Aa). Soybean Cyst Nematode resistance soybean (SCN®—Syngenta (P14)) and soybean with Aphid resistant trait (AMT® (P15)) are also of interest.

Further Examples of Such Transgenic Crops are:

1. Bt11 Maize from Syngenta Seeds SAS, Chemin de l'Hobit 27, F-31 790 St. Sauveur, France, registration number C/FR/96/05/10 (P16). Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10 (P17). Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10 (P18). Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9 (P19). MON 863 expresses a CryIIIB (b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02. (P20)

6. 1507 Maize from Pioneer Overseas Corporation, Avenue Tedesco, 7 B-1160 Brussels, Belgium, registration number C/NL/00/10. (P21) Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03 (P22). Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Further examples of transgenic plants, and of very high interest, are those carrying traits conferring resistance to 2.4 D (e.g. Enlist®) (e.g. WO 2011066384) (P23), glyphosate (e.g. Roundup Ready® (P24), Roundup Ready 2 Yield® (P25)), sulfonylurea (e.g. STS®) (P26), glufosinate (e.g. Liberty Link® (P27), Ignite® (P28)), Dicamba (P29) (Monsanto), HPPD tolerance (P30) (e.g. isoxaflutole herbicide) (Bayer CropScience, Syngenta). Double or triple stacks of any of the traits described here are also of interest, including glyphosate and sulfonyl-urea tolerance ((e.g. Optimum GAT®) (P31), plants stacked with STS® and Roundup Ready® (P32) or plants stacked with STS® and Roundup Ready 2 Yield® (P33)), dicamba and glyphosate tolerance (P34) (Monsanto). Of particular interest are soybean plants carrying trains conferring resistance to 2.4 D (e.g. Enlist®), glyphosate (e.g. Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta). Double or triple stack in soybean plants of any of the traits described here are also of interest, including glyphosate and sulfonyl-urea tolerance (e.g. Optimum GAT®, plants stacked with STS® and Roundup Ready® or Roundup Ready 2 Yield®), dicamba and glyphosate tolerance (Monsanto).

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

Furthermore, in the field of veterinary medicine, the novel compounds of the present invention can be effectively used against various harmful animal parasitic pests (endoparasites and ectoparasites), for example, insects and helminthes.

Examples of such animal parasitic pests include the pests as described below. Examples of the insects include *Gasterophilus* spp., *Stomoxys* spp., *Trichodectes* spp., *Rhodnius* spp., *Ctenocephalides canis, Cimx lecturius, Ctenocephalides felis, Lucilia cuprina*, and the like. Examples of acari include *Ornithodoros* spp., *Ixodes* spp., *Boophilus* spp., and the like.

In the veterinary fields, e.g. in the field of veterinary medicine, the active compounds according to the present invention are active against animal parasites, in particular ectoparasites or endoparasites.

The term endoparasites includes in particular helminths, such as cestodes, nematodes or trematodes, and protozoae, such as coccidia.

Ectoparasites are typically and preferably arthropods, in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like.

These Parasites Include:

From the order of the Anoplurida, for example *Haematopinus* spp., *Linognathus* spp., *Pediculus* spp., *Phtirus* spp., *Solenopotes* spp.; particular examples are: *Linognathus* setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus*;* from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis, Bovicola ovis, Bovicola limbata, Damalina bovis, Trichodectes canis, Felicola subrostratus, Bovicola caprae, Lepikentron ovis, Werneckiella equi*; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca*; from the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides felis, Pulex irritans, Tunga penetrans, Xenopsylla cheopis*; from the order of the Heteropterida, for example *Cimex* spp., *Triatoma* spp., *Rhodnius* spp., *Panstrongylus* spp.

From the order of the Blattarida, for example *Blatta orientalis, Periplaneta americana, Blattela germanica, Supella* spp. (e.g. *Suppella longipalpa*);

From the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus* (*Boophilus*) spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroajacobsoni*; from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae* (*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi*.

The active compounds according to the invention are also suitable for controlling arthropods, helminths and protozoae, which attack animals.

Animals include agricultural livestock such as, for example, cattle, sheep, goats, horses, pigs, donkeys, camels, buffaloes, rabbits, chickens, turkeys, ducks, geese, cultured fish, honeybees.

Moreover, animals include domestic animals—also referred to as companion animals—such as, for example, dogs, cats, cage birds, aquarium fish and what are known as experimental animals such as, for example, hamsters, guinea pigs, rats and mice.

By controlling these arthropods, helminths and/or protozoae, it is intended to reduce deaths and improve performance (in the case of meat, milk, wool, hides, eggs, honey and the like) and health of the host animal, so that more economical and simpler animal keeping is made possible by the use of the active compounds according to the invention.

For example, it may be desirable to prevent or interrupt the uptake of blood by the parasites from the hosts.

Also, controlling the parasites may help to prevent the transmittance of infectious agents.

The term "controlling" as used herein with regard to the veterinary field, means that the active compounds are effective in reducing the incidence of the respective parasite in an animal infected with such parasites to innocuous levels.

More specifically, "controlling", as used herein, means that the active compound is effective in killing the respective parasite, inhibiting its growth, or inhibiting its proliferation.

Generally, when used for the treatment of animals the active compounds according to the invention can be applied directly.

Preferably they are applied as pharmaceutical compositions which may contain pharmaceutically acceptable excipients and/or auxiliaries which are known in the art.

In the veterinary field and in animal keeping, the active compounds are applied (e.g. administered) in the known manner by enteral administration in the form of, for example, tablets, capsules, drinks, drenches, granules, pastes, boluses, the feed-through method, suppositories; by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

The active compounds may be formulated as shampoo or as suitable formulations usable in aerosols, unpressurized sprays, for example pump sprays and atomizer sprays.

When used for livestock, poultry, domestic animals and the like, the active compounds according to the invention can be applied as formulations (for example powders, wettable powders ["WP"], emulsions, emulsifiable concentrates ["EC"], flowables, homogeneous solutions, and suspension concentrates ["SC"]) which comprise the active compounds in an amount of from 1 to 80 percent by weight, either directly or after dilution (e.g. 100- to 10 000-fold dilution), or else as a chemical bath.

When used in the veterinary field the active compounds according to the invention may be used in combination with suitable synergists or other active compounds, such as for example, acaricides, insecticides, anthelmintics, anti-protozoal drugs.

In the present invention, a substance having an insecticidal action against pests including all of these is referred to as an insecticide.

An active compound of the present invention can be prepared in conventional formulation forms, when used as an insecticide.

Examples of the formulation forms include solutions, emulsions, wettable powders, water dispersible granules, suspensions, powders, foams, pastes, tablets, granules, aerosols, active compound-infiltrated natural and synthetic materials, microcapsules, seed coating agents, formulations used with a combustion apparatus (for example, fumigation and smoking cartridges, cans, coils or the like as the combustion apparatus), ULV (cold mist, warm mist), and the like.

These formulations can be produced by methods that are known per se.

For example, a formulation can be produced by mixing the active compound with a developer, that is, a liquid diluent or carrier; a liquefied gas diluent or carrier; a solid diluent or carrier, and optionally with a surfactant, that is, an emulsifier and/or dispersant and/or foaming agent.

In the case where water is used as the developer, for example, an organic solvent can also be used as an auxiliary solvent.

Examples of the liquid diluent or carrier include aromatic hydrocarbons (for example, xylene, toluene, alkylnaphthalene and the like), chlorinated aromatic or chlorinated aliphatic hydrocarbons (for example, chlorobenzenes, ethylene chlorides, methylene chlorides), aliphatic hydrocarbons (for example, cyclohexanes), paraffins (for example, mineral oil fractions), alcohols (for example, butanol, glycols and their ethers, esters and the like), ketones (for example, acetone, methyl ethyl ketone, methyl isobutyl ketone, cyclohexanone and the like), strongly polar solvents (for example, dimethylformamide, dimethylsulfoxide and the like), water and the like. The liquefied gas diluent or carrier may be those which are gaseous at normal temperature and normal pressure, for example, aerosol propellants such as butane, propane, nitrogen gas, carbon dioxide and halogenated hydrocarbons. Examples of the solid diluent include pulverized natural minerals (for example, kaolin, clay, talc, chalk, quartz, attapulgite, montmorillonite, diatomaceous earth, and the like), pulverized synthetic minerals (for example, highly dispersed silicic acid, alumina, silicates and the like), and the like. Examples of the solid carrier for granules include pulverized and screened rocks (for example, calcite, marble, pumice, sepiolite, dolomite and the like), synthetic granules of inorganic and organic powder, fine particles of organic materials (for example, sawdust, coconut shells, maize cobs, tobacco stalk and the like), and the like. Examples of the emulsifier and/or foaming agent include nonionic and anionic emulsifiers [for example, polyoxyethylene fatty acid esters, polyoxyethylene fatty acid alcohol ethers (for example, alkylaryl polyglycol ether), alkylsulfonates, alkylsulfates, arylsulfonates and the like], albumin hydro lyzate, and the like. Examples of the dispersant include lignin sulfite waste liquor and methylcellulose.

Fixing agents can also be used in the formulations (powders, granules, emulsions), and examples of the fixing agent include carboxymethylcellulose, natural and synthetic polymers (for example, gum arabic, polyvinyl alcohol, polyvinyl acetate, and the like) and the like. Colorants can also be used, and examples of the colorants include inorganic pigments (for example, iron oxide, titanium oxide, Prussian Blue and the like), organic dyes such as alizarin dyes, azo dyes or metal phthalocyanine dyes, and in addition, trace elements such as the salts of iron, manganese, boron, copper, cobalt, molybdenum and zinc. The formulations in general can contain the active ingredient in an amount ranging from 0.1 to 95 percent by weight, and preferably 0.5 to 90 percent> by weight. The compound according to the present invention can also exist as an admixture with other active compounds, for example, insecticides, poisonous baits, bactericides, miticides, nematicides, fungicides, growth regulators, herbicides and the like, in the form of their commercially useful formulation forms and in the application forms prepared from those formulations.

The content of the compound according to the present invention in a commercially useful application form can be varied within a wide range.

The concentration of the active compound according to the present invention in actual usage can be, for example, in the range of 0.0000001 to 100 percent by weight, and preferably 0.00001 to 1 percent by weight.

The compounds according to the present invention can be used through conventional methods that are appropriate for the usage form.

The active compound of the present invention have, when used against hygiene pests and pests associated with stored products, stability effective against alkali on lime materials, and also shows excellent residual effectiveness on wood and soil. The compounds of the invention may have favourable properties with respect to amount appled, residue formulation, selectivity, toxicity, production methodology, high activity, wide spectrum of control, safety, control of resistant organisms, e.g. pests that are resistant to organic phosphorus agents and/or carbamate agents.

Further embodiments of the invention are described below.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

The compounds of the invention may be used for example on turf, ornamentals, such as flowers, shrubs, broad-leaved trees or evergreens, for example conifers, as well as for tree injection, pest management and the like.

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta_migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus*, and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans*_(vinegar eelworm), *Trichostrongylus* spp. (gastro intestinal nematodes) and *Deroceras reticulatum* (slug).

The compounds of the invention may be used for pest control on various plants, including soybean (e.g. in some cases 10-70 g/ha), corn (e.g. in some cases 10-70 g/ha), sugarcane (e.g. in some cases 20-200 g/ha), alfalfa (e.g. in some cases 10-70 g/ha), brassicas (e.g. in some cases 10-50 g/ha), oilseed rape (e.g. canola) (e.g. in some cases 20-70 g/ha), potatoes (including sweet potatoes) (e.g. in some cases 10-70 g/ha), cotton (e.g. in some cases 10-70 g/ha), rice (e.g. in some cases 10-70 g/ha), coffee (e.g. in some cases 30-150 g/ha), citrus (e.g. in some cases 60-200 g/ha), almonds (e.g. in some cases 40-180 g/ha), fruiting vegetables (e.g. tomatoes, pepper, chili, eggplant, cucumber, squash, pulses etc.) (e.g. in some cases 10-80 g/ha), tea (e.g. in some cases 20-150 g/ha), bulb vegetables (e.g. onion, leek etc.) (e.g. in some cases 30-90 g/ha), grapes (e.g. in some cases 30-180 g/ha), pome fruit (e.g. apples, pears etc.) (e.g. in some cases 30-180 g/ha), and stone fruit (e.g. pears, plums etc.) (e.g. in some cases 30-180 g/ha).

The compounds of the invention may be used on soybean to control, for example, *Elasmopalpus lignosellus, Diloboderus abderus, Diabrotica speciosa, Sternechus subsignatus, Formicidae, Agrotis ypsilon, Julus* spp., *Anticarsia gemmatalis, Megascelis* ssp., *Procornitermes* ssp., *Gryllotalpidae, Nezara viridula, Piezodorus* spp., *Acrosternum* spp., *Neomegalotomus* spp., *Cerotoma trifurcata, Popillia japonica, Edessa* spp., *Liogenysfuscus, Euchistus heros*, stalk borer, *Scaptocoris castanea, phyllophaga* spp., *Pseudoplusia includens, Spodoptera* spp., *Bemisia tabaci, Agriotes* spp. The compounds of the invention are preferably used on soybean to control *Diloboderus abderus, Diabrotica speciosa, Nezara viridula, Piezodorus* spp., *Acrosternum* spp., *Cerotoma trifurcata, Popillia japonica, Euchistus heros, phyllophaga* spp., *Agriotes* spp.

The compounds of the invention may be used on corn to control, for example, *Euchistus heros, Dichelopsfurcatus, Diloboderus abderus, Elasmopalpus lignosellus, Spodoptera frugiperda, Nezara viridula, Cerotoma trifurcata, Popillia japonica, Agrotis ypsilon, Diabrotica speciosa, Heteroptera, Procornitermes* ssp., *Scaptocoris castanea, Formicidae, Julus* ssp., *Dalbulus maidis, Diabrotica virgifera, Mocis latipes, Bemisia tabaci, heliothis* spp., *Tetranychus* spp., *thrips* spp., *phyllophaga* spp., *scaptocoris* spp., *Liogenysfuscus, Spodoptera* spp., *Ostrinia* spp., *Sesamia* spp., *Agriotes* spp. The compounds of the invention are preferably used on corn to control *Euchistus heros, Dichelopsfurcatus, Diloboderus abderus, Nezara viridula, Cerotoma trifurcata, Popillia japonica, Diabrotica speciosa, Diabrotica virgifera, Tetranychus* spp., *thrips* spp., *phyllophaga* spp., *scaptocoris* spp., *Agriotes* spp.

The compounds of the invention may be used on sugar cane to control, for example, *Sphenophorus* spp., termites, *Mahanarva* spp. The compounds of the invention are preferably used on sugar cane to control termites, *Mahanarva* spp.

The compounds of the invention may be used on alfalfa to control, for example, *Hypera brunneipennis, Hypera postica, Colias eurytheme, Collops* spp., *Empoasca solana, Epitrix, Geocoris* spp., *Lygus hesperus, Lygus lineolaris, Spissistilus* spp., *Spodoptera* spp., *Trichoplusia ni*. The compounds of the invention are preferably used on alfalfa to control *Hypera brunneipennis, Hypera postica, Empoasca solana, Epitrix, Lygus hesperus, Lygus lineolaris, Trichoplusia ni.*

The compounds of the invention may be used on brassicas to control, for example, *Plutella xylostella, Pieris* spp., *Mamestra* spp., *Plusia* spp., *Trichoplusia ni, Phyllotreta* spp., *Spodoptera* spp., *Empoasca solana, thrips* spp.,

*Spodoptera* spp., *Delia* spp. The compounds of the invention are preferably used on brassicas to control *Plutella xylostella Pieris* spp., *Plusia* spp., *Trichoplusia ni, Phyllotreta* spp., *thrips* spp.

The compounds of the invention may be used on oil seed rape, e.g. canola, to control, for example, *Meligethes* spp., *Ceutorhynchus napi, Psylloides* spp.

The compounds of the invention may be used on potatoes, including sweet potatoes, to control, for example, *Empoasca* spp., *Leptinotarsa* spp., *Diabrotica speciosa, Phthorimaea* spp., *Paratrioza* spp., *Maladera matrida, Agriotes* spp. The compounds of the invention are preferably used on potatoes, including sweet potatoes, to control *Empoasca* spp., *Leptinotarsa* spp., *Diabrotica speciosa, Phthorimaea* spp., *Paratrioza* spp., *Agriotes* spp.

The compounds of the invention may be used on cotton to control, for example, *Anthonomus grandis, Pectinophora* spp., *heliothis* spp., *Spodoptera* spp., *Tetranychus* spp., *Empoasca* spp., *thrips* spp., *Bemisia tabaci, Lygus* spp., *phyllophaga* spp., *Scaptocoris* spp. *Austroasca viridigrisea, Creontiades* spp., *Oxycaraenus hyalinipennis, Dysdercus cingulatus*. The compounds of the invention are preferably used on cotton to control *Anthonomus grandis, Tetranychus* spp., *Empoasca* spp., *thrips* spp., *Lygus* spp., *phyllophaga* spp., *Scaptocoris* spp. *Austroasca viridigrisea, Creontiades* spp., *Oxycaraenus hyalinipennis, Dysdercus cingulatus*.

The compounds of the invention may be used on rice to control, for example, *Leptocorisa* spp., *Cnaphalocrosis* spp., *Chilo* spp., *Scirpophaga* spp., *Lissorhoptrus* spp., *Oebalus pugnax*. The compounds of the invention are preferably used on rice to control *Leptocorisa* spp., *Lissorhoptrus* spp., *Oebalus pugnax*.

The compounds of the invention may be used on coffee to control, for example, *Hypothenemus Hampei, Perileucoptera Coffeella, Tetranychus* spp., *Brevipalpus* spp. The compounds of the invention are preferably used on coffee to control *Hypothenemus Hampei, Brevipalpus* spp., *Perileucoptera Coffeella*.

The compounds of the invention may be used on citrus to control, for example, *Panonychus citri, Phyllocoptruta oleivora, Brevipalpus* spp., *Diaphorina citri, Scirtothrips* spp., *thrips* spp., *Unaspis* spp., *Ceratitis capitata, Phyllocnistis* spp. The compounds of the invention are preferably used on citrus to control *Panonychus citri, Phyllocoptruta oleivora, Brevipalpus* spp., *Diaphorina citri, Scirtothrips* spp., *thrips* spp., *Phyllocnistis* spp.

The compounds of the invention may be used on almonds to control, for example, *Amyelois transitella, Tetranychus* spp.

The compounds of the invention may be used on fruiting vegetable, including tomatoes, pepper, chili, eggplant, cucumber, squash, pulses etc, to control *thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Bemisia tabaci, Trialeurodes* spp., *Paratrioza* spp., *Frankliniella occidentalis, Frankliniella* spp., *Anthonomus* spp., *Phyllotreta* spp., *Amrasca* spp., *Epilachna* spp., *Halyonmorpha* spp., *Scirtothrips* spp., *Leucinodes* spp., *Neoleucinodes* spp. *Maruca* spp. The compounds of the invention are preferably used on fruiting vegetable, including tomatoes, pepper, chili, eggplant, cucumber, squash, pulses etc, to control, for example, *thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Paratrioza* spp., *Frankliniella occidentalis, Frankliniella* spp., *Amrasca* spp., *Scirtothrips* spp., *Leucinodes* spp., *Neoleucinodes* spp. *Maruca* spp.

The compounds of the invention may be used on tea to control, for example, *Pseudaulacaspis* spp., *Empoasca* spp., *Scirtothrips* spp., *Caloptilia theivora*. The compounds of the invention are prferably used on tea to control *Empoasca* spp., *Scirtothrips* spp.

The compounds of the invention may be used on bulb vegetables, including onion, leek etc to control, for example, *thrips* spp., *Spodoptera* spp., *heliothis* spp. The compounds of the invention are preferably used on bulb vegetables, including onion, leek etc to control *thrips* spp.

The compounds of the invention may be used on grapes to control, for example, *Empoasca* spp., *Lobesia* spp., *Frankliniella* spp., *thrips* spp., *Tetranychus* spp., *Rhipiphorothrips Cruentatus, Eotetranychus Willamettei, Erythroneura Elegantula, Scaphoides* spp. *Scelodonta strigicollis*. The compounds of the invention are preferably used on grapes to control *Frankliniella* spp., *thrips* spp., *Tetranychus* spp., *Rhipiphorothrips Cruentatus, Scaphoides* spp. *Scelodonta strigicollis*.

The compounds of the invention may be used on pome fruit, including apples, pairs etc, to control, for example, *Cacopsylla* spp., *Psylla* spp., *Panonychus ulmi, Cydia ponmonella*. The compounds of the invention are preferably used on pome fruit, including apples, pairs etc, to control *Cacopsylla* spp., *Psylla* spp., *Panonychus ulmi*.

The compounds of the invention may be used on stone fruit to control, for example, *Grapholita molesta, Scirtothrips* spp., *thrips* spp., *Frankliniella* spp., *Tetranychus* spp. The compounds of the invention are preferably used on stone fruit to control *Scirtothrips* spp., *thrips* spp., *Frankliniella* spp., *Tetranychus* spp.

In another embodiment the compounds of formula (I) may be used on rice to control *Baliothrips biformis* (Thrips), *Chilo* spp. (e.g. *Chilo polychrysus* (Dark headed striped borer), *Chilo suppressalis* (Rice stemborer), *Chilo indicus* (Paddy stem borer), *Chilo polychrysus* (Dark-headed rice borer), *Chilo suppressalis* (Stripe stem borer)), *Cnaphalocrocis medinalis* (Rice leaf folder), *Dicladispa armigera* (Hispa), *Hydrellia philipina* (Rice whorl-maggot), *Laodelphax* spp. (Smaller brown planthopper) (e.g. *Laodelphax striatellus*), *Lema oryzae* (Rice leafbeetle), *Leptocorsia acuta* (Rice bug), *Leptocorsia oratorius* (rice bug), *Lissorhoptrus oryzophilus* (rice water weevil), *Mythemina separata* (armyworm), *Nephottetix* spp. (Green leafhopper) (e.g. *Nephotettix cincticeps, Nephotettix malayanus, Nephotettix nigropictus, Nephotettix parvus, Nephottetix virescens*), *Nilaparvata lugens* (Brown Planthopper), *Nymphula depunctalis* (Rice caseworm), *Orseolia oryzae* (Rice Gall midge), *Oulema oryzae* (Rice leafbeetle), *Scirpophaga incertulas* (Yellow Stemborer), *Scirpophaga innotata* (White Stemborer), *Scotinophara coarctata* (Rice black bug), *Sogaella frucifera* (White-backed planthopper), *Steneotarsonemus spinki*.

The compounds of formula I of the invention may be used to control animal housing pests including: Ants, Bedbugs (adult), Bees, Beetles, Boxelder Bugs, Carpenter Bees, Carpet Beetles, Centipedes, Cigarette, Beetles, Clover Mites, Cockroaches, Confused Flour Beetle, Crickets, Earwigs, Firebrats, Fleas, Flies, Lesser Grain Borers, Millipedes, Mosquitoes, Red Flour Beetles, Rice Weevils, Sawtoothed Grain Beetles, Silverfish, Sowbugs, Spiders, Termites, Ticks, Wasps, Cockroaches, Crickets, Flies, Litter Beetles (such as Darkling, Hide, and Carrion), Mosquitoes, Pillbugs, Scorpions, Spiders, Spider Mites (Twospotted, Spruce), Ticks.

The compounds of formula I of the invention may be used to control ornamental pests including: Ants (Including Imported fire ants), Armyworms, Azalea caterpillars, Aphids, Bagworms, Black vine weevils (adult), Boxelder bugs, Budworms, California oakworms, Cankerworms, Cockroaches, Crickets, Cutworms, Eastern tent caterpillars, Elm leaf beetles, European sawflies, Fall webworms, Flea beetles, Forest tent caterpillars, Gypsy moth larvae, Japanese beetles (adults), June beetles (adults), Lace bugs, Leaf-feeding caterpillars, Leafhoppers, Leafminers (adults), Leaf rollers, Leaf skeletonizers, Midges, Mosquitoes, Oleander moth larvae, Pillbugs, Pine sawflies, Pine shoot beetles, Pinetip moths, Plant bugs, Root weevils, Sawflies, Scale insects (crawlers), Spiders, Spittlebugs, Striped beetles, Striped oakworms, Thrips, Tip moths, Tussock moth larvae, Wasps, Broadmites, Brown softscales, California redscales (crawlers), Clover mites, Mealybugs, Pineneedlescales (crawlers), Spider mites, Whiteflies.

The compounds of the invention may be used to control turf pests including: Ants (Including Imported fire ants, Armyworms, Centipedes, Crickets, Cutworms, Earwigs, Fleas (adult), Grasshoppers, Japanese beetles (adult), Millipedes, Mites, Mosquitoes (adult), Pillbugs, Sod webworms, Sow bugs, Ticks (including species which transmit Lyme disease), Bluegrass billbugs (adult), Black turfgrass ataenius (adult), Chiggers, Fleas (adult), Grubs (suppression), Hyperodes weevils (adult), Mole crickets (nymphs and young adults), Mole Crickets (mature adults), Chinch Bugs.

The compounds of the invention may be used for soil applications, including as a seed application, to target at least the following: sucking pests such as aphids, thrips, brown plant hopper (e.g. on rice), sting bugs, white flies (e.g. on cotton and vegetables), mites; on soil pests such as corn root worm, wireworms, white grubs, *zabrus*, termites (e.g. on sugar cane, soy, pasture), maggots, cabbage root fly, red legged earth mite; on lepidoptera, such as *spodoptera*, cutworms, *elasmoplpus, plutella* (e.g. *brassica*), stem borers, leaf miners, flea beetle, *Sternechus*; on nematicides, such as *Heterodera glycines* (e.g. on soybean), *Pratylenchus brachyurus* (e.g. on corn), *P. zeae* (e.g. on corn), *P. penetrans* (e.g. on corn), *Meloidogyne incognita* (e.g. on vegetables), *Heterodera schachtii* (e.g. on sugar beet), *Rotylenchus reniformis* (e.g. on cotton), *Heterodera avenae* (e.g. on cereals), *Pratylenchus neglectus* (e.g. on cereals), *thornei* (e.g. on cereals).

The compounds of the invention may be used for seed applications at least on the following: soil grubs for corn, soybeans, sugarcane: *Migdolus* spp; *Phyllophaga* spp.; *Diloboderus* spp; *Cyclocephala* spp; *Lyogenys fuscus*; sugarcane weevils: *Sphenophorus levis* & *Metamasius hemipterus*; termites for soybeans, sugarcane, pasture, others: *Heterotermes tenuis; Heterotermes longiceps; Cornitermes cumulans; Procornitermes triacifer; Neocapritermes opacus; Neocapritermes parvus*; corn root worms for corn and potatoes: *Diabrotica* spp., seed Maggot: *Delia platura*; soil stinkbugs: *Scaptocoris castanea*; wireworms: *Agriotes* spp; *Athous* spp Hipnodes bicolor; *Ctenicera destructor; Limonius canu; Limonius californicus*; rice water weevil: *Lissorhoptrus oryzophilus*; Red Legged earth mites: *Halotydeus destructor*.

The invention therefore provides a method of combating and/or controlling an animal pest, e.g. an invertebrate animal pest, which comprises applying to the pest, to a locus of the pest, or to a plant susceptible to attack by the pest a pesticidally effective amount of a compound of formula (I). In particular, the invention provides a method of combating and/or controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest. The compounds of formula (I) are preferably used against insects, acarines or nematodes.

The term "plant" as used herein includes seedlings, bushes and trees. Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is generally used at a rate of 0.0001 g to 10 g (for example 0.001 g or 0.05 g), preferably 0.005 g to 10 g, more preferably 0.005 g to 4 g, per kilogram of seed.

In another aspect the present invention provides a composition comprising a pesticidally effective amount of a compound of formula (I), in particular an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifiying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition.

Examples of suitable pesticides include the following (where "Tx" means a compound of formula (I), and in particular a compound selected from Tables 1 to Table 120, which may result in a synergistic combination with the given active ingredient):

a) Pyrethroids, wherein suitable combinations include permethrin, cypermethrin, fenvalerate+Tx, esfenvalerate+Tx, deltamethrin, cyhalothrin (in particular lambda-cyhalothrin+Tx and gamma cyhalothrin+Tx), bifenthrin+Tx, fenpropathrin+Tx, cyfluthrin+Tx (including beta cyfluthrin+TX), tefluthrin+Tx, fish safe pyrethroids+Tx (for example ethofenprox+Tx), natural pyrethrin+Tx, tetramethrin+Tx, S-bioallethrin+Tx, fenfluthrin+Tx, prallethrin+Tx or 5-benzyl-3-furylmethyl-(E)-(1R,3S)-2,2-dimethyl-3-(2-oxothiolan-3-ylidenemethyl)cyclopropane carboxylate+Tx;

b) Organophosphates, wherein suitable combinations include profenofos+Tx, sulprofos+Tx, acephate+Tx, methyl parathion+Tx, azinphos-methyl+Tx, demeton-s-methyl+Tx, heptenophos+Tx, thiometon+Tx, fenamiphos+Tx, monocrotophos+Tx, profenofos+Tx, triazophos+Tx, methamidophos+Tx, dimethoate+Tx, phosphamidon+Tx, malathion+Tx, chlorpyrifos+Tx, phosalone+Tx, terbufos+Tx, fensulfothion+Tx, fonofos+Tx, phorate+Tx, phoxim+Tx, pirimiphos-methyl+Tx, pirimiphos-ethyl+Tx, fenitrothion+Tx, fosthiazate+Tx or diazinon+Tx;

c) Carbamates (including aryl carbamates), wherein suitable combinations include pirimicarb+Tx, triazamate+Tx, cloethocarb+Tx, carbofuran+Tx, furathiocarb+Tx, ethiofencarb+Tx, aldicarb+Tx, thiofurox+Tx, carbosulfan+Tx, bendiocarb+Tx, fenobucarb+Tx, propoxur+Tx, methomyl+Tx, thiodicarb+TX, or oxamyl+Tx;

d) Benzoyl ureas, wherein suitable combinations include diflubenzuron+Tx, triflumuron+Tx, hexaflumuron+Tx, flufenoxuron+Tx, lufeneron+Tx or chlorfluazuron+Tx;

e) Organic tin compounds, wherein suitable combinations include cyhexatin+Tx, fenbutatin oxide+Tx or azocyclotin+Tx;

f) Pyrazoles, wherein suitable combinations include tebufenpyrad+Tx and fenpyroximate+Tx;

g) Macrolides, such as avermectins or milbemycins, wherein suitable combinations include for example abamectin+Tx, emamectin benzoate+Tx, ivermectin+Tx, milbemycin+Tx, spinosad+Tx, azadirachtin+Tx or spinetoram+Tx;

h) Hormones or pheromones;

i) Organochlorine compounds, wherein suitable combinations include endosulfan+Tx (in particular alpha-endosulfan+Tx), benzene hexachloride+Tx, DDT+Tx, chlordane+Tx or dieldrin+Tx;

j) Amidines, wherein suitable combinations include chlordimeform+Tx or amitraz+Tx;

k) Fumigant agents, wherein suitable combinations include chloropicrin+Tx, dichloropropane+Tx, methyl bromide+Tx or metam+Tx;

l) Neonicotinoid compounds, wherein suitable combinations include imidacloprid+Tx, thiacloprid+Tx, acetamiprid+Tx, nitenpyram+Tx, dinotefuran+Tx, thiamethoxam+Tx, clothianidin+Tx or nithiazine+Tx;

m) Diacylhydrazines, wherein suitable combinations include tebufenozide+Tx, chromafenozide+Tx or methoxyfenozide+Tx;

n) Diphenyl ethers, wherein suitable combinations include diofenolan+Tx or pyriproxifen+Tx;

o) Indoxacarb+Tx;

p) Chlorfenapyr+Tx;

q) Pymetrozine+Tx or flonicamid+Tx;

r) Spirotetramat+Tx, spirodiclofen+Tx or spiromesifen+Tx;

s) Diamides, wherein suitable combinations include flubendiamide+Tx, chlorantraniliprole (Rynaxypyr®)+Tx or cyantraniliprole+Tx;

t) Sulfoxaflor+Tx; or u) Metaflumizone+Tx;

v) Fipronil+Tx and Ethiprole+Tx;

w) Pyrifluqinazon+Tx;

x) buprofezin+Tx; or y) 4-[(6-Chloro-pyridin-3-ylmethyl)-(2,2-difluoro-ethyl)-amino]-5H-furan-2-one (DE 102006015467)+Tx.

z) *Bacillus* species (e.g. *Bacillus firmus*+TX, *Bacillus cereus, Bacillus subtilis*+TX), and *Pasteuria* species (e.g. *Pasteuria penetrans*+TX and *Pasteuria nishizawae*+TX)

aa) flupyradifurone+TX;

ab) CAS: 915972-17-7+TX (WO 2006129714; WO2011/147953; WO2011/147952);

ac) CAS: 26914-55-8+TX (WO 2007020986). In addition to the major chemical classes of pesticide listed above, other pesticides having particular targets may be employed in the composition, if appropriate for the intended utility of the composition. For instance, selective insecticides for particular crops, for example stemborer specific insecticide (combinations such as cartap+Tx) or hopper specific insecticides (combinations such as buprofezin+Tx) for use in rice may be employed. Alternatively insecticides or acaricides specific for particular insect species/stages may also be included in the compositions (for example acaricidal ovo-larvicides, to give combinations such as clofentezine+Tx, flubenzimine+Tx, hexythiazox+Tx or tetradifon+Tx; acaricidal motilicides, to give combinations such as dicofol+Tx or propargite+Tx; acaricides, to give combinations such as bromopropylate+Tx or chlorobenzilate+Tx; or growth regulators, such as hydramethylnon+Tx, cyromazine+Tx, methoprene+Tx, chlorfluazuron+Tx or diflubenzuron+Tx).

Examples of fungicidal compounds and combinations which may be included in the composition of the invention are (E)-N-methyl-2-[2-(2,5-dimethylphenoxymethyl) phenyl]-2-methoxy-iminoacetamide (SSF-129)+Tx, 4-bromo-2-cyano-N,N-dimethyl-6-trifluoromethylbenzimidazole-1-sulfonamide+Tx, α-[N-(3-chloro-2,6-xylyl)-2-methoxyacetamido]-γ-butyrolactone+Tx, 4-chloro-2-cyano-N,N-dimethyl-5-p-tolylimidazole-1-sulfonamide (IKF-916, cyamidazosulfamid)+Tx, 3-5-dichloro-N-(3-chloro-1-ethyl-1-methyl-2-oxopropyl)-4-methylbenzamide (RH-7281, zoxamide)+Tx, N-allyl-4,5-dimethyl-2-trimethylsilylthiophene-3-carboxamide (MON65500)+Tx, N-(1-cyano-1,2-dimethylpropyl)-2-(2,4-dichlorophenoxy)propionamide (AC382042)+Tx, N-(2-methoxy-5-pyridyl)-cyclopropane carboxamide+Tx, acibenzolar (CGA245704) (e.g. acibenzolar-5-methyl)+Tx, alanycarb+Tx, aldimorph+Tx, anilazine+Tx, azaconazole+Tx, azoxystrobin+Tx, benalaxyl+Tx, benomyl+Tx, benthiavalicarb+Tx, biloxazol+Tx, bitertanol+Tx, bixafen+Tx, blasticidin S+Tx, boscalid+Tx, bromuconazole+Tx, bupirimate+Tx, captafol+Tx, captan+Tx, carbendazim+Tx, carbendazim+Tx, chlorhydrate+Tx, carboxin+Tx, carpropamid+Tx, carvone+Tx, CGA41396+Tx, CGA41397+Tx, chinomethionate+Tx, chlorothalonil+Tx, chlorozolinate+Tx, clozylacon+Tx, copper containing compounds to give combintations such as copper oxychloride+Tx, copper oxyquinolate+Tx, copper sulfate+Tx, copper tallate+Tx and Bordeaux mixture+Tx, cyclufenamid+Tx, cymoxanil+Tx, cyproconazole+Tx, cyprodinil+Tx, debacarb+Tx, di-2-pyridyl disulfide 1,1'-dioxide+Tx, dichlofluanid+Tx, diclomezine+Tx, dicloran+Tx, diethofencarb+Tx, difenoconazole+Tx, difenzoquat+Tx, diflumetorim+Tx, O,O-di-iso-propyl-5-benzyl thiophosphate+Tx, dimefluazole+Tx, dimetconazole+Tx, dimethomorph+Tx, dimethirimol+Tx, diniconazole+Tx, dinocap+Tx, dithianon+Tx, dodecyl dimethyl ammonium chloride+Tx, dodemorph+Tx, dodine+Tx, doguadine+Tx, edifenphos+Tx, epoxiconazole+Tx, ethirimo+Tx 1, ethyl-(Z)-N-benzyl-N-([methyl(methyl-thioethylideneaminooxycarbonyl) amino]thio)-β-alaninate+Tx, etridiazole+Tx, famoxadone+Tx, fenamidone (RPA407213)+Tx, fenarimol+Tx, fenbuconazole+Tx, fenfuram+Tx, fenhexamid (KBR2738)+Tx, fenpiclonil+Tx, fenpropidin+Tx, fenpropimorph+Tx, fentin acetate+Tx, fentin hydroxide+Tx, ferbam+Tx, ferimzone+Tx, fluazinam+Tx, fludioxonil+Tx, flumetover+Tx, fluopyram+Tx, fluoxastrobin+Tx, fluoroimide+Tx, fluquinconazole+Tx, flusilazole+Tx, flutolanil+Tx, flutriafol+Tx, fluxapyroxad+Tx, folpet+Tx, fuberidazole+Tx, furalaxyl+Tx, furametpyr+Tx, guazatine, +Tx hexaconazole+Tx, hydroxyisoxazole+Tx, hymexazole+Tx, imazalil+Tx, imibenconazole+Tx, iminoctadine+Tx, iminoctadine triacetate+Tx, ipconazole+Tx, iprobenfos+Tx, iprodione+Tx, iprovalicarb (SZX0722)+Tx, isopropanyl butyl carbamate+Tx, isoprothiolane+Tx, isopyrazam+Tx, kasugamycin+Tx, kresoxim-methyl+Tx, LY186054+Tx, LY211795+Tx, LY248908+Tx, mancozeb+Tx, mandipropamid+Tx, maneb+Tx, mefenoxam+Tx, metalaxyl+Tx, mepanipyrim+Tx, mepronil+Tx, metalaxyl+Tx, metconazole+Tx, metiram+Tx, metiram-zinc+Tx, metominostrobin+Tx, myclobutanil+Tx, neoasozin+Tx, nickel dimethyldithiocarbamate+Tx, nitrothal-isopropyl+Tx, nuarimol+Tx, ofurace+Tx, organomercury compounds, +Tx oxadixyl+Tx, oxasulfuron+Tx, oxolinic acid+Tx, oxpoconazole+Tx, oxycarboxin+Tx, pefurazoate+Tx, penconazole+Tx, pencycuron+Tx, penflufen+Tx, penthiopyrad+Tx, phenazin oxide+Tx, phosetyl-Al+Tx, phosphorus acids+Tx, phthalide+Tx, picoxystrobin (ZA1963)+Tx, polyoxinD+Tx, polyram+Tx, probenazole+Tx, prochloraz+Tx, procymidone+Tx, propamocarb+Tx, propiconazole+Tx, propineb+Tx, propionic acid+Tx, prothioconazole+Tx, pyrazophos+Tx, pyrifenox+Tx, pyrimethanil+Tx, pyraclostrobin+Tx, pyroquilon+Tx, pyroxyfur+Tx, pyrrolnitrin+Tx, quaternary ammonium compounds+Tx, quinomethionate+Tx, quinoxyfen+Tx, quintozene+Tx, sedaxane+Tx, sipconazole (F-155)+Tx, sodium pentachlorophenate+Tx, spiroxamine+Tx, streptomycin+Tx, sulfur+Tx, tebuconazole+Tx, tecloftalam+Tx, tecnazene+Tx, tetraconazole+Tx, thiabendazole+Tx, thifluzamid+Tx, 2-(thiocyanomethylthio)benzothiazole+Tx, thiophanate-methyl+Tx, thiram+Tx, timibenconazole+Tx, tolclofos-methyl+Tx, tolylfluanid+Tx, triadimefon+Tx, triadimenol+Tx, triazbutil+Tx, triazoxide+Tx, tricyclazole+Tx, tridemorph+Tx, trifloxystrobin (CGA279202)+Tx, triforine+Tx, triflumizole+Tx, triticonazole+Tx, validamycin A+Tx, vapam+Tx, vinclozolin+Tx, zineb+Tx and ziram+Tx, N-[9-(dichloromethylene)-1,2,3,4-tetrahydro-1,4-methanonaphthalen-5-yl]-3-(difluoromethyl)-1-methyl-1H-pyrazole-4-carboxamide [1072957-71-1]+Tx, 1-methyl-3-difluoromethyl-1H-pyrazole-4-carboxylic acid (2-dichloromethylene-3-ethyl-1-methyl-indan-4-yl)-amide+Tx, and 1-methyl-3-difluoromethyl-4H-pyrazole-4-carboxylic acid [2-(2,4-dichloro-phenyl)-2-methoxy-1-methylethyl]-amide+Tx.

The active ingredients combinations described above comprising a compound selected of the invention, in particulary from Tables 1 to Table 120 and an active ingredient as described above are preferably combined in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The compounds of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention provides a compound of the invention for use in a method of therapeutic treatment.

In a further aspect the invention relates to a method of controlling parasitic invertebrate pests in or on an animal comprising administering a pesticidally effective amount of a compound of the invention. The administration may be for example oral administration, parenteral administration or external administration, e.g. to the surface of the animal body. In a further aspect the invention relates to a compound of the invention for controlling parasitic invertebrate pests in or on an animal. In a further aspect the invention relates to use of a compound of the invention in the manufacture of a medicament for controlling parasitic invertebrate pests in or on an animal In a further aspect, the invention relates to a method of controlling parasitic invertebrate pests comprising administering a pesticidally effective amount of a compound of the invention to the environment in which an animal resides.

In a further aspect the invention relates to a method of protecting an animal from a parasitic invertebrate pest comprising administering to the animal a pesticidally effective amount of a compound of the invention. In a further aspect the invention relates to a compound of the invention for use in protecting an animal from a parasitic invertebrate pest. In a further aspect the invention relates to use of a compound of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention relates to a compound of the invention for use in treating an animal suffering from a parasitic invertebrate pest. In a further aspect the invention relates to use of a compound of the invention in the manufacture of a medicament for treating an animal suffering from a parasitic invertebrate pest.

In a further aspect, the invention provides a pharmaceutical composition comprising a compound of the invention and a pharmaceutically suitable excipient.

The compounds of the invention may be used alone or in combination with one or more other biologically active ingredients.

In one aspect the invention provides a combination product comprising a pesticidally effective amount of a component A and a pesticidally effective amount of component B wherein component A is a compound of the invention and component B is a compound as described below.

The compounds of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. No. 5,478,855, U.S. Pat. No. 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO95/19363 or WO04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl(E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: *Bacillus thuringiensis* ssp aizawai, kurstaki, *Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the compounds of the invention are preferably used in combination with the following (where "Tx" means a compound of formula (I), and in particular a compound selected from Tables 1 to Table 120, which may result in a synergistic combination with the given active ingredient): imidacloprid+Tx, enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, fipronil+Tx, ivermectin+Tx, omeprazole+Tx, tiamulin+Tx, benazepril+Tx, milbemycin+Tx, cyromazine+Tx, thiamethoxam+Tx, pyriprole+Tx, deltamethrin+Tx, cefquinome+Tx, florfenicol+Tx, buserelin+Tx, cefovecin+Tx, tulathromycin+Tx, ceftiour+Tx, selamectin+Tx, carprofen+Tx, metaflumizone+Tx, moxidectin+Tx, methoprene (including S-methoprene)+Tx, clorsulon+Tx, pyrantel+Tx, amitraz+Tx, triclabendazole+Tx, avermectin+Tx, abamectin+Tx, emamectin+Tx, eprinomectin+Tx, doramectin+Tx, selamectin+Tx, nemadectin+Tx, albendazole+Tx, cambendazole+Tx, fenbendazole+Tx, flubendazole+Tx, mebendazole+Tx, oxfendazole+Tx, oxibendazole+Tx, parbendazole+Tx, tetramisole+Tx, levamisole+Tx, pyrantel pamoate+Tx, oxantel+Tx, morantel+Tx, triclabendazole+Tx, epsiprantel+Tx, fipronil+Tx, lufenuron+Tx, ecdysone+Tx or tebufenozide+Tx; more preferably, enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, omeprazole+Tx, tiamulin+Tx, benazepril+Tx, pyriprole+Tx, cefquinome+Tx, florfenicol+Tx, buserelin+Tx, cefovecin+Tx, tulathromycin+Tx, ceftiour+Tx, selamectin+Tx, carprofen+Tx, moxidectin+Tx, clorsulon+Tx, pyrantel+Tx, eprinomectin+Tx, doramectin+Tx, selamectin+Tx, nemadectin+Tx, albendazole+Tx, cambendazole+Tx, fenbendazole+Tx, flubendazole+Tx, mebendazole+Tx, oxfendazole+Tx, oxibendazole+Tx, parbendazole+Tx, tetramisole+Tx, levamisole+Tx, pyrantel pamoate+Tx, oxantel+Tx, morantel+Tx, triclabendazole+Tx, epsiprantel+Tx, lufenuron+Tx or ecdysone+Tx; even more preferably enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, omeprazole+Tx, tiamulin+Tx, benazepril+Tx, pyriprole+Tx, cefquinome+Tx, florfenicol+Tx, buserelin+Tx, cefovecin+Tx, tulathromycin+Tx, ceftiour+Tx, selamectin+Tx, carprofen+Tx, moxidectin+Tx, clorsulon+Tx or pyrantel+Tx.

Examples of ratios include 100:1 to 1:6000, 50:1 to 1:50, 20:1 to 1:20, even more especially from 10:1 to 1:10, 5:1 to 1:5, 2:1 to 1:2, 4:1 to 2:1, 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

Of particular note is a combination where the additional active ingredient has a different site of action from the compound of formula I. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a compound of formula I and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms.

Thus a wide variety of salts of compounds of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The compounds of the invention also include N-oxides. Accordingly, the invention comprises combinations of compounds of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division. The Manufacturing Confectioner Publishing Co.; and PCT Publication WO 03/024222.

The compounds of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrations, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The compounds of the invention may be particularly suitable for combating external parasitic pests. The compounds of the invention may be suitable for systemic and/or non-systemic control of infestation or infection by parasites on animals.

The compounds of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool). By combating parasites, fatalities and performance reduction (in terms of meat, milk, wool, skins, eggs, etc.) are reduced, so that applying the compounds of the invention allows more economic and simple husbandry of animals.

The compounds of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the compounds of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the compounds of the invention to an animal to be protected include ectoparasites (arthropods, acarines, etc.) and endoparasites (helminths, e.g., nematodes, trematodes, cestodes, acanthocephalans, etc.).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals.

Nematodes that are contemplated to be treated by the compounds of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma*.

Cestodes that are contemplated to be treated by the invention and by the inventive methods include, without limitation, the following genera: *Diphyllobothrium, Diplydium, Spirometra* and *Taenia*.

The most common genera of parasites of the gastrointestinal tract of humans are *Ancylostoma, Necator, Ascaris, Strongy hides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other helminth genera and species are known to the art, and are also contemplated to be treated by the compounds of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, (6th Edition of Monnig's Veterinary Helminthology and Entomology), E. J. L. Soulsby, Williams and Wilkins Co., Baltimore, Md.

The compounds of the invention may be effective against a number of animal ectoparasites (e.g., arthropod ectoparasites of mammals and birds).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi*.

Ticks include, e.g., soft-bodied ticks including *Argasidae* spp. for example *Argalphas* spp. and *Ornithodoros* spp.; hard-bodied ticks including *Ixodidae* spp., for example *Rhipicephalphalus sanguineus, Dermacentor variabilis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The compounds of the invention may also be effective against ectoparasites including: flies such as *Haematobia* (*Lyperosia*) *irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus intestinalis, Gastrophilus haemorrhoidalis* and *Gastrophilus nasalis*; lice such as *Bovicola* (*Damalinia*) *bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites).

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration.

When compounds of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The compounds of the invention may be administered in a controlled release form, for example in subcutaneous or orally adminstered slow release formulations.

Typically a parasiticidal composition according to the present invention comprises a compound of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are compounds of the invention for protecting an animal from an invertebrate parasitic pest comprising a parasitically effective amount of a compound of the invention, optionally in combination with an additional biologically active ingredient and at least one carrier.

For parenteral administration including intravenous, intramuscular and subcutaneous injection, the compounds of the invention can be formulated in suspension, solution or emulsion in oily or aqueous vehicles, and may contain adjuncts such as suspending, stabilizing and/or dispersing agents.

The compounds of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the invention may also be formulated as a depot preparation. Such long acting formulations may be administered by implantation (for example, subcutaneously or intramuscularly) or by intramuscular or subcutaneous injection.

The compounds of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount.

Capsules and cartridges of, for example, gelatin for use in an inhaler or insufflator may be formulated containing a powder mix of the compound and a suitable powder base such as lactose or starch.

The compounds of the invention may have favourable pharmacokinetic and pharmacodynamic properties providing systemic availability from oral administration and ingestion. Therefore after ingestion by the animal to be protected, parasiticidally effective concentrations of a compound of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the compounds of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasiticidal compositions are in the form of feed concentrates, the carrier is typically selected from high-performance feed, feed cereals or protein concentrates.

Such feed concentrate-containing compositions can, in addition to the parasiticidal active ingredients, comprise additives promoting animal health or growth, improving quality of meat from animals for slaughter or otherwise useful to animal husbandry.

These additives can include, for example, vitamins, antibiotics, chemotherapeutics, bacteriostats, fungistats, coccidiostats and hormones.

The compound of the invention may also be formulated in rectal compositions such as suppositories or retention enemas, using, e.g., conventional suppository bases such as cocoa butter or other glycerides.

The formulations for the method of this invention may include an antioxidant, such asBHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the compounds of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly administration intervals (i.e. administering the compounds to the animal once every month).

The following Examples illustrate, but do not limit, the invention.

The following abbreviations were used in this section: s=singlet; bs=broad singlet; d=doublet; dd=double doublet; dt=double triplet; t=triplet; tt=triple triplet; q=quartet, sept=septet; m=multiplet; Me=methyl; Et=ethyl; Pr=propyl; Bu=butyl; M.p.=melting point; RT=retention time, [M+H]$^+$ =molecular mass of the molecular cation, [M−H]$^−$=molecular mass of the molecular anion.

EXAMPLE P1

4-(3,5-Dichloro-phenyl)-5,5,5-trifluoro-pent-2-yne-1,4-diol

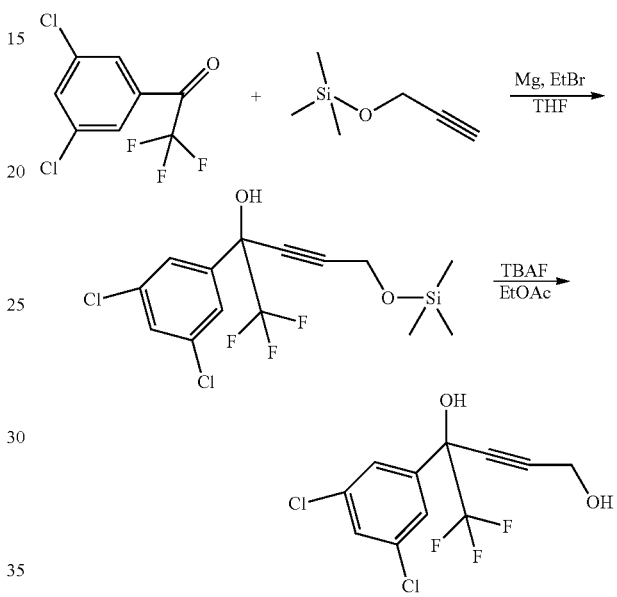

To a stirring solution of magnesium (520 mg) in anhydrous tetrahydrofuran (50 mL) under argon at room temperature, was added ethyl bromide (1.7 mL). After stirring for 2 hours at room temperature, the solution was cooled to 0° C. and Trimethyl-prop-2-ynyloxy-silane (3.1 mL) was added. The solution was allowed to warm to room temperature and then after 40 minutes, it was cooled again to 0° C. To this cooled solution, 1-(3,5-Dichloro-phenyl)-2,2,2-trifluoro-ethanone (5 g) (Journal of Physical Organic Chemistry (1989), 2(4), 363-6) were added. The solution was stirred at 0° C. for 1 hour. The mixture was quenched with saturated ammonium chloride and then extracted with diethyl ether. The combined organic extracts were dried over magnesium sulfate and concentrated. The residue was then dissolved in ethyl acetate (60 mL) and the solution was stirred at room temperature under argon. A solution of tetrabutylammonium fluoride (21 mL of a 1 M solution in tetrahydrofuran) was added. The solution was stirred for one hour then was allowed to stand at room temperature for 21 hours. The mixture was quenched with saturated ammonium chloride and then extracted with diethyl ether. The combined organic extracts were dried over magnesium sulfate and concentrated. The residue was purified by chromatography on silica gel (eluent: heptane/ethyl acetate 1:0 to 7:3) to give 4-(3,5-Dichloro-phenyl)-5,5,5-trifluoro-pent-2-yne-1,4-diol (3.798 g) as a colorless oil.

$^1$H-NMR (CDCl$_3$, 400 MHz): 7.61 (m, 2H), 7.43 (t, J=1.83 Hz, 1H), 4.44 (m, 2H), 3.45 (s, 1H) ppm.

EXAMPLE P2

Tributyl-[5-(3,5-dichloro-phenyl)-5-trifluoromethyl-2,5-dihydro-furan-3-yl]-stannane

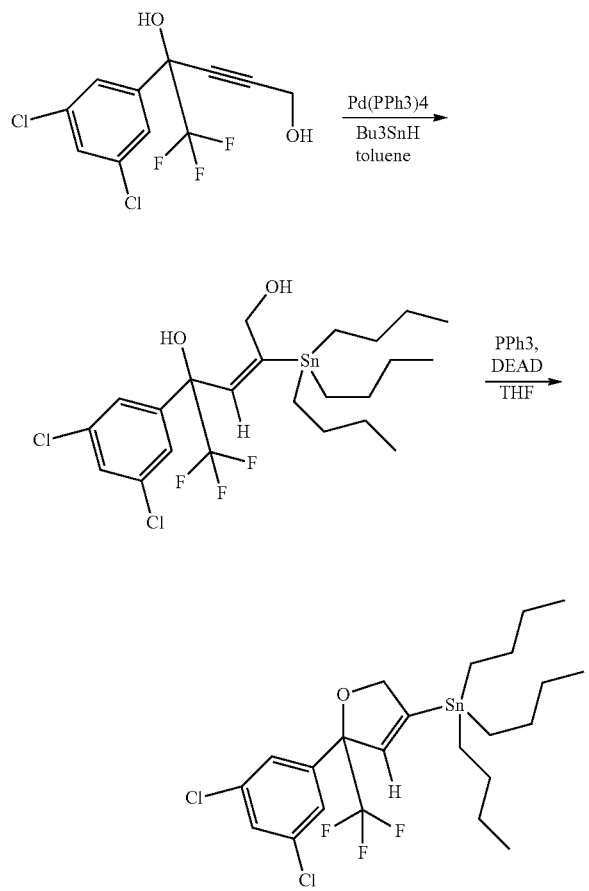

To a solution of 4-(3,5-Dichloro-phenyl)-5,5,5-trifluoro-pent-2-yne-1,4-diol (2.5 g) in toluene under argon, was added tetrakis(triphenylphosphine) palladium (190 mg) and tributyltinhydride (2.25 mL). The reaction mixture was stirred for 45 minutes then the solvent was evaporated under vacuo. The residue was then dissolved in anhydrous tetrahydrofuran (50 mL) with triphenylphosphine (2.19 g) and the solution was stirred at 0° C. under argon. To this solution was slowly added diethyl azodicarboxylate (1.31 mL). The mixture was stirred at 0° C. for 90 minutes then the solvent was evaporated under vacuo. The residue was partitioned between acetonitrile and heptane and the acetonitrile part was washed twice with heptane. The combined heptane extracts were combined and evaporated to give a residue that was purified by chromatography on silica gel (eluent: heptane) to give Tributyl-[5-(3,5-dichloro-phenyl)-5-trifluoromethyl-2,5-dihydro-furan-3-yl]-stannane (1.587 g) as a colorless oil.

$^1$H-NMR (CDCl$_3$, 400 MHz): 7.43 (m, 2H), 7.34 (d, J=1.83 Hz, 1H), 5.93 (t, J=2.57 Hz, 1H), 5.02-4.89 (2x dd, J=2.6 and 13.6 and 1.8 Hz, 2H), 1.52-1.46 (m, 6H), 1.34-1.28 (m, 6H), 1.03-0.99 (t, J=8.1 Hz, 6H), 0.89 (t, J=7.3 Hz, 9H) ppm.

EXAMPLE P3

Preparation of 4-bromo-2-methyl-benzoic acid tert-butyl ester

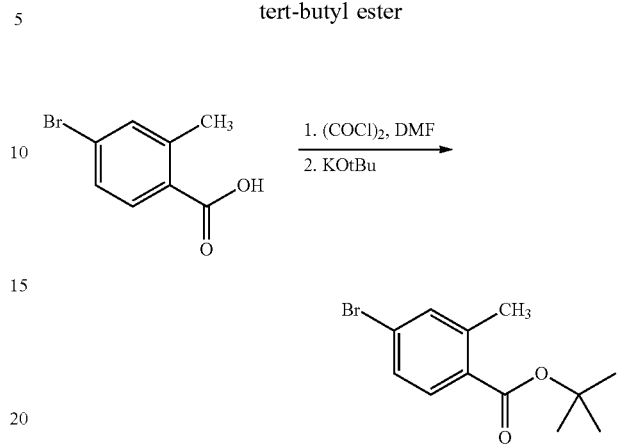

4-Bromo-2-methyl-benzoic acid (commercially available) (50 g) was suspended in dichloromethane (500 mL). A catalytic amount of N,N-dimethylformamide ("DMF") and oxalyl chloride (23 mL) were added to the suspension. The reaction mixture was stirred at ambient temperature for 3 hours. The reaction mixture was concentrated and the residue dissolved in dry tetrahydrofuran (800 mL). The solution was cooled to 2° C. and added to a solution of potassium tert-butoxide (39.2 g) in dry tetrahydrofuran (300 mL) dropwise at 5-10° C. The reaction mixture was stirred at ambient temperature for 30 minutes and then poured onto a mixture of ice and water. The mixture was extracted with ethyl acetate. The organic extract was washed with water, dried over sodium sulfate and concentrated to give 4-bromo-2-methyl-benzoic acid tert-butyl ester (65.3 g) as yellow oil.

$^1$H-NMR (CDCl$_3$, 400 MHz): 7.70 (d, 1H), 7.40 (s, 1H), 7.35 (d, 1H), 2.58 (s, 3H), 1.60 (s, 9H).

EXAMPLE P4

4-[5-(3,5-Dichloro-phenyl)-5-trifluoromethyl-2,5-dihydro-furan-3-yl]-2-methyl-benzoic acid tert-butyl ester

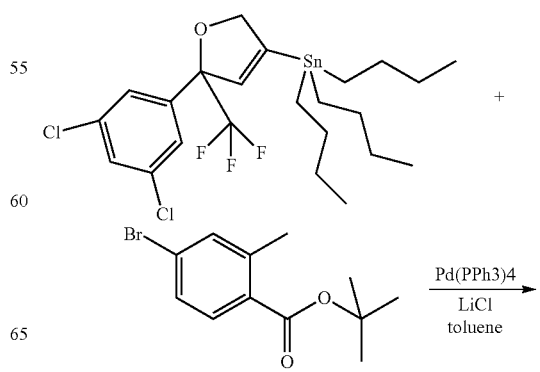

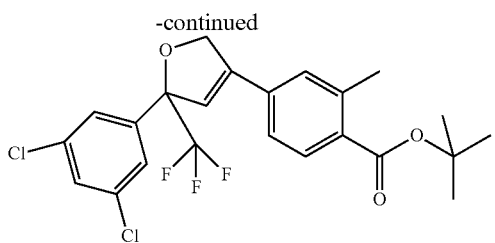

To a solution of Tributyl-[5-(3,5-dichloro-phenyl)-5-trifluoromethyl-2,5-dihydro-furan-3-yl]-stannane (1.587 g) in toluene (15 mL) under argon was successively added 4-Bromo-2-methyl-benzoic acid tert-butyl ester (630 mg), lithium chloride (600 mg) and then tetrakis(triphenylphosphine) palladium (110 mg). The reaction was refluxed at 100° C. under argon for 3 hours 30 minutes. The reaction was allowed to cool down to room temperature then after 3 hours, more tetrakis(triphenylphosphine) palladium (45 mg) was added. The solution was refluxed for a further 1 h45 and then the reaction was stopped. The mixture was cooled to room temperature and then the solvent was evaporated in vacuo to give a residue which was purified by chromatography on silica gel (eluent: heptanes\diethyl ether, from 1:0 to 9:1) to give 4-[5-(3,5-Dichloro-phenyl)-5-trifluoromethyl-2,5-dihydro-furan-3-yl]-2-methyl-benzoic acid tert-butyl ester (704 mg) as a white solid. Recrystallisation in heptane/ethyl acetate provided white crystals, m.p=160-162° C.

$^1$H-NMR (CDCl$_3$, 400 MHz): 7.83 (d, J=8.4 Hz, 1H), 7.50 (m, 2H), 7.38 (t, J=1.4 Hz, 1H), 7.22 (m, 2H), 6.39 (m, 1H), 5.32 (dd, J=2.2 and 12.5 Hz, 1H), 5.20 (m, 1H), 2.59 (s, 3H), 1.61 (s, 9H) ppm.

EXAMPLE P5

4-[5-(3,5-Dichloro-phenyl)-5-trifluoromethyl-2,5-dihydro-furan-3-yl]-2-methyl-benzoic acid

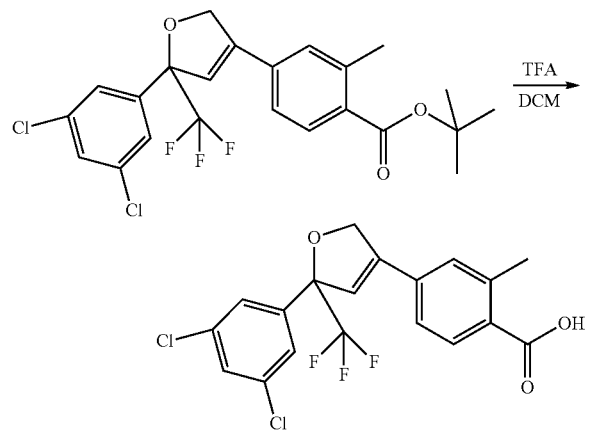

To a solution of 4-[5-(3,5-Dichloro-phenyl)-5-trifluoromethyl-2,5-dihydro-furan-3-yl]-2-methyl-benzoic acid tert-butyl ester (322 mg) in dichloromethane (8 mL) was added trifluoroacetic acid (0.5 mL). The reaction mixture was stirred at room temperature for 3 h30 then the solution was concentrated under vacuo to give 4-[5-(3,5-Dichloro-phenyl)-5-trifluoromethyl-2,5-dihydro-furan-3-yl]-2-methyl-benzoic acid (200 mg) as a white foam.

$^1$H-NMR (CDCl$_3$, 400 MHz): 8.07 (d, J=8.8 Hz, 1H), 7.49 (m, 2H), 7.39 (t, J=1.4 Hz, 1H), 7.3-7.26 (m, 2H), 6.46 (m, 1H), 5.34 (dd, J=2.2 and 12.5 Hz, 1H), 5.22 (m, 1H), 2.67 (s, 3H) ppm.

EXAMPLE P6

Preparation of 4-[(R)-3-(3,5-Dichloro-phenyl)-4,4,4-trifluoro-3-nitromethyl-butyryl]-2-methyl-benzoic acid tert-butyl ester

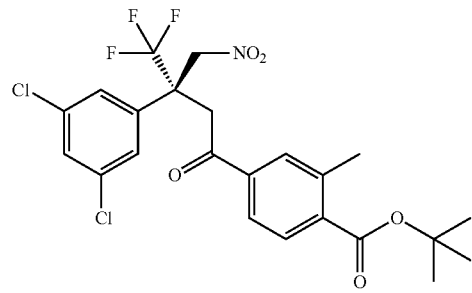 [SMILES: Cc1cc(C(=O)C[C@](C[N+](=O)[O-])(c2cc(Cl)cc(Cl)c2)C(F)(F)F)ccc1C(=O)OC(C)(C)C]

4-[(E)-3-(3,5-Dichloro-phenyl)-4,4,4-trifluoro-but-2-enoyl]-2-methyl-benzoic acid tert-butyl ester (0.0928 g, 0.198 mmol) and 1-[3,5-bis(trifluoromethyl)phenyl]-3-{(S)[(2S,4S,5R)-5-ethyl-1-aza-bicyclo[2.2.2]oct-2-yl]-(6-methoxy-4-quinolinyl)methyl}thiourea (0.0121 g, 0.020 mmol) were dissolved in nitromethane (0.6 ml) and the resulting solution was stirred at 50° C. for 2.5 days. The reaction mixture was cooled to room temperature and aqueous saturated ammonium chloride was added. The resulting mixture was extracted with dichloromethane (3×) and the combined organic fractions were dried over sodium sulfate. The crude product was purified by flash chromatography (0% to 5% ethyl acetate in cyclohexane) to afford 4-[(R)-3-(3,5-dichloro-phenyl)-4,4,4-trifluoro-3-nitromethyl-butyryl]-2-methyl-benzoic acid tert-butyl ester (0.080 g, 77%) as a beige solid. Chiral HPLC analysis (Chiralpack AS-RH, MeCN:MeOH:H$_2$O=75:5:20, 1 ml/min, retention time 3.26 minutes (major enantiomer), 2.86 minutes (minor enantiomer) indicated that the reaction proceeded with 97.4% enantioselectivity.

$^1$H NMR (400 MHz, CDCl$_3$) δ 7.91 (d, 1H), 7.82-7.78 (m, 2H), 7.42 (t, 1H), 7.20 (s, 2H), 5.61 (d, 1H), 5.47 (d, 1H), 4.16 (d, 1H), 3.99 (d, 1H), 2.64 (s, 3H), 1.63 (s, 9H)

The absolute configuration of the major enantiomer was unambiguously assigned as being (R) by X ray diffraction on crystals of the compound (recrystallization from EtOH).

EXAMPLE P7

Preparation of 4-[(R)-4-(3,5-Dichloro-phenyl)-4-trifluoromethyl-4,5-dihydro-3H-pyrrol-2-yl]-2-methyl-benzoic acid tert-butyl ester

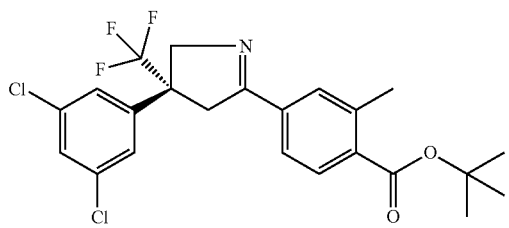 [SMILES: Cc1cc(C2=NC[C@@](c3cc(Cl)cc(Cl)c3)(C(F)(F)F)C2)ccc1C(=O)OC(C)(C)C]

To a vigorously stirred suspension of zinc (0.060 g, 0.913 mmol) in dimethylformamide (2.0 ml) was added a solution of 4-[(R)-3-(3,5-dichloro-phenyl)-4,4,4-trifluoro-3-nitromethyl-butyryl]-2-methyl-benzoic acid tert-butyl ester (0.190 g, 0.365 mmol) in dimethylformamide (2.0 ml). The resulting mixture was warmed to 80° C. and 37% aqueous hydrochloric acid (3.0 ml) was added very slowly to minimize the foaming. After stirring for 2 hours the reaction was cooled to room temperature and quenched by adding a pH 7 buffer solution. The mixture was extracted with dichloromethane; the organic layer was washed with water (3×) and brine. The crude product was purified by flash chromatography (6% ethyl acetate in cyclohexane) to afford 4-[(R)-4-(3,5-dichloro-phenyl)-4-trifluoromethyl-4,5-dihydro-3H-pyrrol-2-yl]-2-methyl-benzoic acid tert-butyl ester as a pale yellow oil (0.050 g, 29%).

$^1$H NMR (400 MHz, CDCl$_3$) δ 7.87 (d, 1H), 7.71 (s, 1H), 7.67 (d, 1H), 7.38 (t, 1H), 7.27 (s, 2H), 4.90 (dd, 1H), 4.45 (d, 1H), 3.81 (dd, 1H), 3.46 (d, 1H), 2.62 (s, 3H), 1.61 (s, 9H)

EXAMPLE P8

Preparation of 4-[(R)-4-(3,5-Dichloro-phenyl)-4-trifluoromethyl-4,5-dihydro-3H-pyrrol-2-yl]-2-methyl-benzoic acid

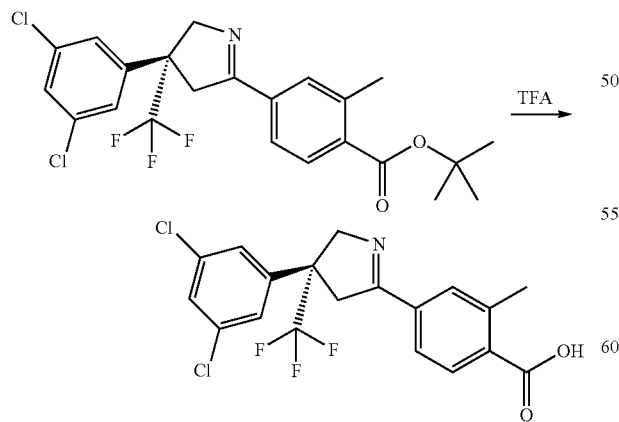

To a solution of 4-[(R)-4-(3,5-Dichloro-phenyl)-4-trifluoromethyl-4,5-dihydro-3H-pyrrol-2-yl]-2-methyl-benzoic acid tert-butyl ester (0.68 g) in dichloromethane (0.7 ml) was added trifluoromethyl acetic acid ("TFA") (0.07 ml). The reaction mixture was stirred at ambient temperature for 4.5 hours. The dichloromethane was evaporated under reduced pressure and the residue was taken up in ethyl acetate and water. The organic phase was washed with water and brine and evaporated under reduced pressure to afford 4-[(R)-4-(3,5-Dichloro-phenyl)-4-trifluoromethyl-4,5-dihydro-3H-pyrrol-2-yl]-2-methyl-benzoic acid which was used as such in the next reaction). LCMS (Method F) RT=2.07 min, [M−H]$^-$=414/416.

EXAMPLE A14

Preparation of 4-[(R)-4-(3,5-Dichloro-phenyl)-4-trifluoromethyl-4,5-dihydro-3H-pyrrol-2-yl]-N—((R)-2-ethyl-3-oxo-isoxazolidin-4-yl)-2-methyl-benzamide

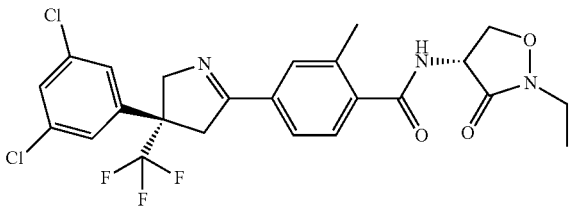 [SMILES: CCN1OC[C@@H](NC(=O)c2ccc(C3=NC[C@@](c4cc(Cl)cc(Cl)c4)(C(F)(F)F)C3)cc2C)C1=O]

To a suspension of 4-[(R)-4-(3,5-Dichloro-phenyl)-4-trifluoromethyl-4,5-dihydro-3H-pyrrol-2-yl]-2-methyl-benzoic acid (22 mg) in dichloromethane (0.45 ml) was added thionyl chloride (0.005 ml) and then one drop of dimethylformamide. The reaction mixture stirred at room temperature for 1 hour, and the solvent was evaporated in vacuo. The acyl chloride thus obtained was dissolved in tetrahydrofuran (0.2 ml) and to the resulting solution was added dropwise to a solution of triethylamine (0.015 ml) and (R)-4-Amino-2-methyl-isoxazolidin-3-one (15 mg) in tetrahydrofuran (0.2 ml) at room temperature, under argon. The reaction was stirred overnight at room temperature. Then the solvent was evaporated in vacuo, the residue was diluted with water and a solution of sodium hydroxide (2N) and extracted with ethyl acetate. The organic phase was washed two times with water, dried over anhydrous sodium sulfate, filtered and concentrated in vacuo. Purification by column chromatography (eluent cyclohexane/ethyl acetate) afforded the title compound as a solid (6.5 mg). $^1$H-NMR (CDCl$_3$, 400 MHz): 7.75 (s, 1H), 7.69 (d, 1H), 7.53 (d, 1H), 7.39 (m, 1H), 7.28 (m, 2H), 6.47 (m, 1H), 5.03-4.84 (m, 3H), 4.46 (d, 1H), 4.06 (t, 1H), 3.83-3.60 (m, 3H), 3.47 (d, 1H), 2.52 (s, 3H), 1.28 (t, 3H).

EXAMPLE P10

(R)-2-Oxo-2lambda*4*-[1,2]oxathiolan-4-ylamine trifluoroacetic acid salt

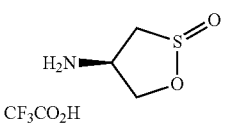

CF$_3$CO$_2$H (2-Oxo-2lambda*4*-[1,2]oxathiolan-4-yl)-carbamic acid tert-butyl ester (prepared in 3 steps from L-cystine according to *J. Org. Chem.* 1981, 46, 5408-5413) (345 mg) was dissolved in dichloromethane (7.8 ml) and treated with trifluoroacetic acid (0.36 ml). The reaction mixture was stirred at room temperature overnight and the solvent removed in vacuo to afford (R)-2-Oxo-2lambda*4*-[1,2]oxathiolan-4-ylamine (trifluoroacetic acid salt), which was used directly in the next step. LCMS (Method E) 0.20 min, M+H 122.

EXAMPLE P11

Method for Preparing the Compounds of the Invention from a Carboxylic Acid

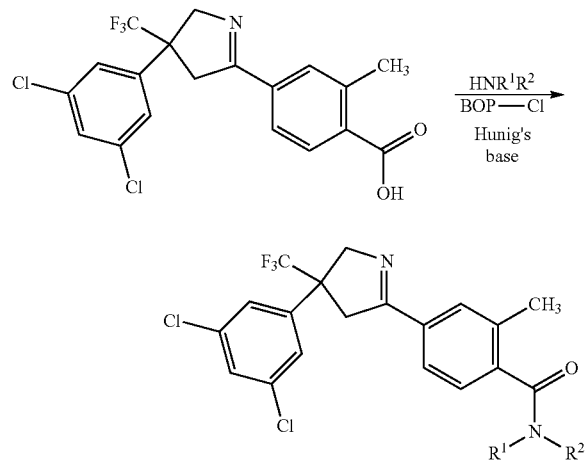

To a solution of the appropriate carboxylic acid (30 µmol), for example 4-[4-(3,5-dichloro-phenyl)-4-trifluoromethyl-4,5-dihydro-3H-pyrrol-2-yl]-2-methyl-benzoic acid (preparation see WO 2010/149506) in the case of compound No. A1 of Table A, in dimethylacetamide (0.4 ml) was added successively a solution of an amine of formula HNR$^1$R$^2$ (36 µmol), for example 2-Oxo-[1,2]oxathiolan-4-ylamine (preparation example P10) in the case of Compound No. A1 of Table A, in dimethylacetamide (0.145 ml), diisopropylethylamine (Hunig's Base) (0.02 ml and a solution of bis(2-oxo-3-oxazolidinyl)phosphonic chloride ("BOP—Cl") (15.3 mg) in dimethylacetamide (0.2 ml). The reaction mixture was stirred at 90° C. for 16 hours. Then the reaction mixture was diluted with acetonitrile (0.6 ml) and a sample was used for LC-MS analysis. The remaining mixture was further diluted with acetonitrile/dimethylformamide (4:1) (0.8 ml) and separated by HPLC. This method was used to prepare a number of compounds (Compound Nos. A1 to A4 and A7 to A11 of Table A) in parallel, A5 and A6 were obtained using a similar procedure.

EXAMPLE P12

Method for Preparing the Compounds of the Invention from a Carboxylic Acid

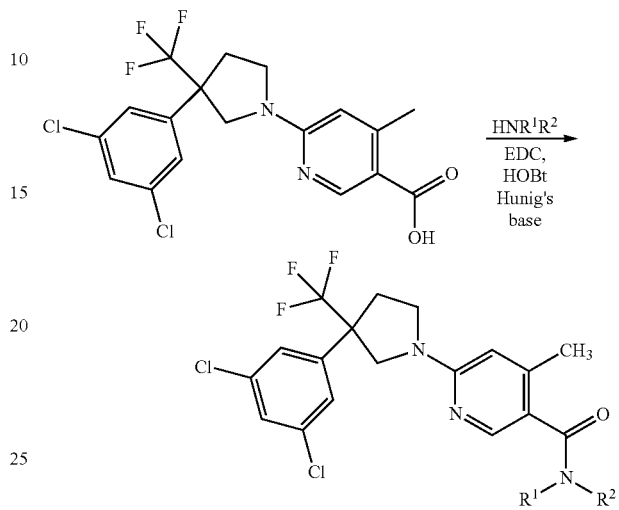

To a solution of the appropriate carboxylic acid (25 µmol), for example 6-[3-(3,5-Dichloro-phenyl)-3-trifluoromethyl-pyrrolidin-1-yl]-4-methyl-nicotinic acid (preparation described in JP 2008/110971) in dimethylacetamide (0.4 ml) was added an amine of formula HNR$^1$R$^2$ (37.5 µmol), for example ethyl cacloserine (preparation described in, for example, WO 2008/033562) in the case of compound No. B1 of Table B, diisopropylethylamine (Hunig's Base) (0.020 ml), followed by 1-ethyl-3-(3-dimethylaminopropyl)carbodiimid (EDC) (14 mg) in dimethylacetamide (0.02 ml) and hydroxybenzotriazole (HOBt) (3.7 mg) in dimethylacetamide (0.01 ml). The reaction mixture was stirred at ambient temperature for 16 hours. The reaction mixture was diluted with acetonitrile/dimethylformamide (4:1) (0.8 ml) and purified by HPLC. This method was used to prepare a number of compounds (Compound Nos. B1 to B4 of Table B) in parallel.

EXAMPLE P13

Reference

Preparation of 4-[2-(3,5-dichlorophenyl)-2-(trifluoromethyl)-3H-furan-4-yl]-2-methyl-N-[(4R)-3-oxo-2-(2,2,2-trifluoroethyl)isoxazolidin-4-yl]benzamide (C2)

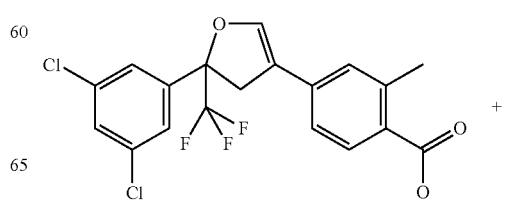

-continued

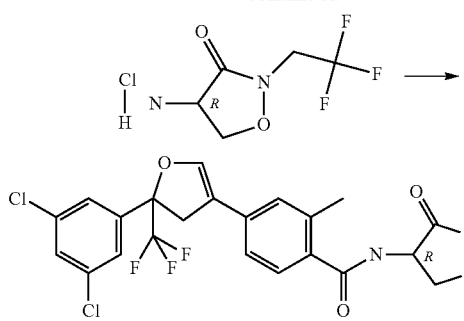

To a suspension of 4-[2-(3,5-dichlorophenyl)-2-(trifluoromethyl)-3H-furan-4-yl]-2-methyl-benzoic acid (250 mg, prepared as described in WO2011101229) in dichloromethane (5 ml) was added thionyl chloride (0.06 ml) and then two drops of dimethylformamide. The reaction mixture was stirred at room temperature for 1 hour, and the solvent was evaporated in vacuo. The acyl chloride thus obtained was dissolved in dichloromethane (1 ml) and was added dropwise to a suspension of triethylamine (0.25 ml) and the hydrochloride salt of (4R)-4-amino-2-(2,2,2-trifluoroethyl) isoxazolidin-3-one (145 mg) in dichloromethane (5 ml) at room temperature, under argon. The reaction was stirred for 40 minutes at room temperature. Then the reaction was diluted with water and extracted with ethyl acetate. The organic phase was washed two times with water, dried over anhydrous magnesium sulfate, filtered and concentrated in vacuo. Purification by column chromatography (eluent cyclohexane/ethyl acetate, 1:0 to 0:1) afforded the title compound as a solid (215 mg). $^1$H-NMR (CDCl$_3$, 400 MHz): □=7.47-7.55 (m, 2H), 7.37-7.45 (m, 2H), 7.06-7.14 (m, 2H), 7.01 (s, 1H), 6.33 (d, J=4.4 Hz, 1H), 4.98-5.09 (m, 1H), 4.93 (ddd, J=10.5, 8.3, 4.4 Hz, 1H), 4.03-4.31 (m, 3H), 3.74 (dd, J=15.0, 2.2 Hz, 1H), 3.30 (d, J=15.8 Hz, 1H), 2.47 ppm (s, 3H)

EXAMPLE P14

Reference

Preparation of 4-[2-(3,5-dichlorophenyl)-2-(trifluoromethyl)-3H-furan-4-yl]-N-[(4R)-2-ethyl-3-oxoisoxazolidin-4-yl]-2-methyl-benzamide (C1)

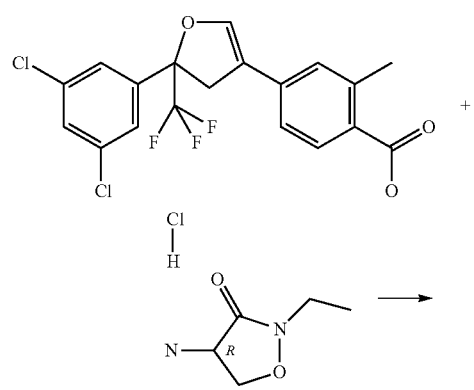

-continued

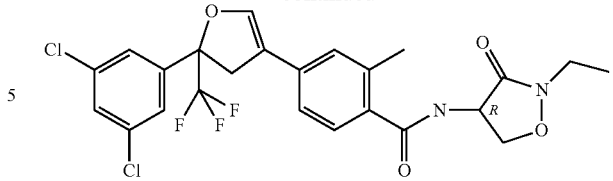

To a suspension of 4-[2-(3,5-dichlorophenyl)-2-(trifluoromethyl)-3H-furan-4-yl]-2-methyl-benzoic acid (250 mg, prepared as described in WO2011101229) in dichloromethane (4 ml) was added thionyl chloride (0.06 ml) and then two drops of dimethylformamide. The reaction mixture was stirred at room temperature for 1 hour, and the solvent was evaporated in vacuo. The acyl chloride thus obtained was dissolved in dichloromethane (1 ml) and was added dropwise to a suspension of triethylamine (0.25 ml) and the hydrochloride salt of (4R)-4-amino-2-ethylisoxazolidin-3-one (120 mg) in dichloromethane (5 ml) at room temperature, under argon. The reaction was stirred overnight at room temperature. Then the reaction was diluted with water and extracted with ethyl acetate. The organic phase was washed two times with water, dried over anhydrous magnesium sulfate, filtered and concentrated in vacuo. Purification by column chromatography (eluent cyclohexane/ethyl acetate, 1:0 to 0:1) afforded the title compound as a solid (182 mg). $^1$H-NMR (CDCl$_3$, 400 MHz): □=7.49 (d, J=1.5 Hz, 2H), 7.42 (dt, J=3.9, 2.2 Hz, 2H), 7.05-7.14 (m, 2H), 7.00 (s, 1H), 6.38 (d, J=3.7 Hz, 1H), 4.94-5.05 (m, 1H), 4.04 (dd, J=11.0, 8.4 Hz, 1H), 3.56-3.80 (m, 3H), 3.32 (s, 1H), 2.47 ppm (s, 3H)

EXAMPLE P15

Preparation of 4-[3-(3,5-dichlorophenyl)-3-(trifluoromethyl)-2,4-dihydropyrrol-5-yl]-2-methyl-N-[(4R)-3-oxoisoxazolidin-4-yl]benzamide (compound D1)

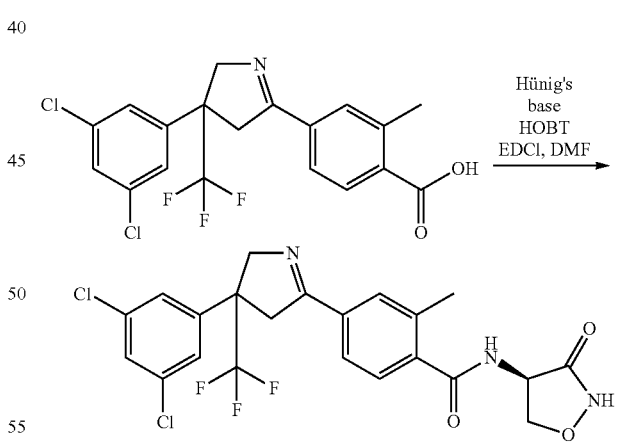

D-Cycloserine (0.58 g) was added to a solution of 4-[3-(3,5-dichlorophenyl)-3,4-dihydro-3-(trifluoromethyl)-2H-pyrrol-5-yl]-2-methyl-benzoic acid, (1 g) (prepared according to WO 2010/020522) in N,N-dimethylformamide ("DMF") (20 ml), followed by the addition of Hünig's base (1.9 ml), hydroxybenzotriazole (HOBT) (0.28 g) and 1-(3-Dimethylaminopropyl)-3-ethylcarbodiimide hydrochloride (EDCl) (0.54 g). The reaction mixture was stirred at ambient temperature for 63 hours. Further N,N-dimethylformamide ("DMF") (10 ml) was added and the reaction mixture was stirred at ambient temperature for another 24 hours.

The reaction mixture was diluted with water and extracted 3 times with ethyl acetate. The organic phases were combined, washed twice with water, dried over sodium sulfate and concentrated. The residue was purified by chromatography on silica gel (eluent: dichloromethane/methanol) to give the title compound (135 mg) as a colorless solid.

EXAMPLE II

General Method for Preparing the Compounds of the Invention in Parallel

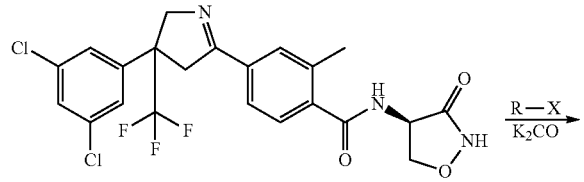

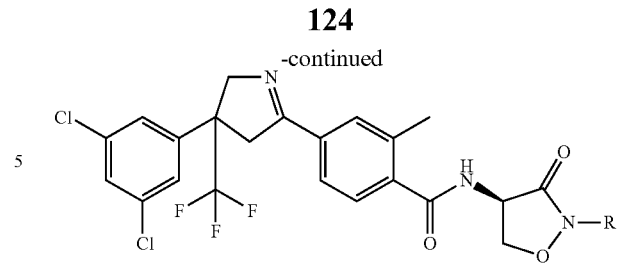

To a solution of 4-[3-(3,5-dichlorophenyl)-3-(trifluoromethyl)-2,4-dihydropyrrol-5-yl]-2-methyl-N-[(4R)-3-oxoisoxazolidin-4-yl]benzamide (compound B1) (12.5 µmol) in N,N-dimethylformamide ("DMF") (0.2 ml) was added potassium carbonate (25 µmol). The suspension was stirred for 3 hours at ambient temperature. A solution of an alkylhalogenide of formula R—X (22 µmol) in N,N-dimethylformamide ("DMF") (0.2 ml) was added and reaction mixture was stirred at ambient temperature for 16 hours. Then the reaction mixture was separated by HPLC. This method was used to prepare a number of compounds (Compound Nos. D2 to D18 of Table D) in parallel

TABLE A

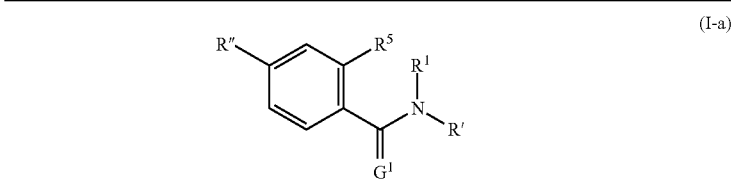

(I-a)

| Compound No. | R' | R'' | RT (min) | [M + H]⁺ | LC-MS method |
|---|---|---|---|---|---|
| A1 (isomer A) | 2-Oxo-[1,2]oxathiolan-4-yl- | 4-(3,5-Dichloro-phenyl)-4-trifluoromethyl-4,5-dihydro-3H-pyrrol-2-yl | 1.68 | 519.2 | B |
| A2 (isomer B) | 2-Oxo-[1,2]oxathiolan-4-yl- | 4-(3,5-Dichloro-phenyl)-4-trifluoromethyl-4,5-dihydro-3H-pyrrol-2-yl | 1.72 | 519.2 | B |
| A3 (isomer A) | 2-Oxo-[1,2]oxathiolan-4-yl- | 4-(3,4,5-Trichloro-phenyl)-4-trifluoromethyl-4,5-dihydro-3H-pyrrol-2-yl | 1.78 | 553.2 | B |
| A4 (isomer B) | 2-Oxo-[1,2]oxathiolan-4-yl- | 4-(3,4,5-Trichloro-phenyl)-4-trifluoromethyl-4,5-dihydro-3H-pyrrol-2-yl | 1.83 | 553.2 | B |
| A5 | 2-Ethyl-3-oxo-isoxazolidin-4-yl | 4-(3,5-Dichloro-phenyl)-4-trifluoromethyl-4,5-dihydro-3H-pyrrol-2-yl | 1.97 | 528.0 | A |
| A6 | 2-Ethyl-3-oxo-isoxazolidin-4-yl | 4-(3,4,5-Trichloro-phenyl)-4-trifluoromethyl-4,5-dihydro-3H-pyrrol-2-yl | 2.07 | 564.0 | A |
| A7 | (R)-2-Ethyl-3-oxo-isoxazolidin-4-yl | 4-(3,4,5-Trichloro-phenyl)-4-trifluoromethyl-4,5-dihydro-3H-pyrrol-2-yl | 1.85 | 562.2 | B |
| A8 | (R)-2-Ethyl-3-oxo-isoxazolidin-4-yl | 3-(3,5-Dichloro-phenyl)-3-trifluoromethyl-pyrrolidinyl | 1.70 | 530.3 | B |
| A9 | (R)-3-Oxo-2-(2,2,2-trifluoro-ethyl)-isoxazolidin-4-yl | 4-(3,4,5-Trichloro-phenyl)-4-trifluoromethyl-4,5-dihydro-3H-pyrrol-2-yl | 1.96 | 616.2 | B |
| A10 | (R)-3-Oxo-2-(2,2,2-trifluoro-ethyl)-isoxazolidin-4-yl | 3-(3,5-Dichloro-phenyl)-3-trifluoromethyl-pyrrolidinyl | 1.81 | 584.1 | B |
| A11 | (R)-3-Oxo-2-(2,2,2-trifluoro-ethyl)-isoxazolidin-4-yl | (R)-4-(3,5-Dichloro-phenyl)-4-trifluoromethyl-4,5-dihydro-3H-pyrrol-2-yl | 1.86 | 582.4 | B |
| A12 | (R)-2-Ethyl-3-oxo-isoxazolidin-4-yl | 5-(3,5-Dichloro-phenyl)-5-trifluoromethyl-2,5-dihydro-furan-3-yl | 1.94 | 529.3 | B |
| A13 | (R)-3-Oxo-2-(2,2,2-trifluoro- | 5-(3,5-Dichloro-phenyl)-5-trifluoromethyl- | 2.03 | 583.3 | B |

TABLE A-continued

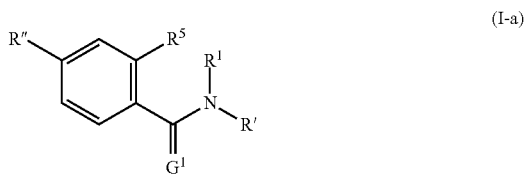
(I-a)

| Compound No. | R' | R" | RT (min) | [M + H]+ | LC-MS method |
|---|---|---|---|---|---|
| | ethyl)-isoxazolidin-4-yl | 2,5-dihydro-furan-3-yl | | | |

Table A provides compounds of formula (I-a) where $G^1$ is oxygen, $R^5$ is methyl, $R^1$ is hydrogen and R' and R" have the values listed in the table below.

TABLE B

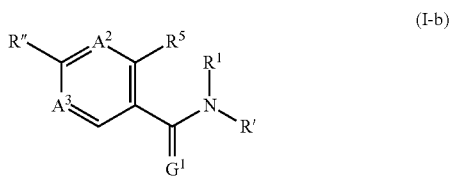
(I-b)

| Compound No. | $A^2$ | $A^3$ | R' | R" | RT (min) | [M + H]+ | LC-MS method |
|---|---|---|---|---|---|---|---|
| B1 | C | N | 2-Ethyl-3-oxo-isoxazolidin-4-yl | 3-(3,5-Dichloro-phenyl)-3-trifluoromethyl-pyrrolidinyl | 1.57 | 531.4 | B |
| B2 | C | N | 3-Oxo-2-(2,2,2-trifluoro-ethyl)-isoxazolidin-4-yl | 3-[(3,5-Dichloro-phenyl)-3-trifluoromethyl-pyrrolidinyl | 1.73 | 585.3 | B |
| B3 | N | C | 2-Ethyl-3-oxo-isoxazolidin-4-yl | 3-(3,5-Dichloro-phenyl)-3-trifluoromethyl-pyrrolidinyl | 1.65 | 531.4 | B |
| B4 | N | C | 3-Oxo-2-(2,2,2-trifluoro-ethyl)-isoxazolidin-4-yl | 3-(3,5-Dichloro-phenyl)-3-trifluoromethyl-pyrrolidinyl | 1.81 | 585.3 | B |

Table B provides compounds of formula (I-b) where $G^1$ is oxygen, $R^5$ is methyl, $R^1$ is hydrogen and X, Y, R' and R" have the values listed in the table below.

TABLE C (Reference):

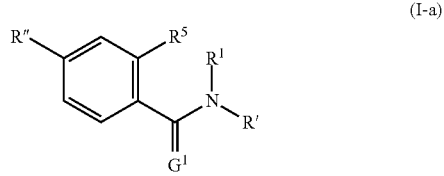
(I-a)

| Compound No. | R' | R" |
|---|---|---|
| C1 | (R)-2-Ethyl-3-oxo-isoxazolidin-4-yl | 4-[5-(3,5-Dichloro-phenyl)-5-trifluoromethyl-4,5-dihydro-furan-3-yl]- |
| C2 | (R)-3-Oxo-2-(2,2,2-trifluoro-ethyl)-isoxazolidin-4-yl | 4-[5-(3,5-Dichloro-phenyl)-5-trifluoromethyl-4,5-dihydro-furan-3-yl]- |

Table C provides compounds of formula (I-a) where $G^1$ is oxygen, $R^5$ is methyl, $R^1$ is hydrogen and R' and R" have the values listed in the table below.

TABLE D

Compounds of formula (I-c):

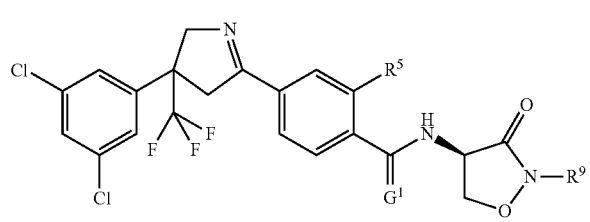
(I-c)

| Comp No. | $R^5$ | $G^1$ | $R^9$ | LCMS Method | RT (min) | (M + H)- (measured) |
|---|---|---|---|---|---|---|
| D1 | Me | O | H | C | 0.98 | 500 |
| D2 | Me | O | 3-methyl-but-2-enyl | J | 1.94 | 568.34 |

TABLE D-continued

Compounds of formula (I-c):

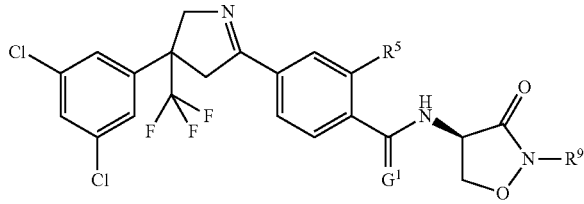

(I-c)

| Comp No. | R⁵ | G¹ | R⁹ | LCMS Method | RT (min) | (M + H)– (measured) |
|---|---|---|---|---|---|---|
| D3 | Me | O | 4-nitro-benzyl | J | 1.91 | 635.09 |
| D4 | Me | O | 1,1,1-trifluoropropan-3-yl | J | 1.87 | 596.23 |
| D5 | Me | O | 4-fluoro-benzyl | J | 1.94 | 608.47 |
| D6 | Me | O | 1,1,1-trifluorobutan-4-yl | J | 1.92 | 610.22 |
| D7 | Me | O | 2,6-difluoro-benzyl | J | 1.93 | 626.28 |
| D8 | Me | O | cyclopropylmethyl | J | 1.87 | 554.30 |
| D9 | Me | O | 2-[1,3]dioxan-2-yl-ethyl | J | 1.77 | 613.64 |
| D10 | Me | O | 5-trifluoromethyl-furan-2-ylmethyl | J | 2.00 | 648.30 |
| D11 | Me | O | 2,5-dimethyl-2H-[1,2,3]triazol-4-yl-methyl | J | 1.74 | 609.38 |
| D12 | Me | O | cyclobutylmethyl | J | 1.96 | 568.20 |
| D13 | Me | O | (propan-2-one O-methyl-oxime)-1-yl | J | 1.83 | 585.33 |
| D14 | Me | O | allyl | J | 1.79 | 540.31 |
| D15 | Me | O | 3-cyanopropyl | J | 1.71 | 567.39 |
| D16 | Me | O | 3-phenyl-propyl | J | 2.05 | 618.37 |
| D17 | Me | O | cyclohexylmethyl | J | 2.10 | 596.43 |
| D18 | Me | O | 4-methoxybutyl | J | 1.81 | 586.02 |

The following LC-MS methods were used to characterize the compounds:

Method A

| | |
|---|---|
| MS | ACQUITY SQD Mass Spectrometer from Waters (Single quadrupole mass spectrometer) Ionisation method: Electrospray Polarity: positive ions Capillary (kV) 3.00, Cone (V) 20.00, Extractor (V) 3.00, Source Temperature (150° C.) Desolvation Temperature (° C.) 400, Cone Gas Flow (L/Hr) 60, Desolvation Gas Flow (L/Hr) 700, Mass range: 100 to 800 Da |
| LC | Method Waters ACQUITY UPLC with the following HPLC gradient conditions (Solvent A: water/methanol 9:1, 0.1% formic acid and Solvent B: acetonitrile, 0.1% formic acid) DAD Wavelength range (nm): 210 to 400 Type of column: Waters ACQUITY UPLC HSS T3; Column length: 30 mm; Internal diameter of column: 2.1 mm; Particle Size: 1.8 micron; Temperature: 60° C. |

| Time (min) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Method B

| | |
|---|---|
| MS | ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da. |
| LC | 1100er Series HPLC from Agilent: quaternary pump, heated column compartment and diode-array detector. Column: Waters Atlantis dc18; length: 20 mm; internal diameter: 3 mm; particle size: 3 μm, temperature (° C.) 40, DAD wavelength range (nm): 200 to 500, solvent gradient: A = 0.1% of formic acid in water and B: 0.1% of formic acid in acetonitrile. |

| Time (min) | A (%) | B (%) | Flow rate (ml/min) |
|---|---|---|---|
| 0.0 | 90 | 10 | 1.7 |
| 5.5 | 0.0 | 100 | 1.7 |
| 5.8 | 0.0 | 100 | 1.7 |
| 5.9 | 90 | 10 | 1.7 |

Method C

| | |
|---|---|
| MS | SQD Mass Spectrometer from Waters (Single quadrupole mass spectrometer) Instrument Parameter: Ionization method: Electrospray Polarity: positive and negative ions Capillary: 3.00 kV; Cone: 45.00 V Extractor: 2.00 V; Source Temperature: 150° C., Desolvation Temperature: 250° C.; Cone Gas Flow: 0 L/Hr Desolvation Gas Flow: 650 L/Hr; Mass range: 100 to 900 Da |
| LC | Acquity UPLC from Waters: Binary pump, heated column compartment and diode-array detector. |

Method C

Solvent degasser, binary pump, heated column compartment and diode-array detector.
Column: Phenomenex Gemini C18, 3 □m, 30 × 2 mm,
Temp: 60° C.
DAD Wavelength range (nm): 210 to 500
Solvent Gradient:
A = H2O + 5% MeOH + 0.05% HCOOH;
B = Acetonitril + 0.05% HCOOH

| Time | A % | B % | Flow (ml/min) |
|---|---|---|---|
| 0.00 | 100 | 0 | 0.850 |
| 1.2 | 0 | 100.0 | 0.850 |
| 1.50 | 0 | 100.0 | 0.850 |

Method E

MS  ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da.

LC  1100er Series HPLC from Agilent: quaternary pump, heated column compartment and diode-array detector. Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile.

| Time (min) | A % | B % | Flow (ml/min) |
|---|---|---|---|
| 0.0 | 80 | 20 | 1.7 |
| 2.5 | 0.0 | 100 | 1.7 |
| 2.8 | 0.0 | 100 | 1.7 |
| 2.9 | 80 | 20 | 1.7 |

Method F

MS  ZQ Mass Spectrometer from Waters (single quadrupole mass spectrometer), ionization method: electrospray, polarity: negative ionization, capillary (kV) 3.00, cone (V) 45.00, source temperature (° C.) 100, desolvation temperature (° C.) 250, cone gas flow (L/Hr) 50, desolvation gas flow (L/Hr) 400, mass range: 150 to 1000 Da.

LC  HP 1100 HPLC from Agilent: solvent degasser, binary pump, heated column compartment and diode-array detector. Column: Phenomenex Gemini C18, length (mm) 30, internal diameter (mm) 3, particle size (μm) 3, temperature (° C.) 60, DAD wavelength range (nm): 200 to 500, solvent gradient: A = 0.05% v/v formic acid in water and B = 0.04% v/v formic acid in acetonitrile/methanol (4:1).

| Time (min) | A % | B % | Flow (ml/min) |
|---|---|---|---|
| 0.0 | 95 | 5.0 | 1.7 |
| 2.0 | 0.0 | 100 | 1.7 |
| 2.8 | 0.0 | 100 | 1.7 |
| 2.9 | 95 | 5.0 | 1.7 |
| 3.1 | 95 | 5 | 1.7 |

Method J

MS  Waters ACQUITY SQD Mass Spectrometer from Waters (Single quadrupole mass spectrometer)
Ionisation method: Electrospray
Polarity: positive ions
Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 100 to 800 Da
DAD Wavelength range (nm): 210 to 400

LC  Waters ACQUITY UPLC with the following HPLC gradient conditions (Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3;
Column length: 30 mm; Internal diameter of column: 2.1 mm;
Particle Size: 1.8 micron; Temperature: 60° C.

BIOLOGICAL EXAMPLES

This Example illustrates the insecticidal and acaricidal properties of compounds of formula (I). The tests were performed as follows:

*Spodoptera Littoralis* (Egyptian Cotton Leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compound gave at least 80% control of *Spodoptera littoralis*: A5, A6, A7, A8, A9, A10, B1, B2, B3, B4, A14, A11, A13, A12, D8, D15, D18, C1, C2.

*Heliothis Virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compound gave at least 80% control of *Heliothis virescens*: A5, A6, A7, A8, A9, A10, B1, B2, B3, B4, A14, A11, A4, A13, A12, D4, D8, D11, D12, D13, D14, D15, D16, D18, C1, C2.

*Plutella Xylostella* (Diamond Back Moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compound gave at least 80% control of *Plutella xylostella*: A5, A6, A7, A8, A9, A10, B2, B3, B4, A14, A11, A13, A12, D2, D4, D5, D7, D8, D11, D12, D13, D14, D15, C1, C2.

*Diabrotica Balteata* (Corn Root Worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compound gave at least 80% control of *Diabrotica balteata*: A5, A6, A7, A8, A9, A10, B2, B3, B4, A14, A11, A13, A12, D4, D5, D6, D7, D10, D13, D14, D16, C1, C2.

*Thrips Tabaci* (Onion Thrips):

Sunflower leaf discs were placed on agar in a 24-well microtiter plate and sprayed with test solutions at an application rate of 200 ppm. After drying, the leaf discs were infested with a thrip population of mixed ages. After an incubation period of 7 days, samples were checked for mortality.

The following compounds gave at least 80% control of *Thrips tabaci*: A5, A6, A7, A8, A9, A10, B3, B4, A14, A11, A13, A12, D4, D15, C1, C2.

*Tetranychus Urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compound gave at least 80% control of *Tetranychus urticae*: A5, A6, A7, A8, A9, A10, B1, B2, B3, B4, A14, A11, A13, A12, D2, D3, D4, D5, D6, D7, D8, D9, D10, D11, D12, D13, D14, D15, D16, C1, C2.

The invention claimed is:

1. A compound of formula (I):

wherein
$A^1$ is C—$R^5$;
$A^2$, $A^3$ and $A^4$ are each C—H;
$B^1$—$B^2$—$B^3$—$B^4$ is —$CH_2$—C=N—$CH_2$—;
$G^1$ is oxygen;
L is a single bond;
$R^1$ is hydrogen;
$R^2$ is hydrogen;
$R^3$ is trifluoromethyl;
$R^4$ is 3,5-dichlorophenyl-;
$R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl;
$Y^1$ is C=O;
$Y^2$ is N—$R^9$;
$Y^3$ is O; and
$Y^4$ is $CR^7R^8$;
each $R^7$ and $R^8$ is independently hydrogen;
each $R^9$ is independently hydrogen, cyano, cyano-$C_1$-$C_8$alkyl, $C_1$-$C_8$alkyl, $C_1$-$C_8$haloalkyl, $C_3$-$C_8$cycloalkyl, $C_3$-$C_8$cycloalkyl where one carbon atom is replaced by O, S, S(O) or $SO_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or $SO_2$, or $C_3$-$C_8$cycloalkyl-$C_1$-$C_8$haloalkyl, $C_1$-$C_8$hydroxyalkyl, $C_1$-$C_8$alkoxy-$C_1$-$C_8$alkyl, $C_2$-$C_8$alkenyl, $C_2$-$C_8$haloalkenyl, $C_2$-$C_8$alkynyl, $C_2$-$C_8$haloalkynyl, phenyl, phenyl substituted by one to three $R^{10}$, heteroaryl, heteroaryl substituted by one to three $R^{10}$, phenyl-$C_1$-$C_4$alkyl, phenyl-$C_1$-$C_4$alkyl wherein the phenyl moiety is substituted by one to three $R^{10}$, heteroaryl-$C_1$-$C_4$alkyl or heteroaryl-$C_1$-$C_4$alkyl wherein the heteroaryl moiety is substituted by one to three $R^{10}$, or $C_1$-$C_4$alkyl-($C_1$-$C_4$alkyl-O—N=)C—$CH_2$—;

each $R^{10}$ is independently halogen, cyano, nitro, $C_1$-$C_8$alkyl, $C_1$-$C_8$haloalkyl, $C_1$-$C_8$alkoxy, or $C_1$-$C_8$haloalkoxy; or a salt or N-oxide thereof.

2. A compound according to claim 1, wherein $R^5$ is halogen, nitro, $C_1$-$C_4$alkyl, $C_3$-$C_4$cycloalkyl, $C_2$-$C_4$alkenyl or $C_1$-$C_4$haloalkyl.

3. A compound according to claim 1, wherein each $R^5$ independently is bromo, chloro, fluoro, cyclopropyl, trifluoromethyl, vinyl, or methyl.

4. A compound according to claim 1, wherein each $R^9$ is independently hydrogen, cyano-$C_1$-$C_8$alkyl, $C_1$-$C_8$alkyl, $C_3$-$C_8$cycloalkyl, $C_3$-$C_8$cycloalkyl where one carbon atom in the cycloalkyl group is replaced by 0, S, S(O) or $SO_2$, or $C_1$-$C_8$haloalkyl, $C_1$-$C_8$hydroxyalkyl, $C_2$-$C_8$alkenyl, $C_2$-$C_8$alkynyl, phenyl-$C_1$-$C_4$alkyl or phenyl-$C_1$-$C_4$alkyl wherein the phenyl moiety is substituted by one to three $R^{10}$, 5-6 membered heteroaryl-$C_1$-$C_4$alkyl or 5-6 membered heteroaryl-$C_1$-$C_4$alkyl wherein the heteroaryl moiety is substituted by one to three $R^{10}$, and wherein the heteroaryl is pyridyl, pyridazinyl, pyrimidinyl, pyrazinyl, pyrazolyl, furanyl, thiophenyl, oxazolyl, isoxazolyl or thiazolyl.

5. A compound according to claim 1, wherein each $R^9$ is independently hydrogen, $C_1$-$C_4$alkyl, $C_3$-$C_6$cycloalkyl, $C_1$-$C_4$haloalkyl, $C_1$-$C_4$hydroxyalkyl, $C_1$-$C_4$alkoxy-$C_1$-$C_4$alkyl, phenyl-$CH_2$-alkyl- or phenyl-$CH_2$— wherein the phenyl moiety is substituted by one to three $R^{10}$, furanyl or furanyl substituted by one to three $R^{10}$, thietanyl, oxetanyl, oxo-thietanyl, or dioxo-thietanyl.

6. A method of combating and/or controlling an invertebrate animal pest which comprises applying to the pest, to a locus of the pest, or to a plant susceptible to attack by the pest a pesticidally effective amount of a compound of formula (I) as defined in claim 1.

7. A composition comprising a pesticidally effective amount of a compound of formula (I) as defined in claim 1 optionally comprising an additional pesticidally active ingredient.

8. A combination product comprising a pesticidally effective amount of a component A and a pesticidally effective amount of component B, wherein component A is a compound of formula (I) as defined in claim 1, and component B is imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide.

* * * * *